US004001638B2

United States Statutory Invention Registration [19]

[11] Reg. Number: H1638

[45] Published: Mar. 4, 1997

Furuta et al.

[54] USE OF THE POLYPEPTIDE COMPOUND

[76] Inventors: Takahisa Furuta, 2-1-5-815, Omoriminami, Ota-ku, Tokyo 143; Toshiro Iwamoto, 16-4-308, Azuma 4-chome, Tsukuba-shi, Ibaraki 305; Akihiko Fujie, 41-1, Sakuragaokacho, Tsuchiura-shi, Ibaraki 300; Kumiko Nitta, 1160-4, Nagakuni, Tsuchiura-shi, Ibaraki 300; Yasuhisa Tsurumi, 21-1-510-601, Takezono, 3-chome; Nobuharu Shigematsu, 5-4-601, Umezono 2-chome, both of Tsukuba-shi, Ibaraki 305; Chiyoshi Kasahara, 2-2-13, Midorigaoka, Ikeda-shi, Osaka 563; Motohiro Hino, 13-3-1003, Touzaki-cho, Tsuchiura-shi, Ibaraki 300; Masakuni Okuhara, 14-10, Umezono 2-chome, Tsukuba-shi, Ibaraki 305, all of Japan

[21] Appl. No.: 311,434

[22] Filed: Sep. 26, 1994

Related U.S. Application Data

[63] Continuation of Ser. No. 791,926, Nov. 15, 1991, abandoned, which is a continuation-in-part of Ser. No. 614,125, Nov. 16, 1990, abandoned, which is a continuation-in-part of Ser. No. 610,759, Nov. 8, 1990, abandoned.

[30] Foreign Application Priority Data

| | | | |
|---|---|---|---|
| Dec. 14, 1990 | [GB] | United Kingdom | 9027152 |
| Jan. 24, 1991 | [GB] | United Kingdom | 9101552 |
| Apr. 2, 1991 | [GB] | United Kingdom | 9106822 |

[51] Int. Cl.[6] ..... A61K 38/00

[52] U.S. Cl. ..... 514/11; 514/9

[58] Field of Search ..... 514/11, 9, 17; 530/317, 329

[56] References Cited

U.S. PATENT DOCUMENTS

| | | | |
|---|---|---|---|
| 4,287,120 | 9/1981 | Abbott et al. | 530/317 |
| 4,320,052 | 3/1982 | Abbott et al. | 530/317 |
| 4,320,053 | 3/1982 | Abbott et al. | 530/317 |
| 4,322,338 | 3/1982 | Abbott et al. | 530/317 |
| 5,376,634 | 12/1994 | Iwamoto et al. | 530/317 |

FOREIGN PATENT DOCUMENTS

| | | |
|---|---|---|
| 0311193 | 12/1989 | European Pat. Off. . |
| 0359529 | 3/1990 | European Pat. Off. . |
| 0431350 | 6/1991 | European Pat. Off. . |
| 0448354 | 9/1991 | European Pat. Off. . |

OTHER PUBLICATIONS

Schmatz et al, *Proc. Natl. Acad. Sci.*, USA, vol. 87, pp. 5950–5954, 1990.

*Primary Examiner*—Charles T. Jordan
*Assistant Examiner*—Meena Chelliah

[57] ABSTRACT

A pharmaceutical composition comprising an amount of a polypeptide of the formula:

wherein $R^1$ is hydrogen or an acyl group, $R^2$ is hydroxy or an acyloxy group, $R^3$ is hydrogen, hydroxy or hydroxysulfonyloxy, $R^4$ is hydrogen or carbamoyl, and $R^5$ and $R^6$ are each hydrogen or hydroxy, with the proviso that (i) $R^2$ is acyloxy when $R^3$ is hydrogen, and (ii) $R^5$ is hydrogen when $R^6$ is hydrogen, or a pharmaceutically acceptable salt thereof, is useful in the prevention or treatment of *Pneumocystis carinii* infection.

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

USE OF THE POLYPEPTIDE COMPOUND

This application is a continuation of application Ser. No. 07/791,926, filed on Nov. 15, 1991, now abandoned, which is a continuation-in-part of application Ser. No. 07/614,125, filed Nov. 16, 1990, now abandoned, which is a continuation-in-part of application Ser. No. 07/610,759, filed Nov. 8, 1990, now abandoned.

The present invention relates to a new use of the polypeptide compound or a pharmaceutically acceptable salt thereof.

More particularly, it relates to the utility of the polypeptide compound for the prevention and/or the treatment of *Pneumocystis carinii* infection (e.g., *Pneumocystis carinii* pneumonia, etc.) in a human being or an animal.

SUMMARY OF THE INVENTION

Accordingly, one object of the present invention is to provide a pharmaceutical composition for the prevention and/or the treatment of *Pneumocystis carinii* infection (e.g. *Pneumocystis carinii* pneumonia, etc.) in a human being or an animal comprising, as an active ingredient, the polypeptide compound or a pharmaceutically acceptable salt thereof.

Another object of the present invention is to provide a method for the prevention and/or the treatment of *Pneumocystis carinii* infection (e.g. *Pneumocystis carinii* pneumonia, etc.) in a human being or an animal, which comprises administering the polypeptide compound to a human being or an animal.

A further object of the present invention is to provide a use of the polypeptide compound for the manufacture of a medicament for the prevention and/or the treatment of *Pneumocystis carinii* infection (e.g., *Pneumocystis carinii* pneumonia, etc.) in a human being or an animal.

The polypeptide compound used in the present invention is novel and can be represented by the following general formula [I] (SEQ ID NO: 1):

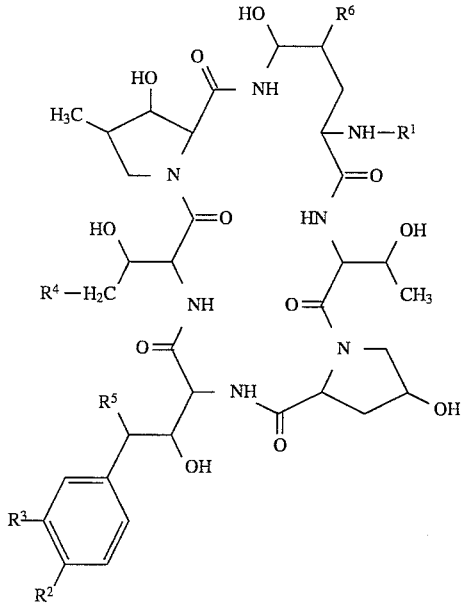

[I]

wherein $R^1$ is hydrogen or an acyl group, $R^2$ is hydroxy or an acyloxy group, $R^3$ is hydrogen, hydroxy or hydroxysulfonyloxy, $R^4$ is hydrogen or carbamoyl, and $R^5$ and $R^6$ are each hydrogen or hydroxy, with proviso that (i) $R^2$ is acyloxy when $R^3$ is hydrogen, and (ii) $R^5$ is hydrogen when $R^6$ is hydrogen.

The inventors of the present invention have found that the polypeptide compound of the formula [I] and pharmaceutically acceptable salts thereof are useful for the prevention and/or the treatment of *Pneumocystis carinii* infection (e.g., *Pneumocystis carinii* pneumonia, etc.) in a human being or an animal in need thereof. The polypeptide compound of the formula [I] and pharmaceutically acceptable salts thereof are also useful for the preparation of a medicament for the prevention and/or the treatment of *Pneumocystis carinii* infection (e.g., *Pneumocystis carinii* pneumonia, etc.).

The pharmaceutical composition of the present invention can be used in the form of a pharmaceutical preparation, for example, in solid, semisolid or liquid form, which contains the polypeptide compound [I] or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. If necessary or desired, additional auxiliary, stabilizing, thickening and coloring agents and perfumes may be used.

The polypeptide compound [I] and/or one or more pharmaceutically acceptable salt thereof is/are included in the pharmaceutical composition in an amount sufficient to produce the desired effect upon the process or condition of *Pneumocystis carinii* infection. Preferably, the amount of the polypeptide compound [I] and/or pharmaceutically acceptable salts thereof is sufficient either to effectively prevent infection by *Pneumocystis carinii* or to effectively treat a disease resulting from infection by *Pneumocystis carinii.*

The pharmaceutical composition of the present invention can be manufactured by the conventional methods in this field of the art. If necessary or desired, the techniques generally used in this field of the art for improving the bioavailability of a drug can be applied to the pharmaceutical composition of the present invention.

For administering the composition to a human being or an animal, preferable routes include intravenous, intramuscular, pulmonary, and oral administration, as well as insufflation.

While the dosage of therapeutically effective amount of the polypeptide compound [I] varies from and also depends upon the age and condition of each individual patient to be treated, in the case of intravenous administration, a daily dose of 0.01–100 mg of the polypeptide compound [I] per kg weight of a human being or an animal, preferably 0.1–50 mg/kg, particularly preferably 0.5–30 mg/kg; in the case of intramuscular administration, a daily dose of 0.1–100 mg of the polypeptide compound [I] per kg weight of a human being or an animal, preferably 0.5–80 mg/kg, particularly preferably 1.0–50 mg/kg; and in the case of oral administration, a daily dose of 0.5–100 mg of the polypeptide compound [I] per kg weight of a human being or an animal, preferably 1.0–100 mg/kg, particularly preferably 2.0–75 mg/kg, is generally given for the prevention and/or the treatment of *Pneumocystis carinii* infection (e.g., *Pneu-*

*mocystis carinii* pneumonia, etc.) in a human being or an animal.

Especially preferred routes are described hereinbelow.

For administration by inhalation, the compounds of the present invention are conveniently delivered in the form of an aerosol spray presentation from pressurized packs or nebulisers. The compounds may also be delivered as powders which may be conventionally formulated, and the powder compositions may be inhaled with the aid of an insufflation powder inhaler device. The preferred delivery system for inhalation is a metered dose inhalation aerosol, which may be formulated as a suspension or solution of compound in one or more suitable propellants, such as fluorocarbons or hydrocarbons.

Because of the desirability to directly treat lung and bronchi, aerosol administration is a preferred method of administration. Insufflation is also a desirable method, especially where infection may have spread to ears ahd other body cavities.

Alternatively, parenteral administration may be employed using drip intravenous administration.

In order to show the usefulness of the polypeptide compound [I] or a pharmaceutically acceptable salt thereof used in the present invention for the prevention and/or the treatment of *Pneumocystis carinii* infection (e.g., *Pneumocystis carinii* pneumonia, etc.) in a human being or an animal, the pharmacological test data of the representative compounds thereof are shown in the following tests.

Test 1

Eight Hooded nude rats (3 male, 5 female) were intranasally infected with $10^4$ *Pneumocystis carinii* cysts (derived from rat), and subcutaneously injected with 20 mg cortisone once a week for 8 weeks. At the start of the treatment with FR131535 substance, three of the 8 rats were sacrificed. The lungs were removed, homogenized with a glass homogenizer in phosphate buffered saline, and processed for quantification as described below. The remaining rats were divided into two groups, and the rats of one group were intraperitoneally injected once daily with 2 mg of FR131535 substance in 0.5 ml of saline and the rats of the other group were intraperitoneally injected once daily only with 0.5 ml of saline as a negative control.

The total number of cysts per rat lung was determined by quantifying the number of cysts of homogenized lung tissue on slides fixed with ether/sulfuric acid and stained with toluidine blue 0.

The test results were as follows.

| Treatment with | | Rat | Number of cysts per lung ($log_{10}$) |
|---|---|---|---|
| before | | 1 | 6.56 |
| treatment | | 2 | 6.53 |
| | | 3 | 6.30 |
| FR131535 | 10 mg[a] (5[b]) | 4 | 4.56 |
| substance | 12 mg[a] (6[b]) | 5 | 3.89 |
| | 26 mg[a] (13[b]) | 6 | 4.78 |
| saline | | 7 | 7.15 |
| | | 8 | 7.94 |

[a]Total amount of FR131535 substance given to rat

[b]the day after the start of treatment when the number of cysts in lung was determined

Test 2

1. Test Method

Sixty-three female BALB/C nu/nu mice, 5 weeks old, were intranasally infected with $10^4$ cysts per head under anesthesia, housed in sterilized vinyl isolators and fed under completely sterilized conditions.

Experiment I: Prophylactic effect

Fifty-two days after the infection (at this time, *Pneumocystis carinii* pneumonia had not yet occurred, judging from the conditions of the mice), 34 of the infected mice were randomly selected and used for the prophylactic experiment.

Five mice were sacrificed for determining the physical condition at the starting point.

One of the lungs from each mouse was removed, weighed, and preserved at −80° C. for examining the number of cysts in the lung. The number of cysts was determined by microscopically counting the number of cysts of homogenized lung tissue on a slide fixed with ether/sulfuric acid and stained with toluidine blue 0 (hereinafter, this procedure is referred to as "Protocol").

The remaining 29 mice were divided into three groups. Nine mice (Group 1) were subcutaneously injected with saline once a day except on Saturday and Sunday. Two groups of 10 mice were similarly treated with 10 mg/kg of FR 131535 substance (Group 2) and FR 901379 substance (Group 3), respectively.

Half of the mice of each group were sacrificed 18 days after the start of the administration (Point A) and examined by the "Protocol", and the remainder were similarly examined 56 days after the start of the administration (Point B).

Experiment II: Curative effect

The mice not used in Experiment I began to show typical symptoms of *Pneumocystis carinii* pneumonia, mainly wasting and cyanosis, about three months after the infection.

One hundred one days after the infection, the mice were divided into two groups, based on the degree of the symptoms (light symptoms: 17 mice, heavy symptoms: 14 mice). Each group was divided into four subgroups.

One subgroup (5 mice) out of each group of four subgroups was sacrificed for determining the status of mice at the start of therapy by the "Protocol".

Administration of the drugs was carried out in the same manner as Experiment I once a day except on Saturday and Sunday [heavy symptoms group: 3 mice for saline (Group 4), 3 mice for FR 131535 substance (Group 5) and 3 mice for FR 901379 substance (Group 6); light symptoms group: 4 mice for saline (Group 7), 4 mice for FR 131535 substance (Group 8) and 4 mice for FR 901379 substance (Group 9)).

The mice were treated for two weeks, then sacrificed at the end of the therapy for the examination of the number of the total cysts in the same manner as in the "Protocol".

2. Test Results

| Test Group | Total Cysts (mean $log_{10}$) |
|---|---|
| Experiment I | |
| at Point A | |
| Group 1 | 5.35 ± 0.26 |
| Group 2 | 1.76 ± 0.03*** |
| Group 3 | 1.81 ± 0.06*** |
| at Point B | |
| Group 1 | 6.34 ± 0.14 |
| Group 2 | 2.31 ± 0.26*** |

-continued

| Test Group | Total Cysts (mean $\log_{10}$) |
|---|---|
| Group 3 | 2.04 ± 0.25*** |
| Experiment II | |
| heavy symptoms | |
| Group 4 | 6.20 ± 0.08 |
| Group 5 | 2.06 ± 0.06*** |
| Group 6 | 3.10 ± 0.513*** |
| light symptoms | |
| Group 7 | 6.21 ± 0.12 |
| Group 8 | 3.85 ± 0.21*** |
| Group 9 | 3.23 ± 0.67*** |

***P<0.001

From the above test results, it turned out that the polypeptide compound [I] or a pharmaceutically acceptable salt thereof used in the present invention was very useful for the prevention and/or the treatment of *Pneumocystis carinii* pneumonia.

In the following, the polypeptide compound [I] or a pharmaceutically acceptable salt thereof used in the present invention is explained in detail.

The polypeptide compound or a salt thereof can be prepared by the processes as illustrated in the following schemes.

Process 1

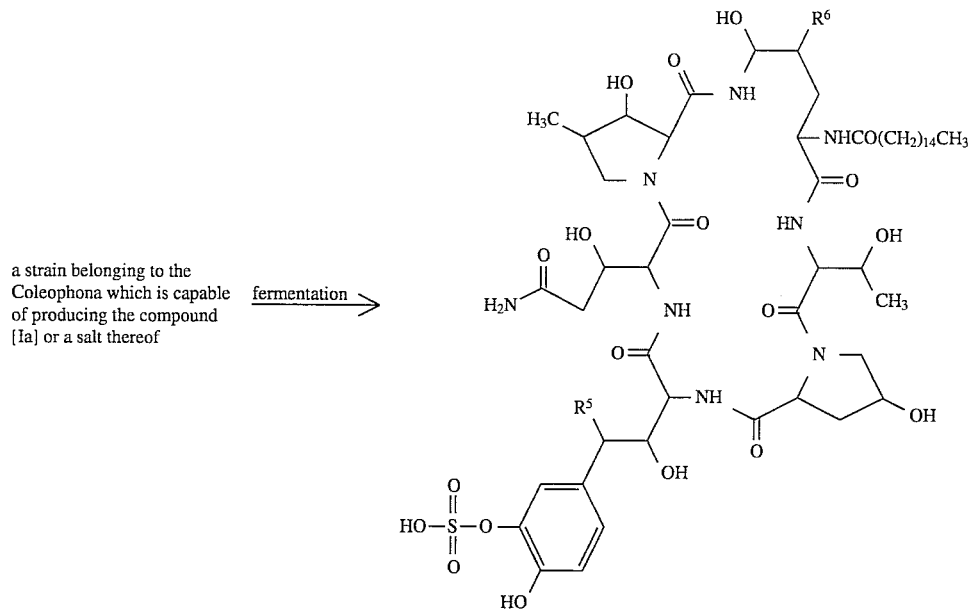

[Ia]
or a salt thereof

-continued
Process 2
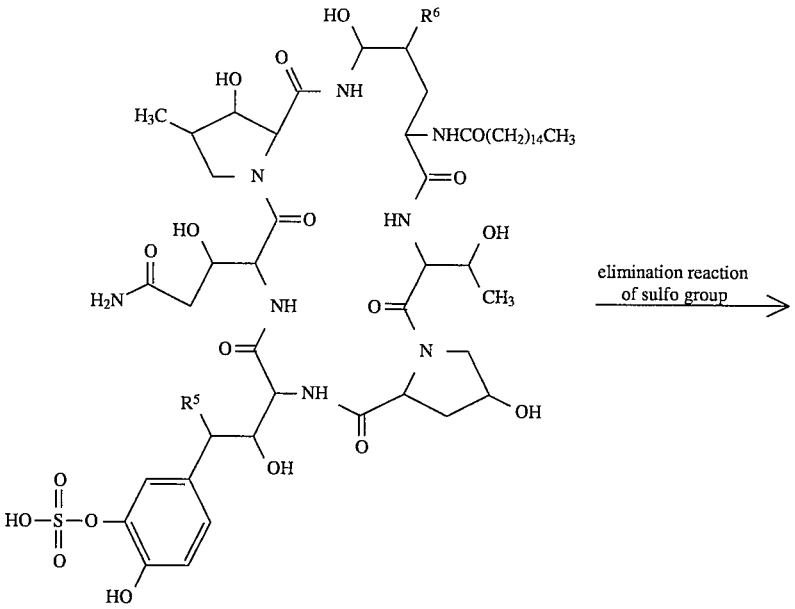
[Ia]
or a salt thereof
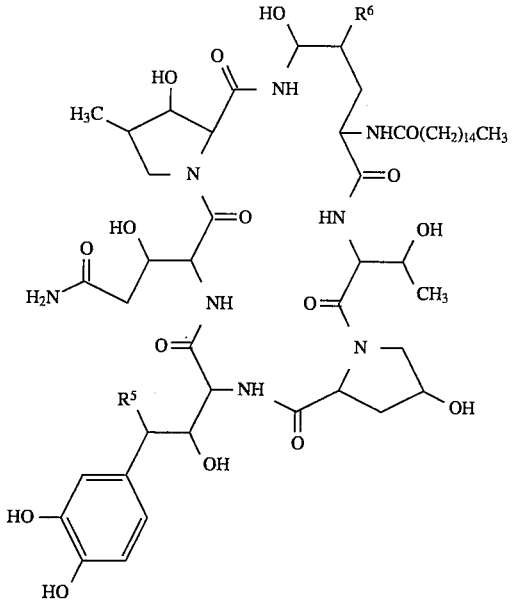
[Ib]
or a salt thereof -continued
Process 3
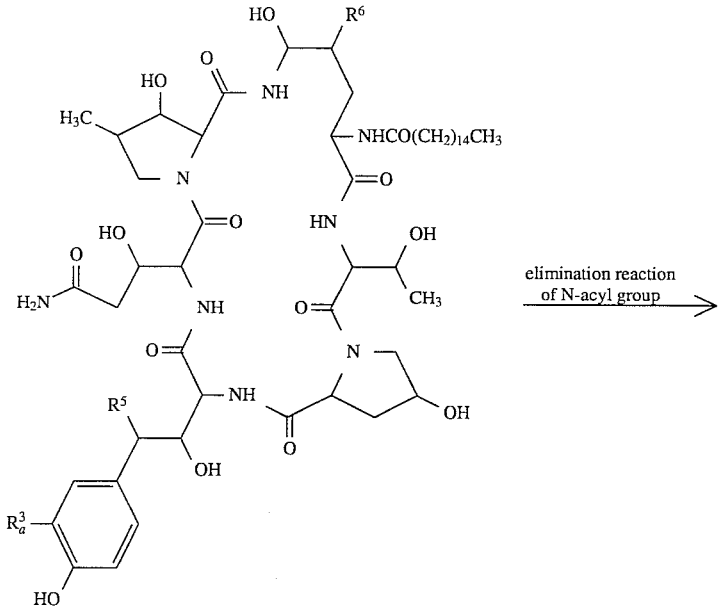
[Ic]
or a salt thereof
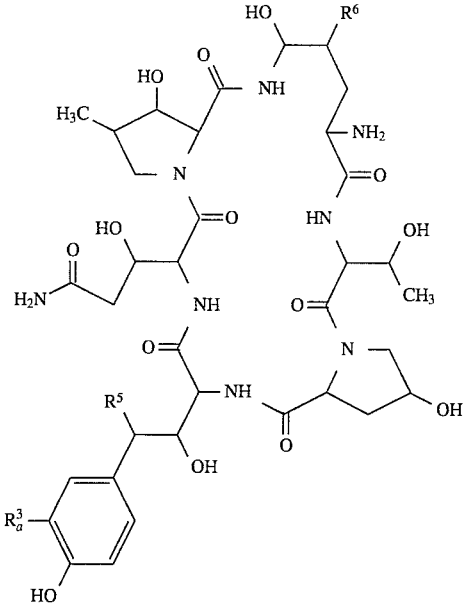
[Id]
or a salt thereof -continued
Process 4
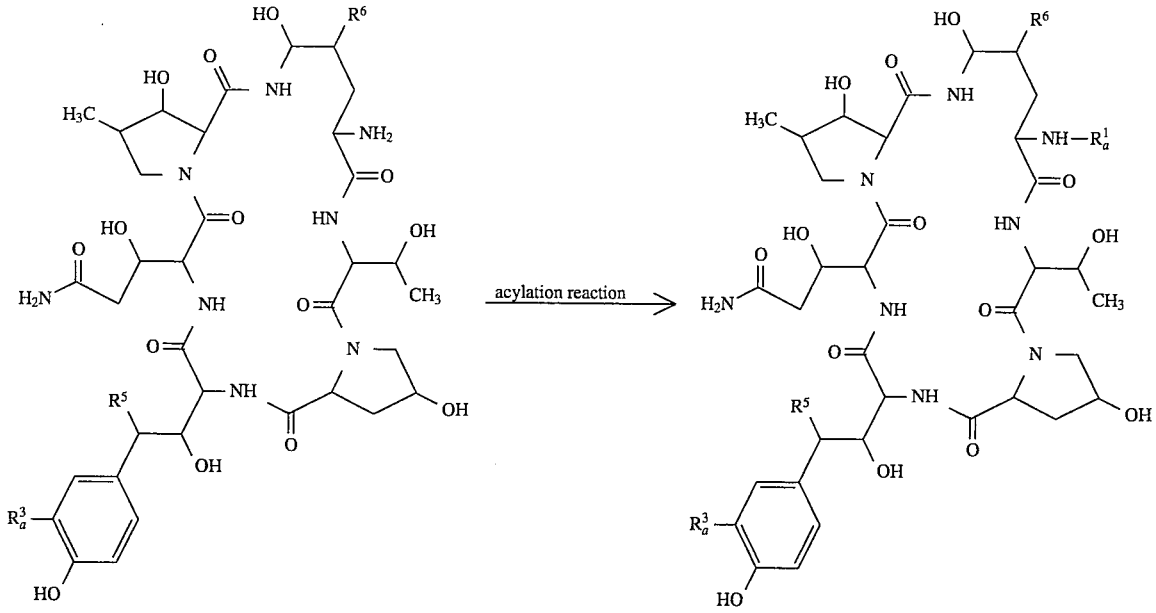
[Id]
or a salt thereof
[Ie]
or a salt thereof
Process 5
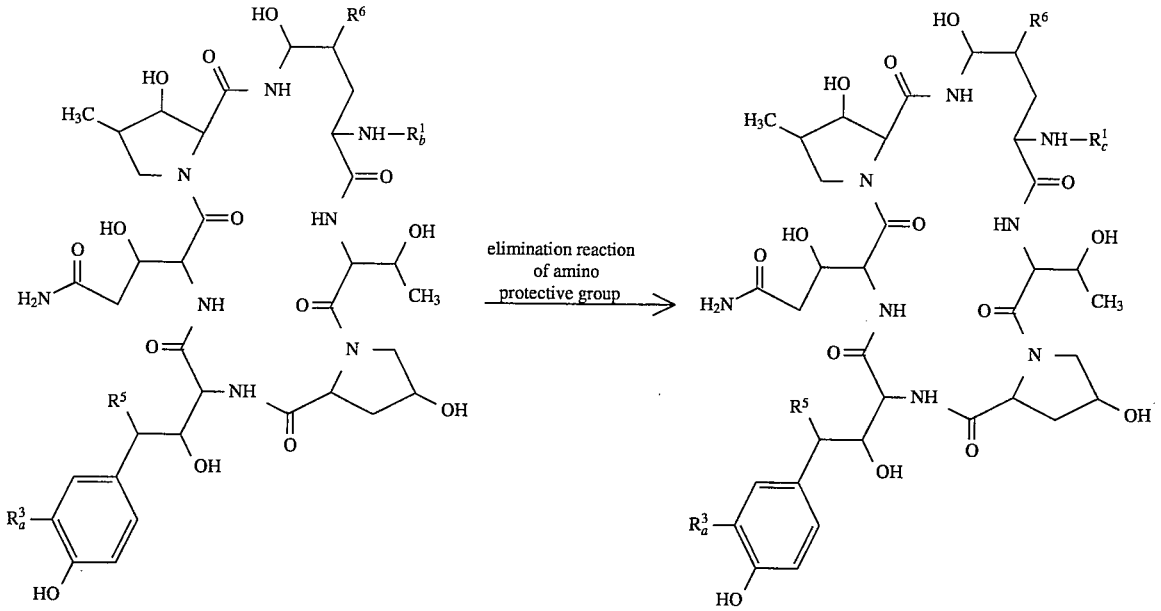
[If]
or a salt thereof
[Ig]
or a salt thereof -continued Process 6

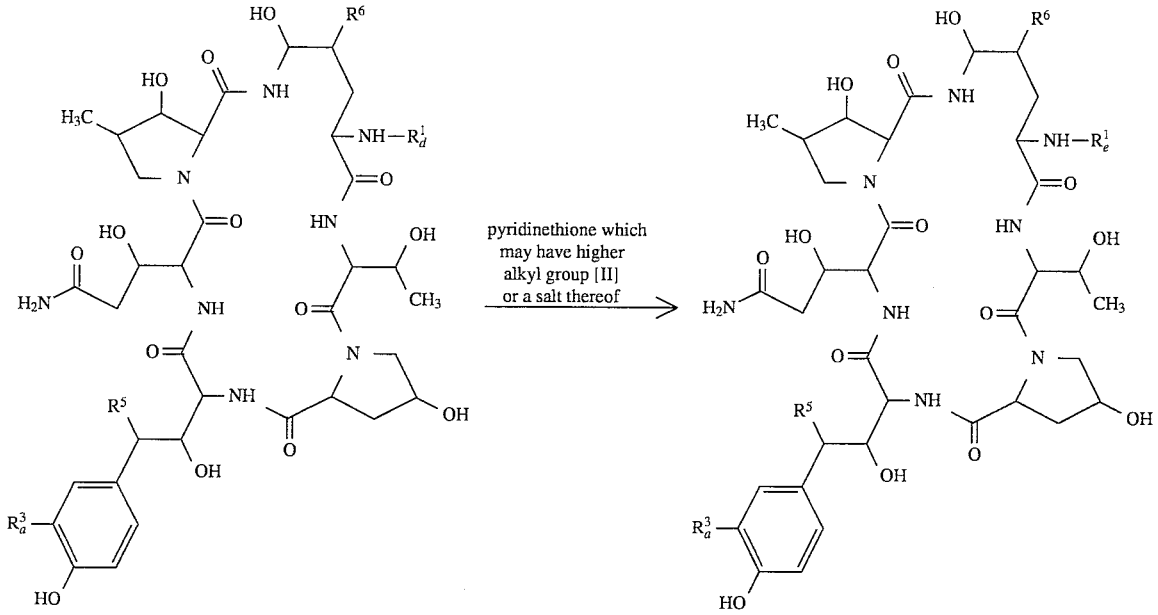

[Ih] or a salt thereof

[Ii] or a salt thereof

Process 7

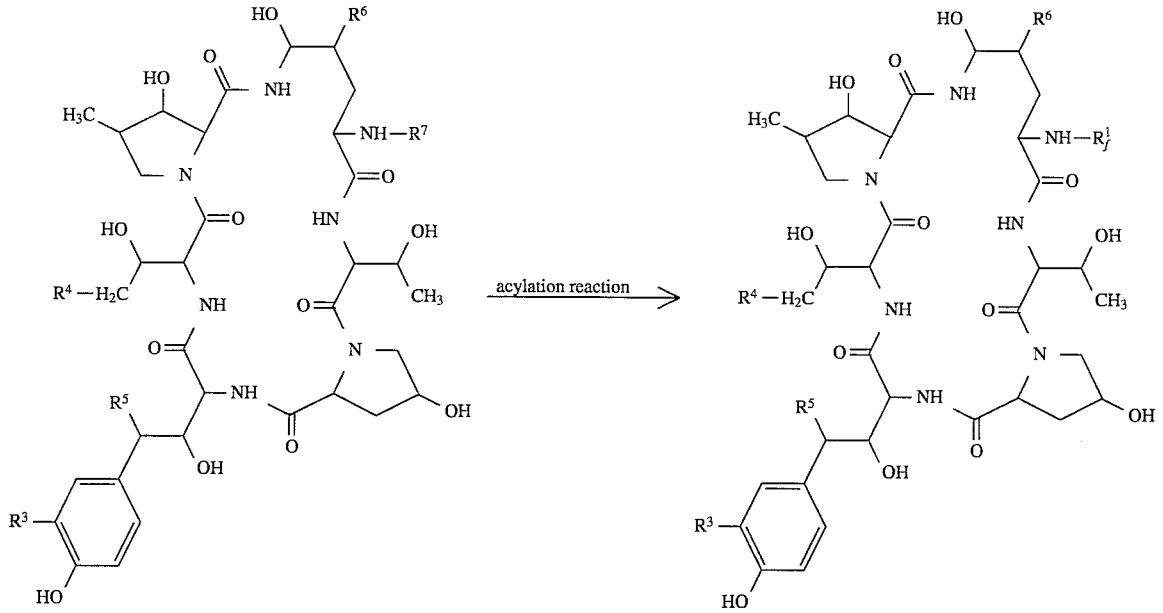

[III] or a salt thereof

[Ia] or a salt thereof wherein $R^3$, $R^4$, $R^5$ and $R^6$ are each defined above, $R_a^1$ is an acyl group, $R_b^1$ is an ar(lower)alkanoyl which has one or more higher alkoxy group(s) and a protected amino group, $R_c^1$ is an ar(lower)alkanoyl which has one or more higher alkoxy group(s) and an amino group, $R_d^1$ is halo(lower)alkanoyl $R_e^1$ is pyridylthio(lower)alkanoyl which may have one or more higher alkyl group(s), $R_f^1$ is acyloxy, $R_a^1$ is an acyl group, $R^7$ is an acyl group, and $R_a^3$ is hydroxy or hydroxysulfonyloxy Some of the starting compounds [III] (SEQ ID NO: 1) are novel and can be prepared according to the aforesaid Processes 3 to 6.

Suitable pharmaceutically acceptable salts of the object compound [I] are conventional non-toxic mono- or di-salts, and include metal salts such as alkali metal salts [e.g., sodium salt, potassium salt, etc.], alkaline earth metal salts [e.g., calcium salt, magnesium salt, etc.], ammonium salt(s), organic base salts [e.g., trimethylammonium salt, triethylammonium salt, pyridinium salt, picolinium salt, dicyclohexylammonium salt, N,N-dibenzylethylenediammonium salt, etc.], organic acid addition salts [e.g., formate, acetate, trifluroacetate, maleate, tartrate, methanesulfonate, benzenesulfonate, and/or toluenesulfonate salts, etc.], inorganic acid addition salts [e.g., hydrochloride, hydrobromide, hydroiodide, sulfate, phosphate, etc.], a salt with one or more amino acids [e.g., arginine salt, aspartic acid salt, glutamic acid salt, etc.], and the like.

In the above and subsequent description of this specification, suitable examples of the various definitions are explained in detail as follows:

The term "lower" is intended to mean 1 to 6 carbon atom(s), unless otherwise indicated.

The term "higher" is intended to mean 7 to 20 carbon atoms, unless otherwise indicated.

A suitable "acyl group" may be an aliphatic acyl, aromatic acyl, heterocyclic acyl, arylaliphatic acyl and heterocyclic-aliphatic acyl derived from a carboxylic acid, carbonic acid, carbamic acid, sulfonic acid, and the like.

Suitable example of the "acyl group" thus explained include:

lower alkanoyl [e.g., formyl, acetyl, propionyl, butyryl, isobutyryl, valeryl, hexanoyl, pivaloyl, etc.] which may have one or more (preferably 1 to 3) suitable substituent(s) such as halogen (e.g., fluoro, chloro, bromo, iodo); aryl (e.g. phenyl, naphthyl, anthryl, etc.) which may have one or more (preferably 1 to 3) suitable substituent(s) like hydroxy, higher alkoxy as explained below, aforesaid aryl, or the like; lower alkoxy as explained below; amino; protected amino, preferably acylamino, such as lower alkoxycarbonylamino (e.g., methoxycarbonylamino, ethoxycarbonylamino, propoxycarbonylamino, butoxycarbonylamino, t-butoxycarbonylamino, pentyloxycarbonylamino, hexyloxycarbonylamino, etc.), or the like; di(lower)alkylamino (e.g., dimethylamino, N-methylethylamino, diethylamino, N-propylbutylamino, dipentylamino, dihexylamino, etc.); lower alkoxyimino (e.g., methoxyimino, ethoxyimino, propoxyimino, butoxyimino, t-butoxyimino, pentyloxyimino, hexyloxyimino, etc.); ar(lower)alkoxyimino such as phenyl(lower)alkoxyimino (e.g., benzyloxyimino, phenethyloxyimino, benzhydryloxyimino, etc.) which may have one or more (preferably 1 to 3) suitable substituent(s) like higher alkoxy as explained below, or the like; heterocyclicthio, preferably pyridylthio, which may have one or more (preferably 1 to 3) suitable substituent(s) like higher alkyl (e.g., heptyl, octyl, 2-ethylhexyl, nonyl, decyl, 3,7-dimethyloctyl, undecyl, dodecyl, tridecyl, tetradecyl, pentadecyl, 3-methyl-10-ethyldodecyl, hexadecyl, heptadecyl, octadecyl, nonadecyl, eicosyl, etc.), or the like; heterocyclic group (e.g., thienyl, imidazolyl, pyrazolyl, furyl, tetrazolyl, thiazolyl, thiadiazolyl, etc.) which may have one or more (preferably 1 to 3) suitable substituent(s) like amino, aforesaid protected amino, aforesaid higher alkyl, or the like; or the like;

higher alkanoyl [e.g., heptanoyl, octanoyl, nonanoyl, decanoyl, undecanoyl, lauroyl, tridecanoyl, myristoyl, pentadecanoyl, palmitoyl, 10,12-dimethyltetradecanoyl, heptadecanoyl, stearoyl, nonadecanoyl, eicosanoyl, etc.];

lower alkenoyl [e.g., acryloyl, methacryloyl, crotonoyl, 3-pentenoyl, 5-hexenoyl, etc.] which may have one or more (preferably 1 to 3) suitable substituent(s) such as aforesaid aryl which may have one or more (preferably 1 to 3) suitable substituent(s) like higher alkoxy as explained below, or the like; or the like;

higher alkenoyl [e.g., 4-heptenoyl, 3-octenoyl, 3,6-decadienoyl, 3,7,11-trimethyl-2,6,10-dodecatrienoyl, 4,10-heptadecadienoyl, etc.];

lower alkoxycarbonyl [e.g., methoxycarbonyl, ethoxycarbonyl, propoxycarbonyl, butoxycarbonyl, t-butoxycarbonyl, pentyloxycarbonyl, hexyloxycarbonyl, etc.];

higher alkoxycarbonyl [e.g., heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, eicosyloxycarbonyl, etc.];

aryloxycarbonyl [e.g., phenoxycarbonyl, naphthyloxycarbonyl, etc.];

arylglyoxyloyl [e.g., phenylglyoxyloyl, naphthylglyoxyloyl, etc.];

ar(lower)alkoxycarbonyl which may have one or more suitable substituent(s) such as phenyl(lower)alkoxycarbonyl which may have a nitro or lower alkoxy group [e.g., benzyloxycarbonyl, phenethyloxycarbonyl, p-nitrobenzyloxycarbonyl, p-methoxybenzyloxycarbonyl, etc.];

lower alkylsulfonyl [e.g., methylsulfonyl, ethylsulfonyl, propylsulfonyl, isopropylsulfonyl, pentylsulfonyl, butylsulfonyl, etc.];

arylsulfonyl [e.g., phenylsulfonyl, naphthylsulfonyl etc.] which may have one or more (preferably 1 to 3) suitable substituent(s) such as lower alkyl as explained below, higher alkoxy as explained below, or the like;

ar(lower)alkylsulfony such as phenyl(lower)alkylsulfonyl [e.g., benzylsulfonyl, phenethylsulfony, benzhydrylsulfonyl, etc.], or the like; and aroyl [e.g., benzoyl, naphthoyl, anthrylcarbonyl, etc.] which may have one or more (preferably 1 to 5) suitable substituent(s) such as aforesaid halogen; lower alkyl (e.g., methyl, ethyl, propyl, butyl, t-butyl, pentyl, hexyl, etc.); aforesaid higher alkyl; lower alkoxy (e.g., methoxy, ethoxy, propoxy, butoxy, t-butoxy, pentyloxy hexyloxy, etc.) which may have one or more (preferably 1 to 10) suitable substituent(s) like aforesaid lower alkoxy, aforesaid halogen, aforesaid aryl, or the like; higher alkoxy (e.g., heptyloxy, octyloxy, 2-ethylhexyloxy, nonyloxy, decyloxy, 3,7-dimethyloctyloxy, undecyloxy, dodecyloxy, tridecyloxy, tetradecyloxy, pentadecyloxy, 3-methyl-10-ethyldodecyloxy, hexadecyloxy, heptadecyloxy, octadecyloxy, nonadecyloxy, eicosyloxy, etc.) which may have one or more (preferably 1 to 17) suitable substituent(s) like aforesaid halogen; higher alkenyloxy (e.g., 3-heptenyloxy, 7-octenyloxy, 2,6-octadienyloxy, 5-nonenyloxy, 1-decenyloxy, 3,7-dimethyl-6-octenyloxy, 3,7-dimethyl-2,6-octadienyloxy, 8-undecenyloxy, 3,6,8-dodecatrienyloxy, 5-tridecenyloxy, 7-tetradecenyloxy, 1,8-pentadecadienyloxy, 15-hexadecenyloxy, 11-heptadecenyloxy, 7-octadecenyloxy, 10-nonadecenyloxy, 18-eicosenyloxy, etc.); carboxy; aforesaid aryl which may have one or more (preferably 1 to 3) suitable substituent(s) like aforesaid higher alkoxy; aryloxy (e.g. phenoxy, naphthyloxy, anthryloxy, etc.) which may have one or more (preferably 1 to 3) suitable substituent(s) like aforesaid lower alkoxy, or aforesaid higher alkoxy; or the like; or the like.

Preferred "acyl groups" include:

lower alkanoyl or halo(lower)alkanoyl;

ar(lower)alkanoyl which may have one or more (preferably 1 to 3) suitable substituent(s) such as hydroxy, lower alkoxy, higher alkoxy, aryl, amino, protected amino, di(lower)alkylamino, lower alkoxyimino or ar(lower)alkoxyimino which may have one or more (preferably 1 to 3) higher alkoxy group(s);

heterocyclicthio(lower)alkanoyl which may have one or more (preferably 1 to 3) higher alkyl group(s);

heterocyclic(lower)alkanoyl which may have one or more (preferably 1 to 3) suitable substituent(s) such as lower alkoxyimino, higher alkyl, amino or protected amino;

ar(lower)alkoxyimino(lower)alkanoyl which may have one or more (preferably 1 to 3) higher alkoxy group(s);

higher alkanoyl;

ar(lower)alkenoyl which may have one or more (preferably 1 to 3) higher alkoxy group(s);

higher alkenoyl; lower alkoxycarbonyl; higher alkoxycarbonyl; aryloxycarbonyl;

arylsulfonyl which may have one or more (preferably 1 to 3) substituent(s) such as lower alkyl or higher alkoxy; and aroyl which may have one or more (preferably 1 to 5) suitable substituent(s) such as halogen, lower alkyl, higher alkyl, carboxy, lower alkoxy which may have one or more (preferaby 1 to 10) halogen atom(s), lower alkoxy(lower)alkoxy, ar(lower)alkoxy, higher alkoxy which may have one or more (preferably 1 to 17) halogen atom(s), higher alkenyloxy, aryl which may have one or more (preferably 1 to 3) higher alkoxy group(s) or aryloxy which may have one or more (preferably 1 to 3) substituent(s) such as lower alkoxy or higher alkoxy.

The more preferred acyl group include lower alkanoyl; halo(lower)alkanoyl;

phenyl(lower)alkanoyl or naphthyl(lower)alkanoyl, each of which may have 1 to 3 substituents such as hydroxy, lower alkoxy, higher alkoxy, phenyl, amino, lower alkoxycarbonylamino, di(lower)alkylamino, lower alkoxyimino, or phenyl(lower)alkoxyimino which may have 1 to 3 higher alkoxy group(s);

pyridylthio(lower)alkanoyl which may have 1 to 3 higher alkyl group(s);

imidazolyl(lower)alkanoyl or thiazolyl(lower)alkanoyl, each of which may have 1 to 3 suitable substituents such as lower alkoxyimino, higher alkyl, amino or lower alkoxycarbonylamino;

phenyl(lower)alkoxyimino(lower)alkanoyl which may have 1 to 3 higher alkoxy group(s);

higher alkanoyl;

phenyl(lower)alkenoyl which may have 1 to 3 higher alkoxy group(s);

higher alkenoyl; lower alkoxycarbonyl, higher alkoxycarbonyl; phenoxycarbonyl;

phenylsulfonyl or naphthylsulfonyl, each of which may have 1 to 3 lower alkyl or higher alkoxy group(s); and benzoyl, naphthoyl or anthrylcarbonyl, each of which may have 1 to 5 suitable substituents such as halogen, lower alkyl, higher alkyl, carboxy, lower alkoxy which may have 6 to 10 halogen atoms, lower alkoxy(lower)-alkoxy, phenyl(lower)alkoxy, higher alkoxy which may have 12 to 17 halogen atom(s), higher alkenyloxy, phenyl which may have 1 to 3 higher alkoxy group(s), phenoxy which may have 1 to 3 lower alkoxy or higher alkoxy group(s).

The much more preferred acyl groups include:

$(C_1-C_4)$alkanoyl; halo$(C_1-C_4)$alkanoyl;

phenyl$(C_1-C_4)$alkanoyl which may have 1 to 3 suitable substituent (s) such as hydroxy, $(C_1-C_4)$alkoxy, $(C_7-C_{16})$alkoxy, phenyl, amino, $(C_1-C_4)$alkoxycarbonylamino, di$(C_1-C_4)$alkylamino, $(C_1-C_4)$alkoxyimino or phenyl$(C_1-C_4)$alkoxyimino which may have a $(C_7-C_{16})$alkoxy group;

naphthyl$(C_1-C_4)$alkanoyl which may have 1 to 3 $(C_1-C_4)$alkoxycarbonylamino groups;

1-$(C_7-C_{16})$alkylpyridiniothio$(C_1-C_4)$alkanoyl;

imidazolyl$(C_1-C_4)$alkanoyl which may have 1 to 3 $(C_7-C_{16})$alkyl or $(C_1-C_4)$alkoxycarbonylamino group(s);

thiazolyl$(C_1-C_4)$alkanoyl which may have 1 to 3 $(C_1-C_4)$alkoxyimino or amino group(s);

phenyl $(C_1-C_4)$alkoxyimino$(C_1-C_4)$ alkanoyl which may have 1 to 3 $(C_7-C_{16})$alkoxy group(s);

$(C_7-C_{17})$alkyl;

phenyl$(C_1-C_4)$alkenoyl which may have 1 to 3 $(C_7-C_{16})$alkoxy group(s);

$(C_7-C_{18})$alkenoyl; $(C_3-C_6)$alkoxycarbonyl;

$(C_7-C_{16})$alkoxycarbonyl; phenoxycarbonyl;

phenylsulfonyl which may have a $(C_1-C_4)$alkyl or $(C_7-C_{16})$alkoxy group;

naphthylsulfonyl which may have a $(C_7-C_{16})$alkoxy group;

benzoyl which may have 1 to 5 suitable substituent(s) such as halogen, $(C_3-C_6)$alkyl, $(C_7-C_{16})$alkyl, carboxy, $(C_1-C_6)$alkoxy which may have 6 to 10 halogen atoms, $(C_1-C_4)$alkoxy$(C_1-C_4)$alkoxy, phenyl$(C_3-C_6)$alkoxy, $(C_7-C_{16})$alkoxy which may have 12 to 17 halogen atoms, phenyl which may have 1 to 3 $(C_7-C_{16})$alkoxy group(s) or phenoxy which may have 1 to 3 $(C_3-C_6)$alkoxy or $(C_7-C_{16})$alkoxy group(s);

naphthoyl which may have 1 to 3 suitable substituent(s) such as $(C_3-C_6)$alkoxy, $(C_7-C_{16})$alkoxy or $(C_7-C_{16})$alkenyloxy; and anthrylcarbonyl.

The most preferred acyl groups are acetyl, 2-bromoacetyl, 2-(4-biphenylyl)acetyl, 2-(4-octyloxyphenyl)acetyl, 3-(4-octyloxyphenyl)propionyl, 2-amino-2-(4-octyloxyphenyl)acetyl, 2-(t-butoxycarbonylamino)-2-(4-octyloxyphenyl)acetyl, 2-amino-3-(4-octyloxyphenyl)propionyl, 2-(t-butoxycarbonylamino)-3-(4-octyloxyphenyl)propionyl, 2-dimethylamino-3-(4-octyloxyphenyl)propionyl, 2-(t-butoxycarbonylamino)-2-(2-naphthyl)acetyl, 2-methoxy-2-(4-octyloxyphenyl)acetyl, 2-methoxyimino-2-(4-octyloxyphenyl)acetyl, 2-(4-octyloxybenzyloxyimino)-2-(4-hydroxyphenyl)acetyl, 2-(4-octyloxybenzyloxyimino)-2-phenylacetyl, 2-(4-octyloxybenzyloxyimino)acetyl, 2-(1-octyl-4-pyridinio)thioacetyl, 2-methoxyimino-2-(2-aminothiazol-4-yl)acetyl, 2-(t-butoxycarbonylamino)-3-(1-octyl-4-imidazolyl)propionyl, 3-(4-octyloxyphenyl)acryloyl, 3,7,11-trimethyl-2,6,10-dodecatrienoyl, t-butoxycarbonyl, octyloxycarbonyl, phenoxycarbonyl, p-tolylsulfonyl, 4-octyloxyphenylsulfonyl, 6-octyloxy-2-naphthylsulfonyl, 4-(t-butyl)benzoyl, 4-octylbenzoyl, 2,3,5,6-tetrafluoro-4-(2,2,3,3,4,4,5,5-octafluoropentyloxy)benzoyl, 4-(2-butoxyethoxy)benzoyl, 4-(4-phenylbutoxy)benzoyl, 4-octyloxybenzoyl, 2-carboxy-4-octyloxybenzoyl, 3-methoxy-4-octyloxybenzoyl, 4-(2,2,3,3,4,4,5,5,6,6,7,7,8,8,8-pentadecafluorooctyloxy)-2,3,5,6-tetrafluorobenzoyl, 4-(4-octyloxyphenyl)benzoyl, 4-(4-octyloxyphenoxy)benzoyl, 6-butoxy-2-naphthoyl, 6-hexyloxy-2-naphthoyl, 6-octyloxy-2-naphthoyl, 6-(2-ethylhexyloxy)-2-naphthoyl, 6-decyloxy-2-naphthoyl, 6-(3,7-dimethyloctyloxy)-2-naphthoyl, 6-dodecyloxy-2-naphthoyl, 6-(3,7-dimethyl-6-octenyloxy)-2-naphthoyl, 6-(3,7-dimethyl-2,6-octadienyloxy)-2-naphthoyl, 2-anthrylcarbonyl, 4-(4-heptyloxyphenyl)benzoyl and 4-(4-hexyloxyphenoxy)-benzoyl.

Suitable "ar(lower)alkanoyl" moieties in the groups "ar(lower)alkanoyl which has higher alkoxy and protected amino" and "ar(lower)alkanoyl which has higher alkoxy and amino" are selected from those described above for "acyl group", and suitable examples of the substituent(s) "higher alkoxy" and "protected amino" are also selected from those described above for "acyl group".

Suitable "halo(lower)alkanoyl" are selected from those described above for "acyl group".

Suitable "pyridylthio(lower)alkanoyl" in "pyridylthio(lower)alkanoyl which may have higher alkyl" are chosen from the ones as exemplified above for "acyl group", and suitable examples of the substituent "higher alkyl" are chosen from those exemplified above for "acyl group".

Suitable "acyloxy" may include hydroxysulfonyloxy, phosphonooxy, and the like.

In the object compound [I] thus defined, the following compound [Ik] (SEQ ID NO: 1) is especially preferable:

[Ik]

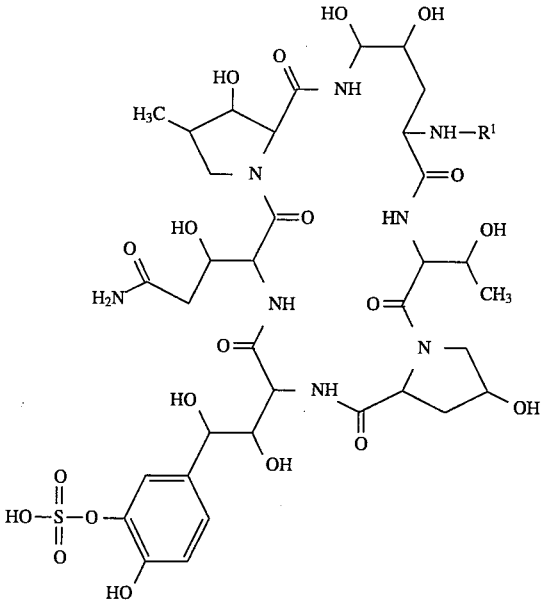

wherein $R^1$ is hydrogen or an acyl group.

A suitable "acylating agent" for the acylation reaction in Process 4 may be an acid compound corresponding to the acyl group to be introduced, or a salt thereof, or its reactive derivative at the carbon group. A suitable example of said acylating agent is represented by the formula:

$$R_a^1—OH \qquad [V]$$

wherein $R_a^1$ is as defined above, or a salt thereof, or its reactive derivative at the carboxy group:

Suitable reactive derivatives of the "acylating agent" above include acid halides, such as an acid chloride, acid anhydrides, which may be symmetrical or unsymmetrical, or may be another known reactive derivative. The phrase "reactive derivative at the carboxy group" means a reactive moiety in place of the —OH group in formula [IV] above, which will facilitate the reaction of acylating agent with the primary amino group of the compound of formula [Id].

In the compound [V], the following compounds are novel:

[V-1]

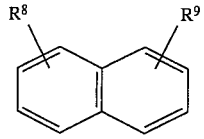

or its reactive derivative
at the carboxy group,
or a salt thereof,

[V-2]

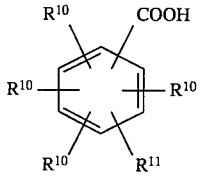

or its reactive derivative
at the carboxy group,
or a salt thereof, wherein $R^8$ is lower alkoxy, higher alkoxy or higher alkenyloxy, $R^9$ is —COOH or —$SO_3H$, $R_{10}$ is hydrogen or halogen, $R_{11}$ is lower alkoxy which has one or more halogen atoms, or higher alkoxy which has one or more halogen atoms, wherein the maximum number of halogen atoms is represented by a perhalogenated substituent.

The compounds [V-1] and [V-2] can be prepared by the following processes:

Process A

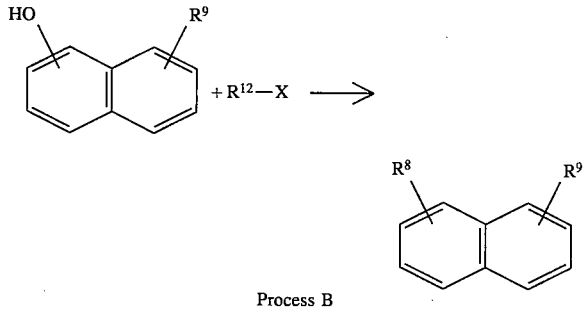

Process B

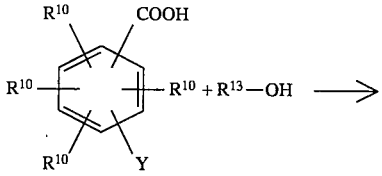

-continued

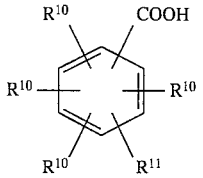

wherein $R^8$, $R^9$, $R^{10}$ and $R^{11}$ are each as defined above, $R^{12}$ is lower alkyl, higher alkyl or higher alkenyl, $R^{13}$ is lower alkyl which has one or more halogen atom(s) or higher alkyl which has one or more halogen atom(s), and X and Y are each a leaving group.

In the above definitions, suitable "lower alkoxy", "higher alkoxy""higher alkenyloxy", "halogen", "lower alkyl" and "higher alkyl" are defined as described and exemplified above.

Suitable "higher alkenyl" groups may include 3-heptenyl, 7-octenyl, 2,6-octadienyl, 5-nonenyl, 1-decenyl, 3,7-dimethyl-6-octenyl, 3,7-dimethyl-2,6-octadienyl, 8-undecenyl, 3,6,8-dodecatrienyl, 5-tridecenyl, 7-tetradecenyl, 1,8-pentadecadienyl, 15-hexadecenyl, 11-heptadecenyl, 7-octadecenyl, 10-nonadecenyl, 18-eicosenyl and the like. The preferred higher alkenyl group is a $(C_7–C_{16})$alkenyl group.

As for $R^{11}$, "lower alkoxy" has one or more (preferably 1 to 10, more preferably 6 to 10) halogen atom(s), and "higher alkoxy" has one or more (preferably 1 to 17, more preferably 12 to 17) halogen atom(s).

As for $R^{13}$, "lower alkyl" has one or more (preferably 1 to 10, more preferably 6 to 10) halogen atom(s), and "higher alkyl" has one or more (preferably 1 to 17, more preferably 12 to 17) halogen atom(s).

As for $R^8$, the preferred "lower alkoxy" is $(C_4–C_6)$alkoxy.

A suitable "leaving group" includes aforesaid halogen, lower alkanoyloxy (e.g., acetoxy, etc.), sulfonyloxy (e.g., mesyloxy, toxyloxy, etc.), and the like.

Suitable salts and reactive derivatives at the carboxy group of the compounds [V-1] and [V-2] include those described above and the ones exemplified below for the compound [V].

The reactions in Processes A and B can be carried out according to the methods disclosed later in Preparations of the present specification, or known methods similar thereto.

For the compounds of the formula [V], there are other novel compounds than those of the formulae [V-1] and [V-2], and they can be prepared, for example, by the methods disclosed later in Preparations.

A suitable "pyridinethione" in Process 6 may include 1,2-dihydropyridine-2-thione, 1,4-dihydropyridine-4-thione, or the like, and said "pyridinethione" may have a "higher alkyl" group as described above.

The processes for preparing the object compound [I] of the present invention or a salt thereof are explained in detail in the following Process and Preparations.

Process 1

The object compound [Ia] (SEQ ID NO: 1) or a salt thereof can be prepared by a fermentation process.

The fermentation process is explained in detail hereinbelow.

The compound [Ia] of the present invention or a salt thereof can be produced by fermentation of a strain belonging to the genus Coleophoma, such as Coleophoma sp. F-11899, which produces the compound [Ia] or a salt thereof in a nutrient medium.

(i) Microorganism:

Particulars of the microorganism used for producing the compound [Ia] or a salt thereof is explained hereinbelow.

The strain F-11899 was originally isolated from a soil sample collected at Iwaki-shi, Fukushima-ken, Japan. This organism grew rather restrictedly on various culture media, and formed dark grey to brownish grey colonies. An anamorph (conidiomata) was produced on a steam-sterilized leaf segment affixed on a Miura's LCA plate (Miura, K. and Kudo, M. Y.: An agar-medium for aquatic Hyphomycetes. *Trans. Ycolo. Soc. Japan,* 11:116–118, 1970), and on a corn meal agar plate by inoculating the isolate, while neither a teleomorph nor an anamorph formed on agar media alone. Its morphological, cultural and physiological characteristics are as follows.

Cultural characteristics on various agar media are summarized in Table 1. Cultures on potato dextrose agar grew rather rapidly, attaining 3.5–4.0 cm in diameter after two weeks at 25° C. This colony surface was planar, felty, somewhat wrinkly and brownish grey. The colony center was pale grey to brownish grey, and covered with aerial hyphae. The reverse color was dark grey. Colonies on malt extract agar grew more restrictedly, attaining 2.5–3.0 cm in diameter under the same conditions. The surface was planar, thin to felty and olive brown. The colony center was yellowish grey, and covered with aerial hyphae. The reverse was brownish grey.

The morphological characteristics were determined on basis of the cultures on a sterilized leaf affixed to a Miura's LCA plate. Conidiomata formed on the leaf segment alone. They were pycnidial, superficial, separate, discoid to ampulliform, flattened at the base, unilocular, thin-walled, black, 90–160(–200) μm in diameter and 40–70 μm high. Ostiole was often single, circular, central, papillate, 10–30 μm in diameter and 10–20 μm high. Conidiophores formed from the lower layer of inner pycnidial walls. They were hyaline, simple or sparingly branched, septate and smooth. Conidiogenous cells were enteroblastic, phialidic, determinate, ampulliform to obpyriform, hyaline, smooth, 5–8 x 4–6 μm, with a collarette. The collarettes were campanulate to cylindrical, and 14–18×3–5 μm. Conidia were hyaline, cylindrical, thin-walled, aseptate, smooth and 14–16(–18)×2–3 μm.

The vegetative hyphae were septate, brown, smooth and branched. The hyphal cells were cylindrical and 2–7 μm thick. The chlamydospores were absent.

The strain F-11899 had a temperature range for growth of 0°to 31° C. and an optimum temperature of 23° to 27° C. an potato dextrose agar.

The above characteristics indicate that the strain F-11899 belongs to the order Coelomycetes (von Arx, J. A.: "The Genera of Fungi—Sporulating in Pure Culture," 3rd ed ., J. Cramer, ed., Vaduz, 1974; Sutton, B. C.: "The Coelomycetes—Fungi Imperfecti with Pycnidia, Acervuli and Stromata," Commonwealth Mycological Institute, Kew, 1980; Hawksworth, D. L., Sutton, B. C., and Ainsworth, G. C.: "Dictionary of the Fungi," 7th ed. Commonwealth Mycological Institute, Kew, 1983). Thus, we named the strain "Coelomycetes strain F-11899".

TABLE 1

Cultural characteristics of the strain F-11899

| Medium | | Cultural characteristics |
|---|---|---|
| Malt extract agar (Blakeslee 1915) | G: | Rather restrictedly, 2.5–3.0 cm |
| | S: | Circular, planar, thin to felty, olive brown (4F5), arising aerial hyphae at the center (yellowish grey |

TABLE 1-continued

| Cultural characteristics of the strain F-11899 | | |
|---|---|---|
| Medium | | Cultural characteristics |
| | | (4B2)) |
| | R: | Brownish grey (4F2) |
| Potato dextrose agar (Difco 0013) | G: | Rather rapidly, 3.5–4.0 cm |
| | S: | Circular, planar, felty, somewhat wrinkly, brownish grey (4F2), arising aerial hyphae at the center (pale grey (4B1) to brownish grey (4F2)) |
| | R: | Dark grey (4F1) |
| Czapeck's solution agar (Raper and Thom 1949) | G: | Very restrictedly, 1.0–1.5 cm |
| | S: | Irregular, thin, scanty, immersed, subhyaline to white |
| | R: | Subhyaline to white |
| Sabouraud dextrose agar (Difco 0109) | G: | Restrictedly, 2.0–2.5 cm |
| | S: | Circular, planar, thin, white, sectoring, light brown (6D5) at the colony center |
| | R: | Pale yellow (4A3) |
| Oatmeal agar (Difco 0552) | G: | Fairly rapidly, 4.0–4.5 cm |
| | S: | Circular, planar, felty to cottony, dark grey (4F1) to brownish grey (4F2) |
| | R: | Brownish grey (4D2) |
| Emerson Yp Ss agar (Difco 0739) | G: | Restrictedly, 2.0–2.5 cm |
| | S: | Circular to irregular, planar, felty, dark grey (4F1) to brownish grey (4F2) |
| | R: | Medium grey (4E1) to dark grey (4F1) |
| Corn meal agar (Difco 0386) | G: | Rather restrictedly, 2.5–3.0 cm |
| | S: | Circular, planar, thin to felty, dark grey (2F1) to olive (2F3) |
| | R: | Dark grey (2F1) to olive (2F3) |
| MY20 agar | G: | Restrictedly, 1.5–2.0 cm |
| | S: | Circular to irregular, thin, sectoring, yellowish white (4A2) |
| | R: | Pale yellow (4A3) to orange white (5A2) |
| Abbreviations: | G: | growth, measuring colony size in diameter |
| | S: | colony surface |
| | R: | reverse |

These characteristics were observed after 14 days of incubation at 25° C. The color descriptions were based on the Methuen Handbook of Colour (Kornerup, A. and Wanscher, J. H.: "Methuen Handbook of Colour," 3rd ed., Methuen, London (1983)).

A culture of Coelomycetes strain F-11899 thus named has been deposited with the Fermentation Research Institute Agency of Industrial Science and Technology (1–3, Higashi 1 chome, Tsukuba-shi, IBARAKI 305 JAPAN) on Oct. 26, 1989 under the number of FERM BP-2635.

After further studies of the classification of the strain F-11899, the strain F-11899 more closely resembled *Coleophoma empetri* (Rostrup) Petrak 1929 (von Arx, J. A.: "The Genera of Fungi—Sporulating in Pure Culture," 3rd ed., J. Cramer, ed., Vaduz, 1974; Sutton, B. C.: "The Coelomycetes—Fungi Imperfecti with Pycnidia, Acervuli and Stromata," Commonwealth Mycological Institute, Kew, 1980; Hawksworth, D. L., Sutton, B. C., and Ainsworth, G. C.: "Dictionary of the Fungi," 7th ed., Commonwealth Mycological Institute, Kew, 1983) belonging to the order Coelomycetes, but differed in some pycnidial characteristics: globose or flattened at the base, immersed, and not papillate.

Considering these characteristics, we classified this strain in more detail and renamed it as "Coleophoma sp. F-11899".

In this connection, appropriate steps were taken to amend the name, "Coelomycetes strain F-11899" to Coleophoma sp. F-11899 with the Fermentation Research Institute Agency of Industrial Science and Technology on Sep. 21, 1990.

(ii) Production of the compound [Ia] or a salt thereof

The compound [Ia] of the present invention or a salt thereof (SEQ ID NO: 1) is produced when the strain belonging to the genus Coleophoma capable of producing the compound [Ia] or a salt thereof is grown in a nutrient medium containing sources of assimilable carbon and nitrogen under aerobic conditions (e.g., shaking culture, submerged culture, etc.).

The preferred sources of carbon in the nutrient medium are carbohydrates such as glucose, sucrose, starch, fructose and/or glycerin, and the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g., ammonium nitrate, ammonium sulfate, ammonium phosphate, etc.), urea and/or amino acids, and the like.

The carbon and nitrogen sources, though advantageously employed in combination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salts and/or cobalt salts, and the like.

If necessary, a defoaming agent, such as liquid paraffin, fatty oil, plant oil, mineral oil or silicone, or the like may be added, especially when foaming of the culture medium presents a serious problem.

As in the case of the preferred methods used for the production of other biologically active substances in massive amounts, submerged aerobic cultural conditions are preferred for the production of the compound [Ia] or a salt thereof in massive amounts.

For the production of the compound [Ia] or a salt thereof in small amounts, a shaking or surface culture in a flask or bottle is employed.

Further, when the growth is carried out in large tanks, it is preferable to use the vegetative form of the organism for inoculation in the production tanks in order to avoid growth lag in the process of production of the compound [Ia] or a salt thereof. Accordingly, it is desirable first to produce a vegetative inoculum of the organism by inoculating a relatively small quantity of culture medium with spores or mycelia of the organism and culturing said inoculated medium, and then to transfer the cultured vegetative inoculum to large tanks. The medium, in which the vegetative inoculum is produced, is substantially the same as the medium utilized for the production of the compound [Ia] or a salt thereof, or may be different from the medium, as desired.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 20° C. to 30° C., for a period of about 50 hours to 150 hours, which may be varied according to fermentation conditions and scales.

When the fermentation is completed, the compound [Ia] or a salt thereof is isolated from the culture broth by various procedures conventionally used for recovery and purification of biologically active substances. For instance, solvent extraction with an appropriate solvent or a mixture of solvents, chromatography or recrystallization from an appropriate solvent or a mixture of solvents, or the like, may be used.

According to the present invention, in general, the compound [Ia] or a salt thereof is found both in the cultured mycelia and cultured broth. Accordingly, the compound [Ia] or a salt thereof is removed from the whole broth by means of extraction using an appropriate organic solvent such as acetone or ethyl acetate, or a mixture of these solvents, or the like.

The extract is treated in a conventional manner to provide the compound [Ia] or a salt thereof. For example, the extract is concentrated by evaporation or distillation, and the resulting residue containing active material (i.e., the compound [Ia] or a salt thereof) is purified by conventional purification procedures; for example, chromatography, or recrystallization from an appropriate solvent or a mixture of solvents, or both.

When the object compound is isolated as a salt of the compound [Ia], it can be converted to the free compound [Ia] or another salt of the compound [Ia] according to a conventional manner.

Process 2

The compound [Ib] (SEQ ID NO: 1) or a salt thereof can be prepared by subjecting the compound [Ia] or a salt thereof to an elimination reaction of the sulfo group.

Suitable salts of the compound [Ib] include the acid addition salts as exemplified for the compound [I].

This elimination reaction is carried out in accordance with conventional methods in this field of the art, such as reaction with an enzyme, or the like.

The reaction with an enzyme can be carried out by reacting the compound [Ia] or a salt thereof with an enzyme suitable for the elimination reaction of the sulfo group.

A suitable example of said enzyme includes a sulfatase, such as sulfatase Type IV, produced by *Aeobacter aerogenes*, or the like.

This elimination reaction is usually carried out in a solvent such as phosphate buffer, Tris-HCl buffer, or any other solvent which does not adversely influence the reaction.

The reaction temperature is not critical and the reaction can be carried out at room temperature or with warming.

Process 3

The object compound [Id] (SEQ ID NO: 1) or a salt thereof can be prepared by subjecting the compound [Ic] or a salt thereof to an elimination reaction of the appropriate N-acyl group.

This reaction is carried out in accordance with conventional methods, such as hydrolysis, reduction, reaction with an enzyme, or the like.

The hydrolysis is preferably carried out in the presence of either a base or an acid, including a Lewis acid. Suitable bases include inorganic bases such as an alkali metal [e.g., sodium, potassium, etc.], an alkaline earth metal [e.g., magnesium, calcium, etc.], the hydroxides, carbonates or bicarbonates thereof; and organic bases, such as trialkylamines [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, and the like.

Suitable acids include organic acids [e.g., formic acid, acetic acid, propionic acid, trichloroacetic acid, trifluoroacetic acid, etc.] and inorganic acids [e.g., hydrochloric acid, hydrobromic acid, sulfuric acid, etc.]. The elimination using a Lewis acid such as a trihaloacetic acid [e.g., trichloroacetic acid, trifluoroacetic acid, etc.] or the like is preferably carried out in the presence of cation trapping agents [e.g., anisole, phenol, etc.].

The reaction is usually carried out in a solvent such as water, a lower alcohol [e.g., methanol, ethanol, etc.], methylene chloride, tetrahydrofuran, a mixture thereof or any other solvent which does not adversely influence the reaction. A liquid base or acid can be also used as the solvent. The reaction temperature is not critical, and can be carried out either under cooling, at ambient temperatures or with warming; for example at a temperature of from 0° C. to 100° C.

The reduction methods applicable for the elimination reaction include both chemical reduction and catalytic reduction.

Suitable reducing agents to be used in chemical reduction are a combination of a metal [e.g., tin, zinc, iron, etc.] or a metallic compound [e.g., chromium chloride, chromium acetate, etc.] and an organic or inorganic acid [e.g., formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g., platinum plate, spongy platinum, platinum black, colloidal platinum, platinum oxide, platinum wire, etc.], palladium catalysts [e.g., spongy palladium, palladium black, palladium oxide, palladium on carbon, colloidal palladium, palladium on barium sulfate, palladium on barium carbonate, etc.], nickel catalysts [e.g., reduced nickel, nickel oxide, Raney nickel, etc.], cobalt catalysts [e.g., reduced cobalt, Raney cobalt, etc.], iron catalysts [e.g., reduced iron, Raney iron, etc.], copper catalysts [e.g., reduced copper, Raney copper, Ullman copper, etc.], and the like.

The reduction is usually carried out in a conventional solvent which does not adversely influence the reaction, such as water, methanol, ethanol, propanol, N,N-dimethylformamide, or mixtures thereof. Additionally, the above-mentioned acids which can to be used in chemical reduction which are also liquid at the reduction temperature can also be used as a solvent. Further, a suitable solvent to be used in catalytic reduction may be selected from the above-mentioned solvents and other conventional solvents such as diethyl ether, dioxane, tetrahydrofuran, etc., or mixtures thereof.

The reaction temperature of the reduction is not critical, and the reaction is usually carried out under cooling, at ambient temperatures, or with warming; preferably, at a temperature of from 0° C. to 100° C.

The reaction with an enzyme can be carried out by reacting the compound [Ic] or a salt thereof with an enzyme suitable for the elimination reaction of the N-acyl group.

Suitable examples of said enzyme include appropriate enzymes produced by certain microorganisms of the Actinoplanaceae; for example, *Actinoplanes utahensis* IFO–13244, *Actinoplanes utahensis ATCC* 12301, and *Actinopanes missourienses* NRRL 12053; and the like.

The enzymatic elimination reaction is usually carried out in a solvent such as phosphate buffer, Tris-HCl buffer or any other solvent which does not adversely influence the reaction.

The reaction temperature is not critical, and the reaction can be carried out at room temperature or under warming.

Process 4

The object compound [Ie] (SEQ ID NO: 1) or a salt thereof can be prepared by subjecting the compound [Id] or a salt thereof to an acylation reaction.

The acylation reaction of this process can be carried ut by reacting the compound [Id] or a salt thereof with the aforesaid "acylating agent"; for example, the compound [V], a salt thereof, or a corresponding reactive derivative at the carboxy group.

Suitable reactive derivatives at the carboxy group of the compound [V] include an acid halide or an acid anhydride (as described above), an activated amide, an activated ester, and the like. Suitable examples of the reactive derivatives include an acid chloride; an acid azide; a mixed acid anhydride with an acid such as a substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivalic acid, pentanoic acid, isopentanoic acid, 2-ethylbutyric acid, trichloroacetic acid, etc.], or aromatic carboxylic acid [e.g., benzoic acid, etc.], a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with an N-hydroxy compound [e.g., N,N-dimethylhydroxylamine, 1-hydroxy-2-(1H)-pyridone, N-hydroxysuccinimide, N-hydroxyphthalimide, 1-hydroxy-1H-benzotriazole, etc.], and the like.

Suitable salts of the compound [V] and its reactive derivative are as described for the compound [I].

The reaction is usually carried out in a conventional solvent such as water, lower alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound [V] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N'-carbonylbis-(2-methylimidazole); pentamethyleneketene-N-cyclohexylimine; diphenylketene-N-cyclohexylimine; ethoxyacetylene; 1-alkoxy-1chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; a Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction can be carried out under cooling, at ambient temperatures, or with warming, preferably at a temperature of from 0° C. to 100° C.

Process 5

The object compound [Ig] (SEQ ID NO: 1) or a salt thereof can be prepared by subjecting a compound [If] or a salt thereof to an elimination reaction of the appropriate amino protective group.

Suitable salts of the compounds [If] and [Ig] can be chosen from among those exemplified for the compound [I]. This elimination reaction can be carried out in accordance with conventional methods, as explained above for Process 3.

Process 6

The object compound [Ii] (SEQ ID NO: 1) or a salt thereof can be prepared by reacting a compound [Ih] or a salt thereof with a compound [II] or a salt thereof.

Suitable salts of the compound [Ii] can be selected from the ones as exemplified for the compound [I].

Suitable salts of the compound [II] can be selected from acid addition salts as exemplified for the compound [I].

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction. Preferably, the solvent has a strong polarity. Among the solvents, hydrophilic solvents may be used in a mixture with water. When the compound [II] is liquid, it can also be used as a solvent.

The reaction is preferably conducted in the presence of a base. For example, inorganic bases such as alkali metal hydroxides, alkali metal carbonates, alkali metal bicarbonates, and organic bases such as a tri(lower)alkylamine, and the like, are particularly suitable.

The reaction temperature is not critical, and the reaction can be carried out under cooling, at room temperature, under warming or under heating, preferably at a temperature of from 0° C. to 150° C.

The present reaction is preferably carried out in the presence of alkali metal halide [e.g., sodium iodide, potassium iodide, etc.], alkali metal thiocyanate [e.g., sodium thiocyanate, potassium thiocyanate, etc.], or the like.

Process 7

The object compound [Ij] (SEQ ID NO: 1) or a salt thereof can be prepared by subjecting a compound [III] or a salt thereof to an acylation reaction.

Suitable salts of the compounds [Ii] and [III] can be selected from those exemplified for the compound [I].

A suitable "acylating agent" in this process may be an acid compound corresponding to the functional group to be introduced; for example, phosphoric acid and its derivatives (e.g., phophoryl chloride, diphenylphosphorochloridate, etc.), sulfuric acid and its derivatives [e.g., sulfur trioxide-pyridine, sulfur trioxide-tri(lower)alkylamine (e.g., trimethylamine, triethylamine, etc.), chlorosulfonic acid, etc.], or the like.

This reaction can be carried out in a conventional manner.

Other features of the invention will become apparent in the course of the following descriptions of exemplary embodiments which are given for illustration of the invention, are not intended to be limiting thereof.

The following Preparations and Examples are given for the purpose of illustrating the present invention in more detail. By procedure(s) or method(s) similar to that of another Preparation or Example, the procedural steps are the same, but the starting material and/or co-reactant is changed to correspond to and provide the given product.

Preparation 1

To methanol (50 ml) was added thionyl chloride (8.73 ml) at −5° C. and the mixture was stirred for 10 minutes. D-2-(p-Hydroxyphenyl)glycine (5 g) was then added thereto under ice-cooling. The mixture was stirred for 12 hours at room temperature, then the volatile components were evaporated under reduced pressure to give D-2-(p-hydroxyphenyl)glycine methyl ester hydrochloride (6.3 g).

IR (Nujol): 3380, 1720, 1580, 1250 $cm^{-1}$

NMR (DMSO-$d_6$, δ): 3.70 (3H, s), 5.11 (1H, s), 6.83 (2H, d, J=8.6 Hz), 7.28 (2H, d, J=8.6 Hz), 8.91 (2H, s), 9.93 (1H, s)

Preparation 2

To a solution of D-2-(p-hydroxyphenyl)glycine methyl ester hydrochloride (6.3 g) and triethylamine (8.71 ml ) in tetrahydrofuran (100 ml ) was added di-t-butyl dicarbonate (6.82 g). The mixture was stirred for 2 hours at room temperature, then the reaction mixture was added to diethyl ether (1 l), and an insoluble material was filtered off. The filtrate was evaporated under reduced pressure to give N-(t-butoxycarbonyl)-D-2-(p-hydroxyphenyl)glycine methyl ester (6.83 g).

IR (Nujol): 3420, 3350, 1720, 1660 $cm^{-1}$

NMR (DMSO-$d_6$, δ): 1.38 (9H, s), 3.59 (3H, s), 5.05 (1H, d, J=7.9 Hz), 6.70 (2H, d, J=8.5 Hz), 7.16 (2H, d, J=8.5 Hz), 7.60 (1H, d, J=7.9 Hz), 9.48 (1H, s)

Preparation 3

To a suspension of N-(t-butoxycarbonyl)-D-2-(p-hydroxyphenyl)glycine methyl ester (6.8 g) and potassium bicarbonate (1.84 g) in N,N-dimethylformamide (34 ml) was added octyl bromide (4.176 ml). The mixture was stirred for 6 hours at 60° C. The reaction mixture was added to a mixture of water and ethyl acetate. The organic layer was separated, and dried over magnesium sulfate. The magnesium sulfate was filtered off, and the filtrate was evaporated under reduced pressure to give N-(t-butoxycarbonyl)-D-2-(p-octyloxyphenyl)glycine methyl ester (6.96 g).

IR (Nujol): 1710, 1490, 1240, 1160 $cm^{-1}$

NMR (DMSO-$d_6$, δ): 0.859 (3H, t, J=6.2 Hz), 1.17–1.33 (10H, m), 1.38 (9H, s), 1.60–1.80 (2H, m), 3.59 (3H, s), 3.93 (2H, t, J=6.3 Hz), 5.11 (1H, d, J=7.9 Hz), 6.87 (2H, d, J=8.7 Hz), 7.27 (2H, d, J=8.7 Hz), 7.68 (1H, d, J=7.9 Hz)

Preparation 4

To a 4N aqueous solution of sodium hydroxide (8.77 ml) was added N-(t-butoxycarbonyl)-D-2-(p-octyloxyphenyl)glycine methyl ester (6.9 g). The mixture was stirred for 1.5 hours at room temperature. The reaction mixture was added to a mixture of water and ethyl acetate, and 1N hydrochloric acid was added thereto to adjust the mixture to pH 3. The organic layer was separated and dried over magnesium sulfate. The magnesium sulfate was filtered off, and the filtrate was evaporated under reduced pressure to give N-(t-butoxycarbonyl)-D-2-(p-octyloxyphenyl)glycine (3.9 g).

NMR (DMSO-$d_6$, δ): 0.860 (3H, t, J=6.8 Hz), 1.17–1.33 (10H, m), 1.38 (9H, s), 1.60–1.80 (2H, m), 3.93 (2H, t, J=6.4 Hz), 5.10 (1H, d, J=8.2 Hz), 6.87 (2H, d, J=8.7 Hz), 7.28 (2H, d, J=8.7 Hz), 7.46 (1H, d, J=8.2 Hz)

Preparation 5

To a solution of N-(t-butoxycarbonyl)-D-2-(p-octylaxyphenyl)glycine (1 g) in acetonitrile (10 ml) and pyridine (0.213 ml) in acetonitrile (10 ml) was added N,N'-disuccinimidyl carbonate (0.675 g). The mixture was stirred for 12 hours at room temperature, then was added to a mixture of water and ethyl acetate. The organic layer was separated and dried over magnesium sulfate. The magnesium sulfate was filtered off, and the filtrate was evaporated under reduced pressure to give N-(t-butoxycarbonyl)-D-2-(p-octyloxyphenyl)glycine succinimido ester (0.92 g).

IR (Nujol): 3350, 1810, 1730, 1680 $cm^{-1}$

NMR (DMSO-$d_6$, δ): 0.862 (3H, t, J=6.7 Hz), 1.17–1.33 (10H, m), 1.40 (9H, s), 1.60–1.80 (2H, m), 2.77 (4H, s), 3.97 (2H, t, J=6.5 Hz), 5.54 (1H, d, J=8.1 Hz), 6.91 (2H, d, J=8.7 Hz), 7.39 (2H, d, J=8.7 Hz ), 8.05 ( 1H, d, J=8.1 Hz )

Preparations 6 through 9 were conducted in the manner of Preparations 2 through 5, employing L-tyrosine methyl ester as the starting material.

Preparation 6

N-(t-Butoxycarbonyl)-L-tyrosine methyl ester was prepared by the procedure of Preparation 2.

IR (Nujol): 3430, 3360, 1730, 1670, 1170 $cm^{-1}$

NMR (DMSO-$d_6$, δ): 1.33 (9H, s) , 2.90 (2H, m) , 3.59 (3H, s), 4.05 (1H, m), 6.65 (2H, d, J=8.4 Hz), 7.00 (2H, d, J=8.4 Hz), 7.21 (1H, d, J=8.0 Hz), 9.22 (1H, s)

Preparation 7

$O^4$-Octyl-N-(t-butoxycarbonyl)-L-tyrosine methyl ester was prepared according to the procedure of Preparation 3.

IR (Nujol): 3350, 1735, 1685, 1250, 1170

NMR (DMSO-$d_6$, δ): 0.859 (3H, t, J=6.7 Hz), 1.20–1.30 (10H, m), 1.68 (2H, quintet, J=7.3 Hz), 2.82 (2H, m), 3.60 (3H, s), 3.91 (2H, t, J=7.3 Hz), 4.08 (1H, m), 6.81 (2H, d, J=8.6 Hz), 7.12 (2H, d, J=8.6 Hz), 7.25 (1H, d, J=8.0 Hz)

Preparation 8

$O^4$-Octyl-N-(t-butoxycarbonyl)-L-tyrosine was prepared according to the procedure of Preparation 4.

IR (Nujol): 3400–2900 (br), 1700, 1240, 1160 $cm^{-1}$

NMR (DMSO-$d_6$, δ): 0.859 (3H, t, J=6.8 Hz), 1.20–1.30 (10H, m), 1.32 (9H, s), 1.68 (2H, quintet, J=7.0 Hz), 2.67–2.95 (1H, m), 3.90 (2H, t, J=7.0 Hz), 4.01 (1H, m), 6.81 (2H, d, J=8.6 Hz), 7.02 (1H, d, J=8.3 Hz) , 7.13 (2H, d, J=8.6 Hz)

Preparation 9

$O^4$-Octyl-N- (t-butoxycarbonyl) -L-tyrosine succinimido ester was prepared according to the procedure of Preparation 5.

IR (Nujol): 3350, 1780, 1720, 1690 $cm^{-1}$

NMR (DMSO-$d_6$, δ): 0.860 (3H, t, J=6.7 Hz), 1.20–1.30 (10H, m), 1.32 (9H, s), 1.68 (2H, quintet, J=7.0 Hz), 2.82 (4H, s), 2.80–3.20 (1H, m), 3.92 (2H, t, J=7.0 Hz), 4.44 (1H, m), 6.81 (2H, d, J=8.5 Hz), 7.22 (2H, d, J=8.5 Hz), 7.60 (1H, d, J=8.3 Hz)

Preparation 10

(1) A seed medium (160 ml) consisting of 4% sucrose, 2% cotton seed flour, 1% dried yeast, 1% peptone, 0.2% $KH_2PO_4$, 0.2% $CaCO_3$ and 0.1% TWEEN 80 (made by NAKARAI CHEMICALS LTD.) was poured into each of two 500 ml Erlenmeyer flasks and sterilized at 121° C. for 30 minutes. A loopful of slant culture of Coleophoma sp. F-11899 was inoculated to each of the media and cultured with shaking at 25° C. for 4 days.

A production medium (20 liters) consisting of 3% PINE DEX #3 (made by Matsutani Chemical Ltd.), 1% glucose, 1% wheat germ, 0.5% cotton seed flour, 2% $KH_2PO_4$, 1.5% $Na_2HPO_4.12H_2O$, 0.001% $ZnSO_4.7H_2O$ and 0.05% ADEKANOL (defoaming agent, made by Asahi Denka Co., Ltd.) was poured into a 30 liter jar fermentor and sterilized at 121° C. for 30 minutes.

The resultant seed culture broth (320 ml) was inoculated to the production medium and cultured at 25° C. for 4 days, agitated at 200 rpm and aerated at 20 liters per minute. To the cultured broth thus obtained (20 liters) was added an equal volume of acetone. After occasionally stirring at room temperature for a while, the broth was filtered. The filtrate was concentrated in vacuo to remove acetone. The aqueous filtrate (10 liters) was washed with two equal volumes of ethyl acetate, and extracted with n-butanol (10 liters) twice. The combined n-butanol layers were concentrated in vacuo and the residue was applied on a column (300 ml) of SILICA GEL 60 (made by E. Merck) and eluted with a stepwise organic solvent mixture consisting of dichloromethane-methanol. The fractions having anti-Candida activity were eluted in the range of the solvent mixture (3:1 through 1:1). The active fractions were combined and concentrated in vacuo to dryness. The residue was dissolved in 50% aqueous methanol (15 ml) and applied on a column (250 ml) of ODS YMC GEL (made by Yamamura Chemical Lab.). The column was washed with 50% aqueous methanol and eluted with 80% aqueous methanol. The eluate was concentrated and was further purified on a centrifugal partition chromatography (CPC) using a solvent system n-butanol:methanol:water (4:1:5) of upper stationary phase and lower mobile phase in a descending mode. The pooled fractions containing the object compound (major component) were concentrated in vacuo and applied on a column (35 ml) of SILICA GEL 60. The column was developed with n-butanol:acetic acid:water (6:1:1). The active fractions were combined and concentrated in vacuo to dryness and dissolved in a small volume of 50% aqueous methanol. The solution was passed through a column (3.5 ml) of ODS YME GEL. The column was washed with 50% aqueous methanol and eluted with methanol. The eluate was concentrated to dryness, dissolved in a small volume of water and adjusted to pH 7.0 with 0.01N NaOH. The solution was freeze-dried to give a white powder in its sodium salt form (hereinafter referred to as FR901379 substance) (11 mg).

The fractions containing two minor components after CPC were concentrated in vacuo and purified on a preparative high performance liquid chromatography (HPLC) column of LICHROSORB RP-18 (Trademark, made by Merck, 250×25 mm) using a mobile phase composed of 45% aqueous $CH_3CN$-0.5% $NH_4H_2PO_4$ at a flow rate of 9.9 ml/minute. The fraction containing one of the two components was diluted with an equal volume of water and passed through a column (1 ml) of ODS YMC Gel. The column was washed with 40% aqueous MeOH and eluted with MeOH. The eluate was concentrated in vacuo to dryness, then dissolved in a small volume of water and freeze-dried to give a white powder in its ammonium salt form (2.2 mg) (hereinafter referred to as FR901381 substance).

In a similar manner, the other minor component in its ammonium salt form was obtained as a white powder (1.2 mg) (hereinafter referred to as FR901382 substance).

The FR901379 substance as obtained has the following physico-chemical properties:

Appearance:

white powder

Nature:

neutral substance

Melting point:

215°–221° C. (dec.)

Specific rotation:

$[a]_D^{23}$ −20.3 (C: 0.5, $H_2O$)

Molecular formula:

$C_{51}H_{81}N_8O_{21}SNa$

Elemental Analysis:

Calcd: for $C_{51}H_{81}N_8SO_{21}Na$ C 51.17, H 6.77, N 9.36, S 2.68 (%)

Found: C 49.61, H 7.58, N 7.65, S 2.14 (%)

Molecular weight:

HRFAB-MS 1219.5078 (Calcd for $C_{51}H_{82}N_8SO_{21}$+2Na - H: 1219.5032)

Solubility:

soluble: methanol, water slightly soluble: ethyl acetate, acetone insoluble: chloroform, n-hexane Color reaction:

positive: iodine vapor reaction, cerium sulfate reaction, ferric chloride reaction, Ninhydrin reaction negative: Dragendorff reaction, Ehrlich reaction Thin layer chromatography (TLC):

| Stationary phase | Developing Solvent | Rf value |
|---|---|---|
| silica gel* | N-butanol:acetic acid: water (3:1:1) | 0.36 |
| | ethyl acetate:isopropyl alcohol:water (5:3:1) | 0.31 |

*SILICA GEL 60 (made by E. Merck)

Ultraviolet absorption spectrum:

$k_{max}^{methanol}$ ($E_{1cm}^{1\%}$): 207(169), 276(13.5), 225(sh), 283(sh) nm $k_{max}^{methanol+0.01N\text{-}NaOH}$ ($E_{1cm}^{1\%}$): 209(232), 244(59.5), 284(13.5), 294(sh) nm Infrared absorption spectrum:

$t_{max}^{KBr}$: 3350, 2920, 2840, 1660, 1625, 1530, 1510, 1435, 1270, 1240, 1070, 1045, 800, 755, 710 $cm^{-1}$ $^1H$ Nuclear magnetic resonance spectrum:

($CD_3OD$, 400 MHz)

δ: 7.30 (1H, d, J=2 Hz), 7.03 (1H, dd, J=8 and 2 Hz), 6.85 (1H, d, J=8 Hz), 5.23 (1H, d, J=3 Hz), 5.06 (1H, d, J=4 Hz), 4.93 (1H, d, J=3 Hz), 4.59–4.51 (3H, m), 4.47–4.35 (5H, m), 4.29 (1H, dd, J=6 and 2 Hz ), 4.17 ( 1H, m ), 4.07 ( 1H, m ), 3.95–3.89 (2H, m), 3.76 (1H, broad d, J=11 Hz), 3.36 (1H, m), 2.75 (1H, dd, J=16 and 4 Hz), 2.50 (1H, m), 2.47 (1H, dd, J=16 and 9 Hz), 2.38 (1H, m), 2.21 (2H, m), 2.03–1.93 (3H, m), 1.57 (2H, m), 1.45–1.20 (24H, m), 1.19 (3H, d, J=6 Hz), 1.08 (3H, d, J=6 Hz), 0.90 (3H, t, J=7 Hz)

From the analysis of the above physical and chemical properties, and the result of the further investigation and identification of the chemical structure, the chemical structure of the FR901379 substance has been identified and assigned as follows (SEQ ID NO: 1):

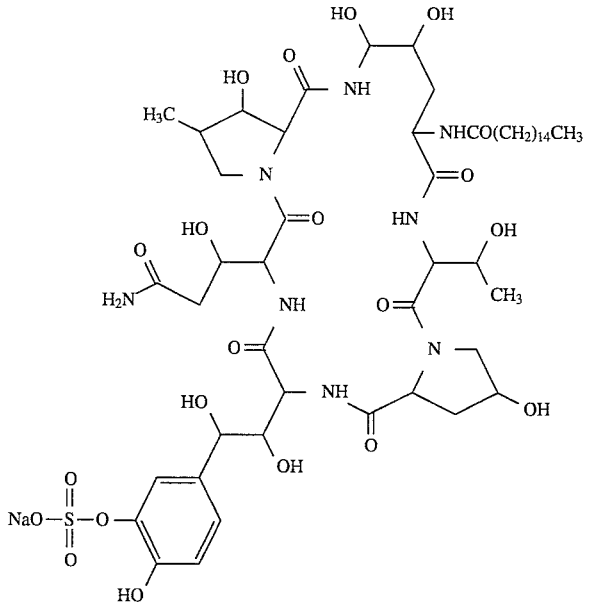

The FR901381 substance as obtained has the following physico-chemical properties:

Appearance:

white powder

Nature:

neutral substance

Melting point:

218°–223° C. (dec.)

Specific rotation:

$[a]_D^{23}$ −10.5° (C: 0.5, MeOH)

Molecular formula:

$C_{51}H_{81}N_8O_{20}S{\cdot}NH_4$

Molecular weight:

HRFAB-MS 1203.5100

(Calcd for $C_{51}H_{82}N_8O_{20}S$+2Na−H: 1203.5083)

Solubility:

soluble: methanol, ethanol slightly soluble: water, acetone insoluble: chloroform, n-hexane Color reaction:

positive: iodine vapor reaction, cerium sulfate reaction negative: Dragendorff reaction, Ehrlich reaction Thin layer chromatography (TLC):

| Stationary phase | Developing Solvent | Rf value |
|---|---|---|
| silica gel* | N-butanol:acetic acid: water (3:1:1) | 0.34 |
| | ethyl acetate:isopropyl alcohol:water (5:3:1) | 0.67 |

*SILICA GEL 60 (made by E. Merck)

Ultraviolet absorption spectrum:

$k_{max}^{methanol}$ ($E_{1cm}^{1\%}$): 206(196), 278(4), 243(sh), 284(sh) nm $k_{max}^{methanol+0.01\ N\text{-}NaOH}$ $E_{1cm}^{1\%}$): 208(252), 290(5), 241(sh) nm Infrared absorption spectrum:

$t_{max}^{KBr}$: 3300, 2900, 2840, 1680, 1660, 1640, 1620, 1510, 1460, 1430, 1330, 1240, 1040, 960 $cm^{-1}$ $^1H$ Nuclear magnetic resonance spectrum:

($CD_3OD$, 400 MHz)

δ: 7.18 (1H, d, J=2 Hz), 6.90 (1H, dd, J=2 and 8.5 Hz), 6.81 (1H, d, J=8.5 Hz), 5.29 (1H, d, J=3 Hz), 5.08 (1H, d, J=3.5 Hz), 4.98 (1H, d, J=3 Hz), 4.63 (1H, dd, J=7 and 11 Hz), 4.58–4.51 (3H, m), 4.46–4.38 (3H, m), 4.37 (1H, d, J=2 Hz), 4.16 (1H, dd, J=2 and 5 Hz), 4.07 (1H, dd, J=7.5 and 9.5 Hz), 4.02–3.94 (2H, m), 3.78 (1H, br d, J=11 Hz), 3.38 (1H, t, J=9.5 Hz), 2.69 (1H, dd, J=4.5 and 15 Hz), 2.63–2.50 (3H, m), 2.46 (1H, m), 2.43 (1H, dd, J=9 and 15 Hz), 2.21 (2H, t, J=7.5 Hz), 2.07–1.95 (3H, m), 1.58 (2H, m), 1.29 (24H, m), 1.16 (3H, d, J=6.8 Hz), 1.07 (3H, d, J=7 Hz), 0.89 (3H, t, J=6.5 Hz)

$^{13}C$ Nuclear magnetic resonance spectrum:

($CD_3OD$, 100 MHz)

δ: 176.7 (s), 175.9 (s), 174.4 (s), 174.0 (s), 172.8 (s), 172.5 (s), 172.5 (s), 169.4 (s), 149.1 (s), 141.1 (s), 131.1 (s), 128.0 (d), 125.3 (d), 118.3 (d), 75.9 (d), 74.0 (d), 73.9 (d), 71.3 (d), 70.7 (d), 70.5 (d), 70.2 (d), 68.2 (d), 62.4 (d), 58.6 (d), 58.4 (d), 57.2 (t), 55.5 (d), 52.9 (t), 51.4 (d), 40.8 (t), 39.9 (t), 39.1 (d), 39.0 (t), 36.7 (t), 35.0 (t), 33.1 (t), 30.8 (t×5), 30.7 (t), 30.7 (t), 30.5 (t), 30.4 (t), 30.3 (t), 27.0 (t), 23.7 (t), 19.5 (q), 14.4 (g), 11.1 (q)

From the analysis of the above physical and chemical properties, and the result of the further investigation for identification of the chemical structure, the chemical structure of the FR901381 substance has been identified and assigned as follows (SEQ ID NO: 1):

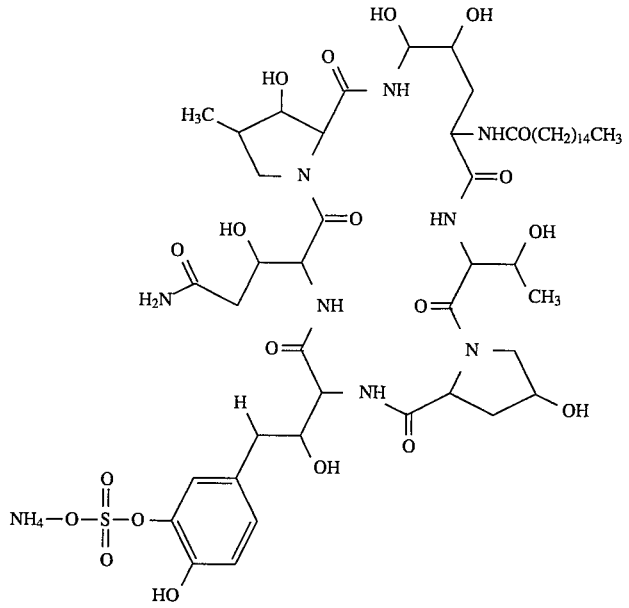

The FR901382 substance as obtained has the following physico-chemical properties:

Appearance:

white powder

Nature:

neutral substance

Melting point:

208°–217° C. (dec.)

Specific rotation:

$[a]_D^{23}$ −9.4° (C: 0.5, MeOH).

Molecular formula:

$C_{51}H_{81}N_8O_{19}S{\cdot}NH_4$

Molecular weight:

HRFAB-MS 1187.5139

(Calcd. for $C_{51}H_{82}N_8O_{19}S$+2Na−H 1187.5134)

Solubility:

soluble: methanol, ethanol slightly soluble: water, acetone insoluble: chloroform, n-hexane Color reaction:

positive: iodine vapor reaction, cerium sulfate reaction negative: Dragendorff reaction, Ehrlich reaction Thin layer chromatography (TLC):

| Stationary phase | Developing Solvent | Rf value |
|---|---|---|
| silica gel* | N-butanol:acetic acid: water (3:1:1) | 0.43 |
| | ethyl acetate:isopropyl alcohol:water (5:3:1) | 0.9 |

*SILICA GEL 60 (made by E. Merck)

Ultraviolet absorption spectrum:

$k_{max}^{methanol}$ ($E_{1cm}^{1\%}$): 205(180), 276(13) 224(sh), 283 (sh) nm $k_{max}^{methanol+0.01N\text{-}NaOH}$ ($E_{1cm}^{1\%}$): 208(262), 281(12), 241(sh), 295(sh) nm Infrared absorption spectrum:

$t_{max}^{KBr}$: 3350, 2900, 2840, 1680, 1660, 1640, 1620, 1510, 1430, 1330, 1245, 1080, 1040, 960 $cm^{-}$ $^1H$ Nuclear magnetic resonance spectrum:

($CH_3OD$, 400 MHz)

δ: 7.18 (1H, d, J=2 Hz), 6.90 (1H, dd, J=2 and 8.5 Hz), 6.80 (1H, d, J=8.5 Hz), 5.37 (1H, dd, J=3 and 11 Hz), 5.08(1H, d, J=3.5 Hz), 5.00 (1H, d, J=3 Hz), 4.61 (1H, dd, J=7 and 11 Hz), 4.59 (1H, d, J=2 Hz), 4.58–4.52 (2H, m), 4.46–4.35 (3H, m), 4.29 (1H, d, J=2 Hz), 4.12 (1H, dd, J=2 and 4.5 Hz), 4.07 (1H, dd, J=8 and 9.5 Hz), 4.01 (1H, dd, J=3 and 11 Hz), 3.77 (1H, br d, J=11 Hz), 3.37 (1H, t, J=9.5 Hz), 2.69 (1H, dd, J=4.5 and 15.5 Hz), 2.63–2.50 (3H,m), 2.45 (1H, m), 2.43 (1H, dd, J=9 and 15.5 Hz), 2.24 (2H, m), 2.09–1.95 (3H, m), 1.76–1.66 (2H, m), 1.59 (2H, m), 1.29 (24H, m), 1.15 (3H, d, J=6.5 Hz), 1.06 (3H, d, J=7 Hz), 0.89 (3H, t, J=7 Hz)

$^{13}C$ Nuclear magnetic resonance spectrum:

($CD_3OD$, 100 MHz)

δ:176.7 (s), 176.0 (s), 175.1 (s), 174.0 (s), 172.8 (s), 172.6 (s), 172.5 (s), 169.1 (s), 149.1 (s), 141.1 (s), 131.1 (s), 128.1 (d), 125.3 (d), 118.2 (d), 76.1 (d), 74.0 (d), 71.8 (d), 71.3 (d), 70.5 (d), 70.3 (d), 68.3 (d), 62.5 (d), 58.5 (d), 58.2 (d), 57.2 (t), 55.4 (d), 52.9 (t), 52.1 (d), 40.8 (t), 39.8 (t), 39.1 (d), 38.9 (t), 36.8 (t), 33.1 (t), 30.9 (t), 30.8 (t×5), 30.7 (t), 30.7 (t), 30.5 (t), 30.4 (t), 30.3 (t), 27.3 (t), 26.9 (t), 23.7 (t), 19.4 (q), 14.4 (q), 11.1 (q)

From the analysis of the above physical and chemical properties, and the result of the further investigation for identification of the chemical structure, the chemical structure of the FR901382 substance has been identified and assigned as follows (SEQ ID NO: 1):

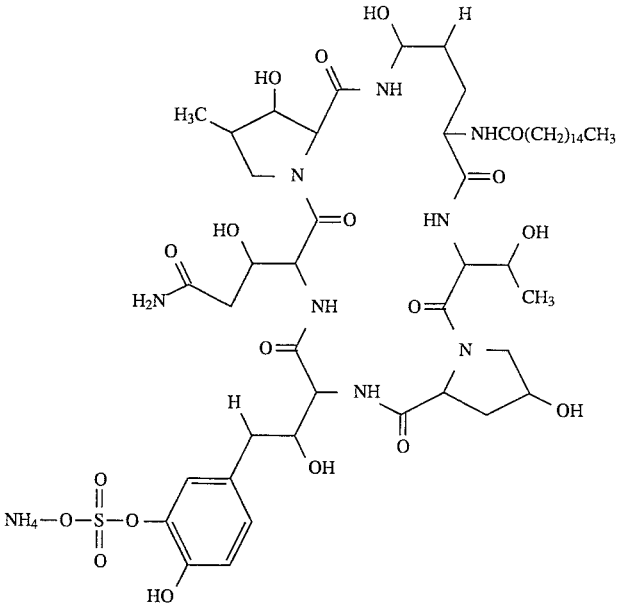

Preparation 10-1

To a solution of FR901379 substance (60 mg) in 50 mM Tris-HCl buffer (pH 7.1, 30 ml) was added sulfatase (200 U) Type VI from *Aerobacter aerogenes* (SIGMA No. S-1629). After incubating at 37° C. for 30 hours, the desulfonated FR901379 substance (hereinafter referred to as FR133302 substance) was extracted from the reaction mixture with a equal volume of n-butanol, then the organic phase was separated and washed once with water. The extract was concentrated in vacuo and applied on a column of LICHROPREP RP-18 (40–63 μm) pre-packed size B (made by Merck), equilibrated with 47% aqueous acetonitrile containing 0.5% $NH_4H_2PO_4$, and developed with the same solution. The fraction containing FR133302 substance was diluted with an equal volume of water, and directly passed through a column of ODS YMC GEL (made by Yamamura Chemical Lab.). The column was washed with water and eluted with methanol. The eluate was evaporated in vacuo to remove the methanol, and freeze-dried to give a white powder of FR133302 substance (26 mg).

The FR133302 substance has the following physicochemical properties:

Appearance:

white powder

Nature:

neutral substance

Melting point:

218°–222° C. (dec.)

Specific rotation:

$[a]_D^{23}$ −30° (C: 1.0, MeOH)

Molecular formula:

$C_{51}H_{82}N_8O_{18}$

Molecular weight:

HRFAB-MS 1117.5659

(Calcd. for $C_{51}H_{82}N_8O_{18}$+Na 1117.5645)

Solubility:

soluble: methanol, ethanol slightly soluble: water, ethyl acetate insoluble: chloroform, n-hexane Color reaction:

positive: iodine vapor reaction, cerium sulfate reaction negative: Dragendorff reaction, Molish reaction Thin layer chromatography (TLC):

| Stationary phase | Developing Solvent | Rf value |
|---|---|---|
| silica gel* | n-butanol:acetic acid: water (6:1:1) | 0.35 |

*SILICA GEL 60 (made by E. Merck)

Ultraviolet absorption spectrum:

$k_{max}^{methanol}$ ($E_{1cm}^{1\%}$): 207(353), 282(25), 232(sh), nm $k_{max}^{methanol+0.01N\text{-}NaOH}$ ($E_{1cm}^{1\%}$): 208(462), 246(54.5), 293(31.2) nm Infrared absorption spectrum:

$t_{max}^{KBr}$: 3350, 2925, 2855, 1660, 1630, 1530, 1445, 1285, 1250, 1065 $cm^{-1}$ $^1H$ Nuclear magnetic resonance spectrum:

($CD_3OD$, 400 MHz)

δ: 6.79 (1H, d, J=2 Hz), 6.71 (1H, d, J=8 Hz), 6.61 (1H, dd, J=8 and 2 Hz), 5.25 (1H, d, J=2.5 Hz), 5.06 (1H, d, J=4 Hz), 4.96 (1H, d, J=3 Hz), 4.60–4.20 (9H, m), 4.15 (1H, m), 4.08 (1H, m), 3.99 (1H, m), 3.91 (1H, m), 3.77 (1H, m), 3.34 (1H, m), 2.80 (1H, dd, J=15 and 3 Hz), 2.54–2.40 (3H, m), 2.20 (2H, t, J=7 Hz), 2.05–1.96 (3H, m), 1.56 (2H, m), 1.35–1.20 (24H, m), 1.15 (3H, d, J=6 Hz), 1.02 (3H, d, J=7 Hz), 0.89 (3H, t, J=7 Hz)

$^{13}C$ Nuclear magnetic resonance spectrum:

($CD_3OD$, 100 MHz)

δ: 177.2 (s), 175.8 (s), 174.5 (s), 173.4 (s), 172.7 (s), 172.6 (s), 172.5 (s), 169.1 (s), 146.4 (s), 146.3 (s), 133.7 (s), 120.1 (d), 116.2 (d), 115.3 (d), 76.9 (d), 75.9 (d), 75.8

(d), 74.0 (d), 71.3 (d), 70.6 (d), 70.6 (d), 70.1 (d), 68.2 (d), 62.5 (d), 58.4 (d), 57.1 (t), 56.4 (d), 55.6 (d), 53.0 (t), 51.5 (d), 39.5 (t), 39.0 (d), 38.5 (t), 36.7 (t), 34.8 (t), 33.1 (t), 30.8 (t×5), 30.7 (t), 30.6 (t), 30.5 (t), 30.4 (t), 30.3 (t), 26.9 (t), 23.7 (t), 19.7 (q), 14.4 (g), 11.1 (q)

The chemical structure of the FR133302 substance is follows (SEQ ID NO: 1):

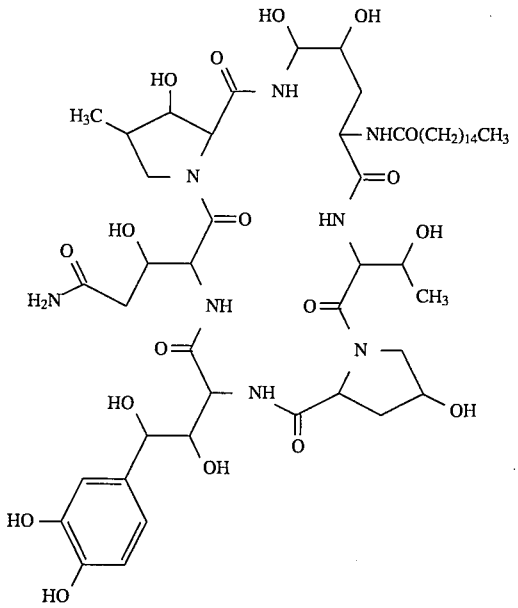

EXAMPLE 1

The N-acyl group of FR901379 substance was eliminated by reaction with an enzyme. In the following description, this elimination process is explained in detail.

(1) Fermentation of *Actinoplanes utahensis*

The enzyme which is useful for eliminating the N-acyl group of FR901379 substance is produced by certain microorganisms of the Actinoplanaceae, preferably the microorganism *Actinoplanes utahensis* IFO-13244.

A stock culture of *Actinoplanes utihensis* IFO-13244 was prepared and maintained on an agar slant. A loopful of the slant culture was inoculated into a seed medium consisting of 1% starch, 1% sucrose, 1% glucose, 1% cotton seed flour, 0.5% peptone, 0.5% soy bean meal and 0.1% $CaCO_3$. The inoculated vegetative medium was incubated in a 225 ml wide mouth Erlenmeyer flask at 30° C. for about 72 hours on a rotary shaker.

This incubated vegetative medium was used directly to inoculate into a production medium consisting of 2% sucrose, 1% peanut powder, 0.12% $K_2HPO_4$, 0.05% $KH_2PO_4$ and 0.025% $MgSO_4 \cdot 7H_2O$. The inoculated production medium was allowed to ferment in a 30 liter jar fermentor at a temperature of 30° C. for about 80 hours. The fermentation medium was stirred with conventional agitators at 250 rpm and aerated at 20 liters per minute. The vegetative mycelium was collected from the fermented broth by filtration and once washed with water. The washed mycelium was directly used as an enzyme source to eliminate the N-acyl group of FR901379 substance.

(2) Elimination Conditions

FR901379 substance was dissolved in 0.25M phosphate buffer (pH 6.5) at a concentration of 0.9 mg/ml. To 36 liters of the solution, 2 kg wet weight of the washed mycelium of *Actinoplanes utahensis* IFO-13244 was added. The elimination reaction was carried out at 37° C. for 23 hours. The reduction of FR901379 substance and subsequent increase of the deacylated FR901379 substance (hereinafter referred to as FR133303 substance) were measured using a HPLC equipped with a reverse phase column. From 30 g of FR901379 substance, 22.2 g of FR133303 substance was formed in the reaction mixture.

(3) Isolation of FR133303 Substance

The reaction mixture described above was filtered with a filter aid. The mycelial cake was discarded. The filtrate thus obtained was passed through a column of activated carbon (2 L). The column was washed with 6 L of water and eluted with 12 L of 50% aqueous acetone. The eluate was evaporated in vacuo to remove acetone and then passed through a column (4 L) of YMC GEL ODS-AM 120-S50 (Yamamura Chemical Labs). The column was washed with water and eluted with 2% aqueous acetonitrile containing 50 mM $NaH_2PO_4$. Elution was monitored by analytical HPLC, using a column of LICHROSPHER 100 RP-18 (Cica-MERCK) and a solvent system of 3% aqueous acetonitrile containing 0.5% $NH_4H_2PO_4$ at a flow rate of 1 ml/min, detecting the FR133303 substance with a UV monitor at 210 nm. The fractions containing the FR133303 substance were combined passed through a column of activated carbon (400 ml). The column was washed with water and eluted with 50% aqueous acetone. The eluate was concentrated in vacuo to remove acetone, and lyophilized to give 16.4 g of FR133303 substance as a white powder.

FR133303 substance has following physico-chemical properties:

Appearance:

white powder

Melting point:

150°–160° C. (dec.)

Specific rotation:

$[a]_D^{24}$ −31.17° (C: 1.0, $H_2O$)

Molecular formula:

$C_{35}H_{51}N_8SO_{20}Na$:

Elemental Analysis:

Calcd: for $C_{35}H_{51}N_8SO20Na$: C 43.84, H 5.36, N 11.69, S 3.34 (%)

Found: C 41.14, H 5.74, N 10.88, S 3.10 (%)

Solubility:

1soluble: water slightly soluble: methanol insoluble: n-hexane

Color reaction:

positive: iodine vapor reaction, cerium sulfate reaction, Ninhydrin reaction negative: Molish reaction Thin layer chromatography (TLC):

| Stationary phase | Developing Solvent | Rf value |
|---|---|---|
| silica gel* | N-butanol:acetic acid: water (3:1:1) | 0.15 |

*SILICA GEL 60 (made by E. Merck)

Ultraviolet absorption spectrum:

$k_{max}^{H_2O}$ ($E_{1\ cm}^{1\%}$): 201(340), 273(18), 224(sh), 281(sh) nm $k_{max}^{H_2O+0.01\ N\text{-}NaOH}$ ($E_{1\ cm}^{1\%}$): 207(414), 243(122), 292 (34)

Infrared absorption spectrum:

$t_{max}^{KBr}$: 3350, 2920, 1660, 1625, 1515, 1440, 1270, 1080, 1045, 800, 755, 715 $cm^{-1}$ $^1H$ Nuclear magnetic resonance spectrum:

($D_2O$, 400 MHz)

δ: 7.31 (1H, d, J=2 Hz), 7.12 (1H, dd, J=2 and 8 Hz), 7.06 (1H, d, J=8 Hz), 5.40 (1H, d, J=3 Hz), 5.04 (1H, d, J=3.5 Hz), 4.94 (1H, d, J=6 Hz), 4.73–4.55 (3H, m), 4.51–4.38 (4H, m), 4.31–4.23 (3H, m), 4.11–4.06 (2H, m), 3.94–3.89 (2H, m), 3.41 (1H, m), 2.60–2.34 (5H, m), 2.14 (1H, m), 2.03 (1H, m), 1.28 (3H, d, J=6 Hz), 1.01 (3H, d, J=6.5 Hz)

$^{13}C$ Nuclear magnetic resonance spectrum:

(D20, 100 M Hz)

δ: 178.3 (s), 175.9 (s), 174.3 (s), 174.2 (s), 174.0 (s), 171.8 (s), 171.3 (s), 150.9 (s), 141.5 (s), 134.4 (s), 128.2 (d), 124.5 (d), 120.3 (d), 78.1 (d), 77.0 (d), 76.9 (d), 76.6 (d), 72.9 (d), 72.8 (d), 71.2 (d), 69.3 (d), 69.2 (d), 63.7 (d), 60.1 (d), 58.3 (t), 58.0 (d), 56.9 (d), 55.3 (d), 54.7 (t), 41.8 (t), 39.7 (d), 39.5 (t), 33.5 (t), 21.4 (q), 13.3 (q)

The chemical structure of FR133303 substance has been identified and assigned as follows (SEQ ID NO: 1):

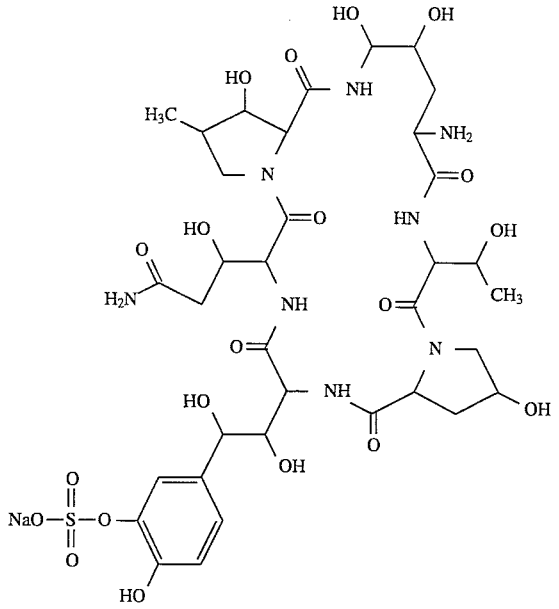

EXAMPLE 2

(1) A solution of 4-hydroxybenzoic acid (19.2 g) in 10% NaOH (120 ml) was dropwise added to 480 ml of dimethyl sulfoxide over 30 minutes during which the temeperature in reaction mixture was controlled between 30° and 40° C. After adding, the solution was cooled to 17°–20° C. 1-Bromooctane (28.95 g) was drowise added to the solution over 30 minutes and the reaction mixture was vigorously stirred for 4 hours at room temperature. The reaction mixture was poured into ice water (1200 ml) and acidified with 40 ml of conc. hydochloric acid. After vigorously stirring for 1 hour, the resulting solid was removed by filtration, and dissolved in 60 ml of acetonitrile. The solution was refluxed for 30 minutes, then was allowed to stand overnight at room temperature to yield 4-octyloxybenzoic acid (13.8 g) as crystals (m.p. 96° C.; Anal: Calcd. for $C_{15}H_{22}O_3$: C 71.97, H 8.86, Found: C 71.30, H 8.89).

To a solution of 4-octyloxybenzoic acid (13.8 g) in diethyl ether (552 ml) were added 2,4,5-trichlorophenol (10.87 g) and N,N'-dicyclohexylcarbodiimide (11.37 g). The solution was stirred under a nitrogen atmosphere for 18 hours at room temperature. The precipitate was removed by filtration, and the filtrate was concentrated in vacuo. The residue was dissolved in petroleum ether and was allowed to stand on ice-water. The resulting crystals (15.2 g) were filtered and dissolved in warm n-hexane (150 ml). After standing overnight at room temperature, the resulting crystals were removed by filtration. The filtrate was concentrated to an oil which was purified by a column chromatography (silica gel) using a mixture of ethyl acetate and n-hexane to give 2,4,5-trichlorophenyl 4-octyloxybenzoate (7.58 g) (m.p. 53° C., Anal: Calcd. for $C_{21}H_{23}O_3Cl_3$:Cl24.75, Found: Cl 24.05).

(2) To a solution of FR133303 substance (2.04 g) in N,N-dimethylformamide (60 ml) were added 2,4,5-trichlorophenyl 4-octyloxybenzoate (2.04 g) and 4-dimethylaminopyridine (0.283 g). The solution was stirred under a nitrogen atmosphere at room temperature for 15 hours. 4-Dimethylaminopyridine (0.20 g) was added to the solution and mixture was stirred for another 24 hours. The reaction mixture was poured into water (600 ml) and the pH was adjusted to 6.0. The mixture was washed twice with an equal volume of ethyl acetate and concentrated to 30 ml. The concentrate was applied on a column (150 ml) of DEAE-TOYOPEARL (Cl type, manufactured by Tosoh). The column was washed with 50% aqueous methanol and developed with 50% aqueous methanol containing 1M aqueous sodium chloride. Product elution was monitored by the same HPLC system as described in Example 1(3) except that the concentration of acetonitrile in the solvent mixture was 40%. The fractions containing the object compound were pooled and evaporated in vacuo to remove methanol. The solution was absorbed on a column (1 L) of YMC GEL ODS-AM 120-S50 in order to remove salt(s). The column was washed with water and eluted with 30% aqueous acetonitrile. The eluate was evaporated in vacuo to remove acetonitrile and lyophilized to give the object compound (hereinafter referred to as FR131535 substance) (1.4 g) as a white powder.

FR131535 substance has following physico-chemical properties:

Appearance:

white powder

Melting point:

170°–189° C. (dec.)

Specific rotation:

$[a]_D^{20}$ −14.4° (C: 10, $H_2O$)

Molecular formula:

$C_{50}H_{71}N_8SO_{22}Na$

Elemental Analysis:

Calcd: for $C_{50}H_{71}N_8SO_{22}NaO6H_2O$: C 46.22, H 6.44, N 8.62, S 2.46, Na 1.77 (%)

Found: C 46.80, H 6.13, N 8.78, S 1.96, Na 1.81 (%)

Solubility:

soluble: methanol, water slightly soluble: acetone insoluble: n-hexane

Color reaction:

positive: iodine vapor reaction, cerium sulfate reaction

Thin layer chromatography (TLC):

| Stationary phase | Developing Solvent | Rf value |
|---|---|---|
| silica gel* | n-butanol:acetic acid: water (6:1:1) | 0.21 |

*SILICA GEL 60 (made by E. Merck)

Ultraviolet absorption spectrum:

$t_{max}^{KBr}$: 3330, 2900, 2850, 1620, 1500, 1430, 1270, 1250, 1170, 1110, 1080, 1040, 960, 940, 880, 840, 800, 750, 710 $cm^{-1}$ $^1H$ Nuclear magnetic resonance spectrum:

($CD_3OD$, 200 MHz)

δ: 7.78 (2H, d, J=8 Hz), 7.31 (1H, d, J=2 Hz), 7.03 (1H, dd, J=2 and 8 Hz), 6.96 (2H, d, J=8 Hz), 6.87 (1H, d, J=8 Hz), 5.33 (1H, d, J=3 Hz), 5.08 (1H, d, J=4 Hz), 4.99 (1H, d, J=3 Hz), 4.80–3.20 (17H, m), 2.83 (1H, m), 2.65–2.30 (4H, m), 2.22–1.90 (2H, m), 1.79 (2H, m), 1.56–1.25 (10H, m), 1.19 (3H, d, J=6 Hz), 1.06 (3H, d, J=6.5 Hz), 0.90 (3H, t, J=6.5 Hz)

The chemical structure of FR131535 substance has been identified and assigned as follows (SEQ ID NO: 1):

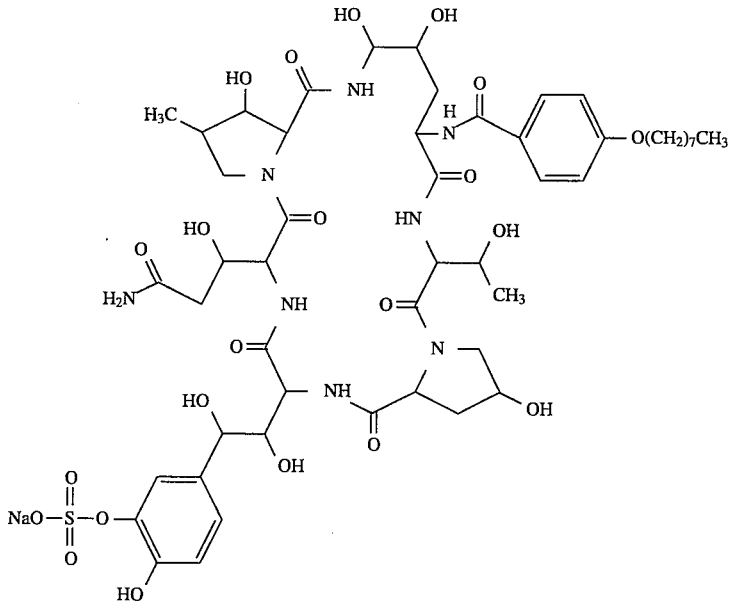

In the following, the structures of the compounds of Examples 3 to 11 are shown.

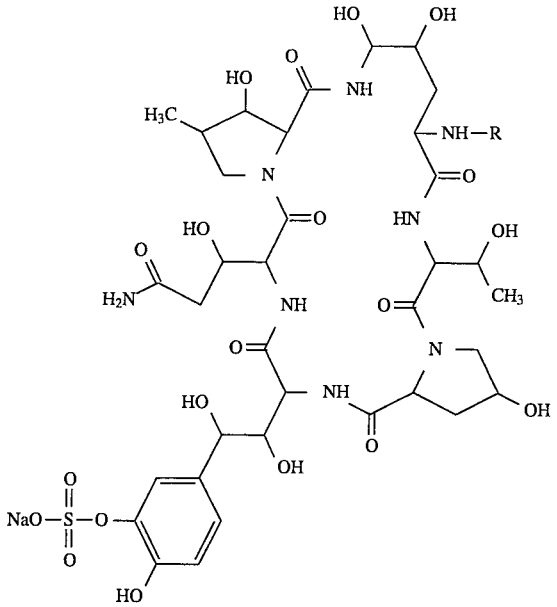

| Example No. | Compound No. | R |
|---|---|---|
| 3 | FR138260 | 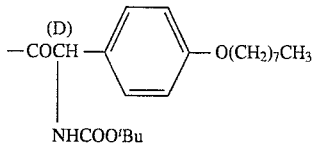 |
| 4 | FR138727 | 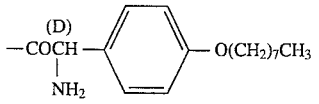 |
| 5 | FR138364 | 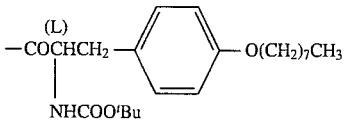 |
| 6 | FR138261 | $-COO^tBu$ |
| 7 | FR138363 | $-COCH_3$ |
| 8 | FR138728 | $-COCH_2Br$ |
| 9 | FR138538 | 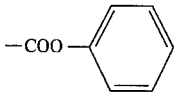 |
| 10 | FR138539 | 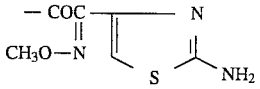 |
| 11 | FR138365 | 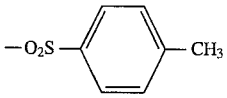 |

EXAMPLE 3

To a solution of FR133303 substance (1 g) and N-(t-butoxycarbonyl)-D-2-(p-octyloxyphenyl)glycine succinimido ester (0.596 g) in N,N-dimethylformamide (3 ml) was added 4-dimethylaminopyridine (0.165 g). The mixture was stirred for 12 hours at room temperature. The reaction mixture was added to water (30 ml), and then the pH was adjusted to 6. The aqueous solution was washed with ethyl acetate, and subjected to ion exchange chromatography on DEAE-TOYOPEARL ($Cl^-$)(60 ml) and eluted with 50% methanol in 1M aqueous sodium chloride. The fractions containing the object compound were combined and evaporated under reduced pressure to remove methanol. The aqueous solution was adjusted to pH 4.5 with 1N hydrochloric acid and subjected to column chromatography on DIAION HP-20 (Trademark, Manufactured by Mitsubishi Chemical Industries) (130 ml) and eluted with 80% aqueous methanol. The fractions containing the object compound were combined and evaporated under reduced preessure to remove methanol. The residue was lyophilized to give the object acylated compound (hereinafter referred to FR138260 substance) (0.77 g).

IR (Nujol): 3300, 1660, 1500, 1240, 1045, 800, 720 $cm^{-1}$

NMR ($CD_3OD$, δ): 0.92 (3H, t, J=6.8 Hz), 1.05 (3H, d, J=6.8 Hz), 1.17–1.33 (13H, m), 1.43 (9H, s), 1.6–1.8 (2H, m), 1.9–2.1 (3H, m), 2.50 (3H, m), 2.75 (1H, dd, J=16 and 4 Hz), 3.35 (1H, m), 3.7–3.8 (1H, m), 3.93 (2H, t, J=6.2 Hz), 3.9–4.2 (5H, m), 4.3–4.5 (5H, m), 4.5–4.7 (3H, m), 4.97 (1H, d, J=3 Hz), 5.05 (1H, d, J=4 Hz), 5.11 (1H, s), 5.30 (1H, d, J=3 Hz), 6.85 (1H, d, J=8.3 Hz), 6.86 (2H, d, J=8.6 Hz), 7.02 (1H, d, J=8.3 Hz), 7.26 (2H, d, J=8.6 Hz), 7.31 (1H, s)

FAB-MS: e/z=1343 (M+Na)

EXAMPLE 4

FR138260 substance obtained in Example 3 (0.25 g) was added to trifluoroacetic acid (1.25 ml) and stirred for 10 minutes. The reaction mixture was added to water (30 ml) and then adjusted to pH 4.5 with a saturated aqueous solution of sodium bicarbonate. The aqueous solution was objected to column chromatography on DIAION HP-20 (100 ml) and eluted with 80% aqueous methanol. The fractions containing the object compound were combined and evaporated under reduced pressure to remove methanol. The residue was lyophilized to give the object compound (hereinafter referred to as FR138727 substance) (15 mg).

NMR ($CD_3OD$, δ): 0.90 (3H, t, J=6.8 Hz), 1.05 (3H, d, J=6.8 Hz), 1.17–1.33 (13H, m), 1.6–1.8 (2H, m), 1.9–2.1 (3H, m), 2.50 (1H, m), 2.75 (1H, dd, J=16 and 4 Hz), 3.40 (1H, m), 3.7–3.8 (1H, m), 3.98 (2H, t, J=6.2 Hz), 3.9–4.2 (5H, m), 4.3–4.5 (5H, m), 4.5–4.7 (3H, m), 4.97 (1H, d, J=3 Hz), 5.06 (1H, s), 5.20 (1H, d, J=3 Hz), 5.40 (1H, d, J=3 Hz), 6.85 (1H, d, J=8.3 Hz), 6.95 (2H, d, J=8.5 Hz), 7.02 (1H, d, J=8.3 Hz), 7.30 (1H, d, J=8.5 Hz), 7.44 (1H, s)

FAB-MS: e/z=1259 (M+K)

EXAMPLE 5

FR138364 substance was obtained by reacting FR133303 substance with $O^4$-octyl-N-(t-butoxycarbonyl)-L-tyrosine succinimido ester according to the procedure of Example 3.

IR (Nujol) : 3300, 1660, 1620, 1240, 1050 $cm^{-1}$

NMR ($CD_3OD$, δ): 0.904 (3H, t, J=6.8 Hz), 1.06 (3H, d, J=6.8 Hz), 1.17 (3H, d, J=6.7 Hz), 1.20–1.30 (10H, m), 1.35 (9H, s), 1.74 (2H, quintet, J=6.5 Hz), 1.9–2.1 (3H, m), 2.45 (3H, m), 2.76 (1H, dd, J=16 and 4 Hz), 3.0–3.1 (2H, m), 3.37 (1H, m), 3.77 (1H, d, J=11 Hz), 3.92 (2H, t, J=6.8 Hz), 3.9–4.2 (7H, m), 4.3–4.5 (5H, m), 4.5–4.6 (3H, m), 4.94 (1H, d, J=3 Hz), 5.05 (1H, d, J=3.8 Hz), 5.31 (1H, d, J=3 Hz), 6.79 (2H, d, J=8.5 Hz), 6.85 (1H, d, J=8.3 Hz), 7.03 (1H, dd, J=8.3 and 2 Hz), 7.12 (2H, d, J=8.5 Hz), 7.31 (1H, d, J=2 Hz)

FAB-MS: e/z=1357 (M+Na)

EXAMPLE 6

A solution of FR133303 substance (0.5 g) in a mixture of water (5 ml) and tetrahydrofuran (5 ml) was adjusted to pH 7 with saturated aqueous sodium bicarbonate, and N,N-di-t-butylcarbonate (0.114 g) was added thereto at room temperature. The mixture was stirred for 5 hours at room temperature, maintaining pH 7 with saturated aqueous sodium bicarbonate. The reaction mixture was added to water and adjusted to pH 6. The aqueous solution was washed with ethyl acetate, and subjected to ion exchange chromatography an DEAE-TOYOPEARL ($Cl^{\theta}$) (30 ml), eluting with 50% methanol in 1M aqueous sodium chloride. The fractions containing the object compound were combined and evaporated under reduced pressure to remove methanol. The aqueous solution was adjusted to pH 4.5 with 1N hydrochloric acid and subjected to column chromatography on DIAION HP-20 (100 ml), eluting with 80% aqueous methanol. The fractions containing the object compound were combined and evaporated under reduced pressure to remove methanol. The residue was lyophilized to give the object acylated compound (hereinafter referred to as FR138261 substance) (0.145 g).

IR (Nujol): 3300, 1660, 1620, 1240, 1050 $cm^{-1}$

NMR ($CD_3OD$, δ): 1.06 (3H, d, J=6.8 Hz), 1.18 (3H, d, J=6.0 Hz), 1.40 (9H, s), 1.9–2.1 (3H, m), 2.44 (3H, m), 2.82 (1H, dd, J=16 and 4 Hz), 3.37 (1H, m), 3.75 (1H, d, J=11 Hz), 3.89–4 (2H, m), 4.10 (1H, m), 4.15 (1H, m), 4.29 (1H, dd, J=6 and 2 Hz), 4.36–4.45 (5H, m), 4.5–4.6 (3H, m), 4.97 (1H, d, J=3 Hz), 5.06 (1H, dd, J=8.2 and 4 Hz), 5.33 (1H, d, J=3 Hz), 6.85 (1H, d, J=8.3 Hz), 7.03 (1H, dd, J=8.3 and 2 Hz), 7.30 (1H, d, J=2 Hz), 7.50 (1H, d, J=8.2 Hz)

FAB-MS: e/z=1081 (M+Na)

EXAMPLE 7

FR138363 substance was obtained by reacting FR133303 substance with acetyl chloride according to the procedure of Example 6.

IR (Nujol): 3300, 1620, 1250, 1040 $cm^{-1}$

NMR ($CD_3OD$, δ): 1.06 (3H, d, J=6.8 Hz), 1.20 (3H, d, J=6 Hz), 1.78–2.05 (3H, m), 1.96 (3H, s), 2.21–2.54 (3H, m), 2.95 (1H, m), 3.35–3.42 ( 1H, m), 3.58–4.42 ( 11H, m), 4.50–5.05 (5H, m), 5.23 (1H, m), 6.88 (1H, d, J=8.3 Hz), 7.05 (1H, dd, J=8.3 and 2 Hz), 7.35 (1H, d, J=2 Hz)

FAB-MS: 1023 (M+Na)

EXAMPLE 8

FR138728 substance was obtained by reacting FR133303 substance with 2-bromoacetyl chloride according to the procedure of Example 6.

IR (Nujol): 3300, 1660, 1620, 1500, 1220, 1040 $cm^{-1}$

NMR ($CD_3OD$, δ): 1.06 (3H, d, J=6.9 Hz), 1.17 (3H, d, J=6.1 Hz), 1.9–2.1 (3H, m), 2.50 (3H, m), 2.80 (1H, dd, J=16 and 4 Hz), 3.37 (1H, m), 3.6–4.0 (5H, m), 4.09 (1H, m), 4.16 (1H, m), 4.29 (1H, dd, J=6 and 2 Hz), 4.36–4.45 (5H, m), 4.5–4.7 (3H, m), 4.97 (1H, d, J=3 Hz), 5.04 (1H, dd, J=8.6 and 4 Hz), 5.25 (1H, d, J=3.1 Hz), 6.85 (1H, d, J=8.3 Hz), 7.03 (1H, dd, J=8.3 and 2.1 Hz), 7.31 (1H, d, J=2 Hz), 7.52 (1H, d, J=8.6 Hz)

FAB-MS: e/z =1103 (M+Na)

EXAMPLE 9

FR138538 substance was obtained by reacting FR133303 substance with benzoyl chloride according to the procedure of Example 6.

IR (Nujol): 3300, 1640, 1240 $cm^{-1}$

NMR ($CD_3OD$, δ): 1.05 (3H, d, J=6.8 Hz), 1.18 (3H, d, J=6 Hz), 1.89–2.12 (3H, m), 2.31–2.53 (3H, m), 2.75 (1H, dd, J=12 and 4 Hz), 3.38 (1H, m), 3.76 (1H, d, J=11 Hz), 3.87–3.98 (1H, m), 4.02–4.18 (2H, m), 4.22–4.32 (4H, m), 4.37–4.40 (3H, m), 4.49–4.62 (3H, m), 4.98 (1H, m), 5.02 (1H, m), 5.37 (1H, d, J=3 Hz), 6.85 (1H, d, J=8.3 Hz), 7.04 (1H, dd, J=8.3 and 2.1 Hz), 7.11–7.50 (6H, m)

FAB-MS e/z=1101 (M+Na)

EXAMPLE 10

FR138539 substance was obtained by reacting FR133303 substance with 2-(2-aminothiazol-4-yl)-2-thoxyiminoacetic acid according to the procedure of Example 6.

IR (Nujol): 3300, 1650, 1620, 1520, 12600, 1040 $cm^{-1}$

NMR ($CD_3OD$, δ): 1.05 (3H, d, J=6.8 Hz), 1.21 (3H, d, J=5.9 Hz), 1.89–2.21 (3H, m), 2.29–2.61-(3H, m), 2.78–2.89 (1H, m), 3.32–3.42 (1H, m), 3.76–3.82 (1H, m), 3.91–4.01 (2H, m), 3.95 (3H, s), 4.13 (1H, m), 4.16 (1H, m), 4.24–4.27 (1H, m), 4.32–4.43 (5H, m), 4.46–4.62 (3H, m), 4.97–4.99 (1H, m), 5.08 (1H, m), 5.41 (1H, m), 6.79 (1H, s), 6.86 (1H, d, J=8.1 Hz), 7.04 (1H, dd, J=8.1 and 2 Hz), 7.31 (1H, d, J=2 Hz), 7.51 (1H, d, J=7 Hz)

FAB-MS: e/z=1143 ($M^+$)

EXAMPLE 11

FR138365 substance was obtained by reacting FR133303 substance with tosyl chloride according to the procedure of Example 6.

IR (Nujol): 3300, 1650, 1620, 1260, 1060 $cm^{-1}$

NMR ($CD_3OD$, δ): 0.75 (3H, d, J=6.8 Hz), 1.07 (3H, d, J=6.0 Hz), 1.61–1.79 (1H, m), 1.91–2.05 (3H, m), 2.30–2.59 (3H, m), 3.36 (1H, m), 3.68 (1H, d, J=11 Hz), 3.81–4.07 (4H, m), 4.22 (1H, m), 4.32–4.40 (5H, m), 4.42–4.60 (3H, m), 4.7 (1H, m), 5.0 (1H, m), 5.42 (1H, d, J=3 Hz), 6.85 (1H d, J=8.3 Hz), 7.03 (1H, dd, J=8.3 and 2 Hz), 7.29–7.33 (3H, m), 7.75 (1H, d, J=8.3 Hz)

FAB-MS: e/z=1135 (M+Na)

Preparation 11

To a solution of 6-hydroxy-2-naphthoic acid (1 g) in the mixture of 10% aqueous sodium hydroxide (4.25 ml) and dimethylsulfoxide (17 ml) was added octyl bromide (0.918 ml). The mixture was stirred for 6 hours at 60° C.

The reaction mixture was added to a mixture of water and ethyl acetate and adjusted to pH 3 with conc. hydrochloric acid. The organic layer was separated and dried over magnesium sulfate. The magnesium sulfate was filtered off, and the filtrate was evaporated under reduced pressure to give 6-octyloxy-2-naphthoic acid (0.91 g).

IR (Nujol): 1670, 1620, 1210 $cm^{-1}$

NMR (DMSO-$d_6$, δ): 0.86 (3H, t, J=6.7 Hz), 1.2–1.6 (10H, m), 1.78 (2H, m), 4.10 (2H, t, J=6.7 Hz), 7.19 (1H, dd, J=2.3 and 8.8 Hz), 7.36 (1H, d, J=2.3 Hz), 7.83 (1H, d, J=8.8 Hz), 7.97 (2H, d, J=8.8 Hz), 8.52 (1H, s)

Preparation 12

1-Ethyl-3-(3-dimethylaminopropyl)carbodiimide hydrochloride (0.703 g) was added to a solution of 6-octyloxy-2-naphthoic acid (0.85 g) and 1-hydroxy-1H-benzotriazole (0.382 g) in ethyl acetate (26 ml). The mixture was stirred for two hours at room temperature.

The reaction mixture was added to water and the separated organic layer was washed with water and aqueous sodium chloride. The organic layer was then dried over magnesium sulfate. The magnesium sulfate was filtered off, and the filtrate was evaporated under reduced pressure to give 3-(6-octyloxy-2-naphthoyl)-1H-benzotriazole-3-oxide (0.74 g).

IR (Nujol): 1770, 1740, 1620, 1190, 1020, 740 $cm^{-1}$

NMR ($CDCl_3$, δ): 0.90 (3H, t, J=6.8 Hz), 1.2–1.6 (10H, m), 1.89 (2H, m), 4.14 (2H, t, J=6.8 Hz), 7.1–7.3 (2H, m), 7.4–7.6 (3H, m), 7.8–8.0 (2H, m), 8.1–8.2 (2H, m), 8.80 (1H, s)

In the following, the structure of the compound of Example 12 is shown (SEQ ID NO: 1):

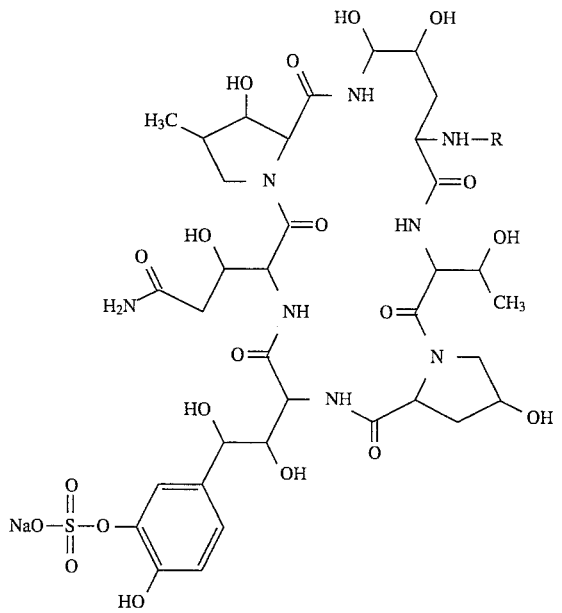

| Example No. | Compound No. | R |
|---|---|---|
| 12 | FR139687 | 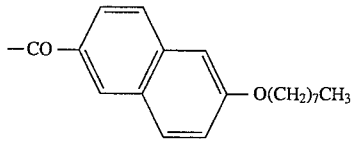 |

EXAMPLE 12

To a solution of FR133303 substance (0.5 g) and 1-(6-octyloxy-2-naphthoyl)-1H-benzotriazole-3-oxide (0.271 g) in N,N-dimethylformamide (1.5 ml) was added 4-dimethylaminopyridine (0.0828 g). The mixture was stirred for 12 hours at room temperature.

The reaction mixture was added to water and adjusted to pH 6. The aqueous solution was washed with ethyl acetate, and subjected to ion exchange chromatography on DEAE-TOYOPEARL ($Cl^-$) (30 ml) and eluted with 50% methanol in 1M sodium chloride solution. The fractions containing the object compound were combined and evaporated under reduced pressure to remove methanol. The aqueous solution was adjusted to pH 4.5 with 1 N hydrochloric acid and subjected to column chromatography on DIAION HP-20 (65 ml), eluting with 80% aqueous methanol. The fractions containing the object compound were combined and evaporated under reduced pressure to remove methanol. The residue was lyophilized to give the object acylated compound (hereinafter referred to as FR139687 substance) (0.214 g).

IR (Nujol): 3300, 1620, 1500 $cm^{-1}$

NMR (DMSO-$d_6$+$D_2O$, δ): 0.86 (3H, t, J=6.8 Hz), 0.97 (3H, d, J=6.8 Hz), 1.06 (3H, d, J=6.8 Hz), 1.21.5 (10H, m), 1.6 2.0 (5H, m), 2.2–2.5 (3H, m), 2.4–2.6 (1H, m), 3.18 (1H, m), 3.6–3.9 1H, m), 4.0–4.6 (15H, m), 4.84 (1H, d, J=3 Hz), 4.90 (1H, d, J=3 Hz), 5.11 (1H, d, J=3 Hz), 6.76 (1H, d, J=8.3 Hz), 6.93 (1H, d, J=8.3 Hz), 7.13 (1H, s), 7.25 (1H, d, J=8.3 Hz), 7.39 (1H,,s), 7.8–8.0 (3H, m), 8.44 (1H, s)

FAB-MS e/z=1264 (M+Na)

The following compounds (Preparations 13 to 16) were obtained according to methods similar to that of Preparation 5.

Preparation 13

N-(t-Butoxycarbonyl)-L-2-(2-naphthyl)glycine succinimido ester

IR (Nujol): 3350, 1800, 1770, 1730, 1680, 1500, 1200 $cm^{-1}$

Preparation 14

Succinimido 2-(4-biphenylyl)acetate

IR (Nujol): 1800, 1770, 1720, 1200 $cm^{-1}$

NMR (DMSO-$d_6$, δ): 2.82 (4H, s), 4.17 (2H, s), 7.30–7.50 (5H, m), 7.45 (2H, d, J=8.1 Hz), 7.67 (2H, d, J=8.1 Hz)

Preparation 15

Succinimido 4-t-butylbenzoate

IR (Nujol): 1760, 1730, 1200, 1070, 990 $cm^{-1}$

NMR (DMSO-$d_6$, δ): 1.33 (9H, s), 2.89 (4H, s), 7.68 (2H, d, J=8.5 Hz), 8.03 (2H, d, J=8.5 Hz)

Preparation 16

Succinimido 4- (4-phenylbutoxy)benzoate

IR (Nujol): 1730, 1600, 1240, 1170, 1070 $cm^{-1}$

NMR (DMSO-$d_6$, δ): 1.75 (4H, m), 2.65 (2H, m), 4.14 (2H, m), 7.15 (2H, d, J=8.9 Hz), 7.13–7.35 (5H, m), 8.03 (2H, d, J=8.9 Hz)

Preparation 17

To neat 3,7-dimethyloctanol (5 ml) was added phosphorus tribromide (1.01 ml). The mixture was stirred for 4 hours at 60° C. The reaction mixture was added to a mixture of water and n-hexane. The organic layer was separated and dried over magnesium sulfate. The magnesium sulfate was filtered off, and the filtrate was evaporated under reduced pressure to give 3,7-dimethyloctyl bromide (4.40 g).

IR (Neat): 2900, 1450 $cm^{-1}$

NMR ($CDCl_3$, δ): 0.87 (6H, d, J=6.6 Hz), 0.89 (3H, d, J=6.4 Hz), 1.1–1.3 (6H, m), 1.5–1.9 (4H, m), 3.3–3.5 (2H, m)

The following compounds (Preparations 18 to 23) were obtained according to methods similar to that of Preparation 11.

Preparation 18

4-[4-(Octyloxy) phenoxy]benzoic acid

IR (Nujol): 1680, 1600, 1240, 840 $cm^{-1}$

NMR (DMSO-$d_6$, δ): 0.87 (3H, t, J=6.7 Hz), 1.1–1.6 (10H, m), 1.71 (2H, m), 3.96 (2H, t, J=6.4 Hz), 6.9–7.1 (6H, m), 7.92 (2H, d, J=8.7 Hz), 12.8 (1H, br s)

Preparation 19

6-(Butoxy)-2-naphthoic acid

IR (Nujol): 1660, 1610, 1205 $cm^{-1}$

NMR (DMSO-$d_6$, δ): 0.96 (3H, t, J=7.29 Hz), 1.48 (2H, qt, J=7.29 and 7 Hz), 1.78 (2H, tt, J=7 and 6.45 Hz), 4.12 (2H, t, J=6.45 Hz), 7.24 (1H, dd, J=9.0 and 2.3 Hz), 7.40 (1H, d, J=2.3 Hz), 7.86 (1H, d, J=8.7 Hz), 7.94 (1H, d, J=8.7 Hz), 8.01 (1H, d, J=9.0 Hz), 8.52 (1H, s)

Preparation 20

6-Decyloxy-2-naphthoic acid

IR (Nujol): 1670, 1620, 1210 $cm^{-1}$

NMR (DMSO-$d_6$, δ): 0.85 (3H, t, J=6.7 Hz), 1.2–1.6 (14H, m), 1.78 (2H, m), 4.11 (2H, t, J=6.4 Hz), 7.23 (1H, dd, J=8.9 and 2.4 Hz), 7.39 (1H, d, J=2.4 Hz), 7.86 (1H, d, J=8.7 Hz), 7.93 (1H, d, J=8.7 Hz), 8.01 (1H, d, J=8.9 Hz), 8.5 (1H, s)

Preparation 21

6-Hexyloxy-2-naphthoic acid

IR (Nujol): 1660, 1620, 1290, 1210 $cm^{31\ 1}$

NMR (DMSO-$d_6$, δ): 0.89 (3H, t, J=6.8 Hz), 1.2–1.6 (6H, m), 1.78 (2H, quintet, J=6.5 Hz), 4.11 (2H, t, J=6.5 Hz), 7.23 (1H, dd, J=9.0 Hz and 2.4 Hz), 7.39 (1H, d, J=2.4 Hz), 7.86 (1H, d, J=8.7 Hz), 7.94 (1H, d, J=8.7 Hz), 8.01 (1H, d, J=9.0 Hz), 8.52 (1H, s)

Preparation 22

6-Dodecyloxy-2-naphthoic acid

IR (Nujol): 1670, 1620, 1210 $cm^{-1}$

NMR (DMSO-$d_6$, δ): 0.85 (3H, t, J=6.7 Hz), 1.20–1.60 (18H, m), 1.78 (2H, m), 4.11 (2H, t, J=6.5 Hz), 7.22 (1H, dd, J=9.0 and 2.4 Hz), 7.39 (1H, d, J=2.4 Hz), 7.85 (1H, d, J=8.7 Hz), 7.93 (1H, d, J=8.7 Hz), 8.00 (1H, d, J=9.0 Hz), 8.51 (1H, S), 12.90 (1H, s)

Preparation 23

6-(3,7-Dimethyloctyloxy)-2-naphthoic acid

IR (Nujol): 1660, 1610, 1290, 1210 $cm^{-1}$

NMR (DMSO-$d_6$, δ): 0.84 (6H, d, J=6.6 Hz), 0.94 (3H, d, J=6.1 Hz), 1.1–1.4 (6H, m), 1.4–1.9 (4H, m), 4.15 (2H, t, J=6.7 Hz), 7.22 (1H, dd, J=9.0 and 2.4 Hz), 7.41 (1H, d, J=2.4 Hz), 7.86 (1H, d, J=8.6 Hz), 7.93 (1H, d, J=8.6 Hz), 8.01 (1H, d, J=9.0 Hz), 8.52 (1H, s)

The following compounds (Preparations 24 to 31) were obtained according to methods similar to that of Preparation 12.

Preparation 24

1-[4-(4-octyloxy)phenoxy]benzoyl-1H-benzotriazole-3-oxide

IR (Nujol): 1770, 1730, 1600, 1500, 1230, 980 $cm^{-1}$

Preparation 25

1-(6-Butoxy-2-naphthoyl)-1H-benzotriazole-3-oxide

IR (Nujol): 1760, 1610, 1260, 1180, 1020 $cm^{-1}$

Preparation 26

1-(6-Decyloxy-2-naphthoyl)-1H-benzotriazole-3-oxide

IR (Nujol): 1780, 1620, 1190, 1000 $cm^{-1}$

Preparation 27

1-(6-Hexyloxy-2-naphthoyl)-1H-benzotriazole-3-oxide

IR (Nujol): 1780, 1610, 1190 $cm^{-1}$

NMR (DMSO-$d_6$, δ): 0.89 (3H, t, J=6.7 Hz), 1.2–1.6 (6H, m), 1.79 (2H, m), 4.12 (2H, t, J=6.5 Hz), 7.24 (1H, dd, J=9.0 and 2.4 Hz), 7.39 (1H, d, J=2.4 Hz), 7.41 (1H, t, J=8 Hz), 7.54 (1H, t, J=8 Hz), 7.72 (1H, d, J=8 Hz), 7.88 (1H, d, J=8.7 Hz), 7.90 (1H, d, J=8.7 Hz), 7.97 (1H, d, J=8 Hz), 8.02 (1H, d, J=9.0 Hz), 8.51 (1H, s)

Preparation 28

1-(6-Dodecyloxy-2-naphthoyl)-1H-benzotriazole-3-oxide

IR (Nujol): 1770, 1620, 1190, 1030, 730 $cm^{-1}$

NMR (DMSO-$d_6$, δ): 0.85 (3H, t, J=6.7 Hz), 1.2–1.3 (18H, m), 1.78 (2H, m), 4.11 (2H, t, J=6.5 Hz), 7.22 (1H, dd, J=9.0 and 2.4 Hz), 7.39 (1H, d, J=2.4 Hz), 7.40 (1H, t, J=8 Hz), 7.55 (1H, t, J=8 Hz), 7.73 (1H, d, J=8 Hz), 7.85 (1H, d, J=8.7 Hz), 7.93 (1H, d, J=8.7 Hz), 7.99 (1H, d, J=8 Hz), 8.00 (1H, d, J=9.0 Hz), 8.51 (1H, s)

Preparation 29

1-[6-(3,7-Dimethyloctyloxy)-2-naphthoyl]-1H-benzotriazole-3-oxide

IR (Nujol): 1780, 1620, 1190 $cm^{-1}$

Preparation 30

1-[(2E,6E)-3,7,11-Trimethyl-2,6,10-dodecatrienoyl]-1H-benzotriazole-3-oxide

IR (Neat): 2900, 1780, 1620, 1420, 1070 $cm^{-1}$

Preparation 31

3,7-Dimethyl-6-octenyl bromide was obtained according to the method of Preparation 17.

IR (Neat): 2900, 1440, 1380 $cm^{-1}$

NMR (DMSO-$d_6$, δ): 0.86 (3H, d, J=6.3 Hz), 1.0–1.5 (2H, m), 1.57 (3H, s), 1.65 (3H, s), 1.7–2.1 (5H, m), 3.4–3.7 (2H, m), 5.08 (1H, m)

Preparation 32

To a suspension of sodium hydride (2.04 g) in N,N-dimethylformamide (50 ml) was added 4-hydroxypyridine (5 g) at room temperature. Octyl bromide (9.08 ml) was added thereto. The mixture was stirred for 2 hours at 50° C. The reaction mixture was added to a mixture of brine (100 ml), tetrahydrofuran (100 ml) and ethyl acetate (100 ml). The organic layer was separated and dried over magnesium sulfate. The magnesium sulfate was filtered off, and the filtrate was evaporated under reduced pressure to give 1-octyl-4-pyridone (14.7 g).

NMR (DMSO-$d_6$, δ): 0.86 (3H, t, J=6 Hz), 1.1–1.4 (10H, m), 1.4–1.8 (2H, m), 3.81 (2H, t, J=7 Hz), 6.05 (2H, d, J=8 Hz), 7.63 (2H, d, J=8 Hz)

Preparation 33

To a solution of 1-octyl-4-pyridone (10.9 g) in pyridine (100 ml) was added phosphorous pentasulfide (8.65 g) at room temperature. The mixture was stirred for 3 hours at 80° C. The reaction mixture was added to a mixture of water (200 ml) and methylene chloride (200 ml). The organic layer was separated and dried over magnesium sulfate. The magnesium sulfate was filtered off, and the filtrate was evaporated under reduced pressure to give 1-octyl-1,4-dihydropyridine-4-thione (5.27 g).

IR (Neat): 2910, 2850, 1620, 1460, 1110 $cm^{-1}$

NMR (DMSO-$d_6$, δ): 0.86 (3H, t, J=6 Hz), 1.1–1.4 (10H, m), 1.5–1.9 (2H, m), 3.95 (2H, t, J=7 Hz), 7.13 (2H, d, J=7 Hz), 7.60 (2H, d, J=7 Hz)

The following compounds (Preparations 34 to 36) were obtained according to methods similar to that of Preparation 1.

Preparation 34

Methyl 2-(4 -hydroxyphenyl)-2-methoxyacetate

IR (Nujol): 3350, 1740, 1610, 1600, 1220, 1100 $cm^{-1}$

NMR (DMSO-$d_6$, δ): 3.23 (3H, s) , 3.60 (3H, s) , 4.73 (1H, s), 6.72 (2H, d, J=8.9 Hz), 7.15 (2H, d, J=8.9 Hz)

EI-MS (e/z)=196 ($M^+$)

Preparation 35

D-Tyrosine methyl ester hydrochloride

IR (Nujol): 3300, 1740, 1220 $cm^{-1}$

NMR (DMSO-$d_6$, δ): 3.02 (2H, m), 3.67 (3H, s), 4.16 (1H, t, J=6.7 Hz), 6.72 (2H, d, J=8.4 Hz), 7.01 (2H, d, J=8.4 Hz), 8.58 (2H, s), 9.47 (1H, s)

Preparation 36

Methyl (4 -hydroxyphenyl)glyoxylate

IR (Nujol): 3380, 1730, 1700, 1600, 1580, 1220 $cm^{-1}$

NMR (DMSO-$d_6$, δ): 3.91 (3H, s), 6.94 (2H, d, J=8.8 Hz), 7.83 (2H, d, J=8.8 Hz), 10.9 (1H, s)

Preparation 37

N-(t-Butoxycarbonyl)-D-tyrosine methyl ester was obtained according to the method of Preparation 2.

IR (Nujol): 3360, 1700, 1680, 1290, 1270, 1250 $cm^{-1}$

NMR (DMSO-$d_6$, δ): 1.33 (9H, s), 2.73 (2H, m), 3.59 (3H, s), 4.05 (1H, m), 6.65 (2H, d, J=8.4 Hz), 7.00 (2H, d, J=8.4 Hz), 7.23 (1H, d, J=7.9 Hz), 9.23 (1H, s)

Preparation 38

To a solution of L-tyrosine methyl ester hydrochloride (1 g) in water (1.5 ml) was added sodium bicarbonate (0.363 g) under ice-cooling. The mixture was stirred for 10 minutes, and then acetonitrile (7 ml), 37% aqueous formaldehyde (0.637 ml) and sodium cyanoborohydride (0.182 g) were added thereto at –5° C. The mixture was stirred for 2 hours at –5° C. The resultant insoluble material was filtered off, and the filtrate was extracted with ethyl acetate. The organic layer was separated and dried over magnesium sulfate. The magnesium sulfate was filtered off, and the filtrate was evaporated under reduced pressure to give N,N-dimethyl-L-tyrosine methyl ester (0.21 g) .

IR (Nujol): 1730, 1260, 1010 $cm^{-1}$

NMR (DMSO-$d_6$, δ): 2.24 (6H, s), 2.72 (2H, m), 3.34 (1H, m), 3.53 (3H, s), 6.64 (2H, d, J=8.4 Hz), 6.97 (2H, d, J=8.4 Hz), 9.18 (1H, s)

The following compounds (Preparations 39 to 44) were obtained according to methods similar to that of Preparation 3.

Preparation 39

Methyl 2-(4 -octyloxyphenyl)acetate

IR (Neat): 2910, 2850, 1730, 1240 $cm^{-1}$

NMR (DMSO-$d_6$, δ): 0.86 (3H, t, J=6.3 Hz), 1.2–1.5 (10H, m), 1.6–1.9 (2H, m), 3.58 (2H, s), 3.59 (3H, s), 3.92 (2H, t, J=6.4 Hz), 6.85 (2H, d, J=8.7 Hz), 7.15 (2H, d, J=8.7 Hz)

Preparation 40

Ethyl 3-(4-octyloxyphenyl)propionate

IR (Neat): 2920, 2850, 1730, 1240 $cm^{-1}$

NMR (DMSO-$d_6$, δ): 0.86 (3H, t, J=6.7 Hz), 1.15 (3H, t, J=7.1 Hz), 1.2–1.5 (10H, m), 1.6–1.8 (2H, m), 2.55 (2H, t, J=7.2 Hz), 2.77 (2H, t, J=7.2 Hz), 3.90 (2H, t, J=6.4 Hz), 4.03 (2H, q, J=7.1 Hz), 6.81 (2H, d, J=8.6 Hz), 7.11 (2H, d, J=8.6 Hz)

Preparation 41

Methyl 2-(4-octyloxyphenyl)-2-methoxyacetate

IR (Neat): 2910, 2850, 1740, 1600, 1240, 1100 $cm^{-1}$

NMR (DMSO-$d_6$, δ): 0.86 (3H, t, J=6.8 Hz), 1.2–1.5 (10H, m), 1.6–1.8 (2H, m), 3.26 (3H, s), 3.62 (3H, s), 3.94 (2H, t, J=6.4 Hz), 4.83 (1H, s), 6.91 (2H, d, J=8.7 Hz), 7.27 (2H, d, J=8.7 Hz)

EI-MS (e/z)=308 ($M^+$)

Preparation 42

$O^4$-Octyl-N-(t-butoxycarbonyl)-D-tyrosine methyl ester

IR (Nujol): 3350, 1730, 1680, 1510, 1240, 1160 $cm^{-1}$

NMR (DMSO-$d_6$, δ): 0.86 (3H, t, J=6.7 Hz), 1.2–1.3 (10H, m), 1.68 (2H, m), 2.82 (2H, m), 3.60 (3H, s), 3.91 (2H, t, J=7.3 Hz), 4.08 (1H, m), 6.81 (2H, d, J=8.6 Hz), 7.12 (2H, d, J=8.6 Hz), 7.25 (1H, d, J=8.0 Hz)

Preparation 43

$O^4$-Octyl-N,N-dimethyl-L-tyrosine methyl ester

IR (Neat): 2930, 2860, 1730, 1250 $cm^{-1}$

NMR (DMSO-$d_6$, δ): 0.86 (3H, t, J=6.6 Hz), 1.26 (10H, m), 1.68 (2H, m), 2.80 (2H, m), 3.33 (6H, s), 3.37 (1H, m), 3.53 (3H, s), 3.89 (2H, t, J=6.4 Hz), 6.79 (2H, d, J=8.6 Hz) , 7.08 (2H, d, J=8.6 Hz)

Preparation 44

Methyl (4-octyloxyphenyl)glyoxylate

IR (Neat): 2930, 2850, 1730, 1670, 1600, 1260, 1210, 1160 $cm^{-1}$

NMR (DMSO-$d_6$, δ): 0.86 (3H, t, J=6.3 Hz), 1.2–1.5 (10H, m), 1.6–1.9 (2H, m), 3.93 (3H, s), 4.10 (2H, t, J=6.5 Hz), 7.12 (2H, d, J=8.9 Hz), 7.92 (2H, d, J=8.9 Hz)

The following compounds (Preparations 45 to 51) were obtained according to methods similar to that of Preparation 4.

Preparation 45

4-(2-Butoxyethoxy)benzoic acid

IR (Nujol): 1670, 1610, 1260 $cm^{-1}$

NMR (DMSO-$d_6$, δ): 0.87 (3H, t, J=7.2 Hz), 1.2–1.6 (4H, m), 3.45 (2H, t, J=6.4 Hz), 3.70 (2H, t, J=4.4 Hz), 4.16 (2H, t, J=4.4 Hz), 7.02 (2H, d, J=8.9 Hz), 7.88 (2H, d, J=8.9 Hz), 12.63 (1H, s)

Preparation 46

2-(4-Octyloxyphenyl)acetic acid

IR (Nujol): 1680, 1240, 820, 780 $cm^{-1}$

NMR (DMSO-$d_6$, δ): 0.86 (3H, t, J=6.8 Hz), 1.1–1.5 (10H, m), 1.6–1.8 (2H, m), 3.47 (2H, s), 3.92 (2H, t, J=6.4 Hz), 6.84 (2H, d, J=8.6 Hz), 7.14 (2H, d, J=8.6 Hz)

Preparation 47

3-(4-Octyloxyphenyl)propionic acid

IR (Nujol): 1680, 1500, 1200 $cm^{-1}$

NMR (DMSO-$d_6$, δ): 0.86 (3H, t, J=6.3 Hz), 1.1–1.5 (10H, m), 1.6–1.8 (2H, m), 2.47 (2H, t, J=7.2 Hz), 2.74 (2H, t, J=7.2 Hz), 3.90 (2H, t, J=6.4 Hz), 6.81 (2H, d, J=8.6 Hz), 7.11 (2H, d, J=8.6 Hz), 12.10 (1H, br s)

Preparation 48

2-(4-Octyloxyphenyl)-2-methoxyacetic acid

IR (Nujol): 1760, 1720, 1600, 1500, 1240, 1180, 1100, 830 $cm^{-1}$

NMR (DMSO-$d_6$, δ): 0.86 (3H, t, J=6.7 Hz), 1.2–1.5 (10H, m), 2.6–2.8 (2H, m), 3.26 (3H, s), 3.94 (2H, t, J=6.4 Hz), 4.67 (1H, s), 6.90 (2H, d, J=8.6 Hz), 7.27 (2H, d, J=8.6 Hz)

Preparation 49

$O^4$-Octyl-N-(t-butoxycarbonyl)-D-tyrosine

IR (Nujol): 3400–2900, 1700, 1500, 1240, 1160 $cm^{-1}$

NMR (DMSO-$d_6$, δ): 0.859 (3H, t, J=6.8 Hz), 1.20–1.30 (10H, m), 1.32 (9H, s), 1.68 (2H, m), 2.67–2.95 (1H, m), 3.90 (2H, t, J=7 Hz), 4.01 (1H, m), 6.81 (2H, d, J=8.6 Hz), 7.02 (1H, d, J=8.3 Hz), 7.13 (2H, d, J=8.6 Hz)

Preparation 50

$O^4$-Octyl-N,N-dimethyl-L-tyrosine

IR (Neat): 2940, 2860, 2600, 1620, 1240 $cm^{-1}$

NMR (DMSO-$d_6$, δ): 0.86 (3H, t, J=6.6 Hz), 1.26 (10H, m), 1.68 (2H, m), 2.67 (6H, s), 2.8–3.6 (3H, m), 3.91 (2H, t, J=6.4 Hz), 6.85 (2H, d, J=8.5 Hz), 7.16 (2H, d, J=8.5 Hz)

Preparation 51

$O^4$-Octyloxyphenylglyoxylic acid

IR (Neat): 1730, 1670, 1600, 1260, 1160 $cm^{-1}$

NMR (DMSO-$d_6$, δ): 0.86 (3H, t, J=6.8 Hz), 1.2–1.5 (10H, m), 1.65–1.85 (2H, m), 4.09 (2H, t, J=6.5 Hz), 7.12 (2H, d, J=8.9 Hz), 7.89 (2H, d, J=8.9 Hz)

Preparation 52

$N^{\tau}$-Octyl-N-(t-butoxycarbonyl)-L-histidine was obtained from N-(t-butoxycarbonyl)-L-histidine methyl ester according to a procedure similar to those of Preparations 3 and 4.

NMR (DMSO-$d_6$, δ): 0.85 (3H, t, J=6.3 Hz), 1.23 (10H, m), 1.35 (9H, s), 2.83 (2H, m), 3.90 (2H, t, J=7 Hz), 4.0–4.2 (1H, m), 6.36 (1H, s), 7.02 (1H, d, J=8 Hz), 7.75 (1H, s)

The following compounds (Preparations 53 to 60) were obtained according to procedures similar to that of Preparation 11.

Preparation 53

4-Octyloxyphthalic acid

IR (Neat): 2930, 2860, 2500, 1700, 1600, 1260 $cm^{-1}$

NMR (DMSO-$d_6$, δ): 0.86 (3H, t, J=6.8 Hz), 1.2–1.5 (10H, m), 1.5–1.8 (2H, m), 4.05 (2H, t, J=6.2 Hz), 7.03 (1H, d, J=2.6 Hz), 7.06 (1H, dd, J=8.4 and 2.6 Hz), 7.72 (1H, d, J=8.4 Hz)

Preparation 54

3-Methoxy-4-octyloxybenzoic acid

IR (Nujol): 2600, 1680, 1600, 1270, 1230 $cm^{-1}$

NMR (DMSO-$d_6$, δ) 0.86 (3H, t, J=6.8 Hz), 1.2–1.5 (10H, m), 1.6–1.8 (2H, m), 3.80 (3H, s), 4.01 (2H, t, J=6.5 Hz), 7.03 (1H, d, J=8.5 Hz), 7.44 (1H, d, J=1.9 Hz), 7.54 (1H, dd, J=8.5 and 1.9 Hz)

Preparation 55

4-(4-Octyloxyphenyl)benzoic acid

IR (Nujol): 1670, 1600, 830, 770 $cm^{-1}$

NMR (DMSO-$d_6$, δ): 0.87 (3H, t, J=6.7 Hz), 1.2–1.5 (10H, m), 1.6–1.8 (2H, m), 4.01 (2H, t, J=6.4 Hz), 7.04 (2H, d, J=8.8 Hz), 7.68 (2H, d, J=8.8 Hz), 7.75 (2H, d, J=8.5 Hz), 7.99 (2H, d, J=8.5 Hz)

Preparation 56

6-(2 -Ethylhexyloxy)-2-naphthoic acid

IR (Nujol): 1660, 1610, 1280, 1200 $cm^{-1}$

NMR (DMSO-$d_6$, δ): 0.88 (3H, t, J=7.3 Hz), 0.92 (3H, t, J=7.3 Hz), 1.2–1.6 (8H, m), 1.7–1.9 (1H, m), 4.01 (2H, d, J=5.7 Hz), 7.23 (1H, dd, J=8.9 and 2.4 Hz), 7.42 (1H, d, J=2.4 Hz), 7.86 (1H, d, J=8.7 Hz), 7.94 (1H, d, J=8.7 Hz), 8.01 (1H, d, J=8.9 Hz), 8.51 (1H, s), 12.9 (1H, s)

Preparation 57

6-(3,7-Dimethyl-6-octenyloxy)naphthoic acid

IR (Nujol): 1660, 1610, 1290, 1200 $cm^{-1}$

NMR (DMSO-$d_6$, δ): 0.95 (3H, d, J=6.1 Hz), 1.1–1.5 (2H, m), 1.57 (3H, s), 1.64 (3H, s), 1.6–2.1 (5H, m), 4.15 (2H, t, J=6.7 Hz), 5.10 (1H, t, J=7.1 Hz), 7.22 (1H, dd, J=8.9 and 2.3 Hz), 7.42 (1H, d, J=2.3 Hz), 7.86 (1H, d, J=8.6 Hz), 7.94 (1H, d, J=8.6 Hz), 8.01 (1H, d, J=8.9 Hz), 8.52 (1H, s), 12.89 (1H, s)

Preparation 58

6-(3,7-Dimethyl-2,6-octadienyloxy)naphthoic acid

IR (Nujol): 1660, 1620, 1210 $cm^{-1}$

NMR (DMSO-$d_6$, δ): 1.57 (3H, s), 1.60 (3H, s), 1.76 (3H, s), 2.07 (4H, m), 4.70 (2H, d, J=6.5 Hz), 5.07 (1H, m), 5.51 (1H, t, J=6.5 Hz), 7.24 (1H, dd, J=8.9 and 2.4 Hz), 7.41 (1H, d, J=2.4 Hz), 7.85 (1H, d, J=8.7 Hz), 7.94 (1H, d, J=8.7 Hz), 8.01 (1H, d, J=8.9 Hz), 8.52 (1H, s), 12.88 (1H, s)

Preparation 59

(2E)-3-(4-Octyloxyphenyl)acrylic acid

IR (Nujol): 1660, 1600, 1240 $cm^{-1}$

NMR (DMSO-$d_6$, δ): 0.86 (3H, t, J=6.7 Hz), 1.2–1.5 (10H, m), 1.6–1.8 (2H, m), 4.00 (2H, t, J=6.4 Hz), 6.36 (1H, d, J=16 Hz), 6.95 (2H, d, J=8.7 Hz), 7.54 (1H, d, J=16 Hz), 7.61 (2H, d, J=8.7 Hz), 12.20 (1H, br s)

Preparation 60

Sodium 6-octyloxy-2-naphthalene sulfonate

IR (Nujol): 1230, 1180, 860, 820 $cm^{-1}$

NMR (DMSO-$d_6$, δ): 0.86 (3H, t, J=6 Hz), 1.1–1.6 (10H, m), 4.06 (2H, t, J=5 Hz), 7.08 (1H, d, J=9 Hz), 7.21 (1H, s), 7.79 (1H, d, J=9 Hz), 8.00 (1H, s)

Preparation 61

To a solution of thionyl chloride (0.692 ml) and N,N-dimethylformamide (0.022 ml) was added sodium 6-octyloxy-2-naphthalenesulfonate (1 g) under ice-cooling. The mixture was stirred for 1.5 hours at 95° C., then evaporated under reduced pressure to give 6-octyloxy-2-naphthylsulfonyl chloride (1 g) .

IR (Nujol): 1610, 1260, 1160 $cm^{-1}$

NMR ($CDCl_3$, δ): 0.90 (3H, t, J=6.2 Hz), 1.2–1.7 (10H, m), 1.8–2.0 (2H, m), 4.12 (2H, t, J=6.5 Hz), 7.20 (1H, d, J=2.2 Hz), 7.32 (1H, dd, J=9.0 and 2.2 Hz), 7.84–7.97 (3H, m), 8.49 (1H, s)

The following compounds (Preparations 62 to 71) were obtained according to procedures similar to that of Preparation 12.

Preparation 62

1-(4-Octylbenzoyl)-1H-benzotriazole-3-oxide

IR (Neat): 2930, 2850, 1780, 1610, 1240, 990 $cm^{-1}$

Preparation 63

1-[4-(4-Octyloxyphenyl)benzoyl]-1H-benzotriazole-3-oxide

IR (Nujol): 1770, 1600, 980 $cm^{-1}$

Preparation 64

1-[6-(2-Ethylhexyloxy)-2-naphthoyl]-1H-benzotriazole-3-oxide

IR (Nujol): 1770, 1620, 1270, 1180 $cm^{-1}$

NMR ($CDCl_3$, δ): 0.93 (3H, t, J=7.1 Hz), 0.98 (3H, t, J=7.4 Hz), 1.3–1.7 (8H, m), 1.7–2.0 (1H, m), 4.03 (2H, d, J=5.7 Hz), 7.22 (1H, d, J=2.2 Hz), 7.29 (1H, dd, J=8.9 and 2.2 Hz), 7.4–7.7 (3H, m), 7.87 (1H, d, J=9.5 Hz), 7.92 (1H, d, J=9.5 Hz) , 8.1–8.2 (2H, m), 8.80 (1H, s)

Preparation 65

1-[6-(3,7-Dimethyl-6-octenyloxy)-2-naphthoyl]-1H-benzotriazole-3-oxide

IR (Neat): 2900, 1770, 1620, 1180 $cm^{-1}$

Preparation 66

1-[6-{(E)-3,7-Dimethyl-2,6-octadienyloxy}-2-naphthoyl]-1H-benzotriazole-3-oxide

IR (Nujol): 1770, 1620, 1270, 1180 $cm^{-1}$

Preparation 67

1-(2-Anthrylcarbonyl)-1H-benzotriazole-3-oxide

IR (Nujol): 1780, 1200, 720, 740 $cm^{-1}$

Preparation 68

1-[2-(4-Octyloxyphenyl)acetyl]-1H-benzotriazole-3-oxide

IR (Nujol): 1730, 1460, 1420, 1250, 1130 $cm^{-1}$

Preparation 69

1-[3-(4-Octyloxyphenyl)propionyl]-1H-benzotriazole-3-oxide

IR (Nujol): 1730, 1420, 1340, 1240, 950 $cm^{-1}$

Preparation 70

1-[(E)-3-(4-Octyloxyphenyl)acryloyl]-1H-benzotriazole-3-oxide

IR (Nujol): 1770, 1600, 1260, 1080 $cm^{-1}$

Preparation 71

1-($O^4$-Octyl-N,N-dimethyl-L-tyrosyl)-1H-benzotriazole-3-oxide

IR (Neat): 2930, 2850, 1800, 1610 $cm^{-1}$

Preparation 72

To a suspension of lithium aluminum hydride (4.05 g) in tetrahydrofuran (475 ml) was added dropwise a solution of 4-octyloxybenzaldehyde (25 g) in tetrahydrofuran (25 ml) at 55°–60° C. The reaction mixture was stirred under reflux for 1 hour. Thereto, sodium fluoride (35.84 g) and water (11.52 ml) were added under ice-cooling. The mixture was stirred for 30 minutes, and filtered. The filtrate was evaporated in vacuo to give 4-octyloxybenzyl alcohol (25.1 g) as crystals.

IR (Nujol): 3200, 1605, 1510 $cm^{-1}$

NMR (DMSO-$d_6$, δ): 0.86 (3H, t, J=6.7 Hz), 1.26–1.38 (10H, m), 1.62–1.72 (2H, m), 3.92 (2H, t, J=6.5 Hz), 4.40 (2H, d, J=5.7 Hz), 5.03 (1H, t, J=5.7 Hz), 6.85 (2H, d, J=8.6 Hz), 7.20 (2H, d, J=8.6 Hz)

Preparation 73

Diethyl azodicarboxylate (18.4 g) was added dropwise to a suspension of 4-octyloxybenzyl alcohol (25 g), N-hydroxyphthalimide (17.15 g) and triphenylphosphine (27.74 g) in tetrahydrofuran (250 ml) under ice-cooling. The reaction mixture was stirred at room temperature for 2 hours, and evaporated in vacuo. The residue was purified by chromatography on silica gel to give N-(4-octyloxybenzyloxy)phthalimide (33.45 g) as crystals.

IR (Nujol): 1780, 1725, 1605, 1580, 1505 $cm^{-1}$

NMR (DMSO-$d_6$, δ): 0.86 (3H, m), 1.26 (10H, m), 1.70 (2H, m), 3.95 (2H, t, J=6.5 Hz), 5.08 (2H, s), 6.93 (2H, d, J=8.6 Hz), 7.40 (2H, d, J=8.6 Hz), 7.85 (4H, s)

Preparation 74

To a solution of N-(4-octyloxybenzoyloxy)phthalimide (4.13 g) in tetrahydrofuran (16 ml) was added hydrazine hydrate (0.53 ml) at room temperature. After the mixture was stirred at the same temperature for 1 hour, the precipitate was filtered off. To the filtrate were added water (6 ml) and 4-hydroxyphenylglyoxylic acid (1.5 g) at room temperature. The mixture was maintained at pH 4–4.5 with aqueous sodium bicarbonate solution for 2 hours. Thereto was added ethyl acetate, and adjusted to pH 2 with 1N hydrochloric acid. The separated organic layer was washed with brine, and dried over magnesium sulfate. The magnesium sulfate was filtered off, and the organic solvent was evaporated in vacuo to give 2-(4 -hydroxyphenyl)-2-(4 -octyloxybenzyloxyimino) acetic acid (3.4 g).

IR (Nujol): 3400, 1715, 1605, 1590, 1505 $cm^{-1}$

NMR (DMSO-$d_6$, δ): 0.86 (3H, m), 1.25 (10H, m), .1.69 (2H, m), 3.94 (2H, t, J=6.4 Hz), 5.07 (2H, s), 6.82 (2H, d, J=8.7 Hz), 6.90 (2H, d, J=8.6 Hz), 7.29 (2H, d, J=8.6 Hz), 7.35 (2H, d, J=8.7 Hz)

The following compounds (Preparations 75 and 76) were obtained according to procedures similar to that of Preparation 74.

Preparation 75

2-Phenyl-2-(4-octyloxybenzyloxyimino)acetic acid

IR (Nujol): 1720, 1610, 1585, 1515 $cm^{-1}$

NMR (DMSO-$d_6$, δ): 0.86 (3H, t, J=6.7 Hz), 1.26 (10H, m), 1.69 (2H, m), 3.94 (2H, t, J=6.5 Hz), 5.13 (2H, s), 6.91 (2H, d, J=8.6 Hz), 7.22–7.49 (7H, m)

Preparation 76

2- (4-Octyloxybenzyloxyimino)acetic acid

IR (Nujol): 1700, 1670, 1600 $cm^{-1}$

NMR (DMSO-$d_6$, δ): 0.86 (3H, t, J=6.2 Hz), 1.26 (10H, m), 1.70 (2H, m), 3.95 (2H, t, J=6.5 Hz), 5.13 (2H, s), 6.91 (2H, d, J=8.6 Hz), 7.29 (2H, d, J=8.6 Hz), 7.56 (1H, s)

Preparation 77

A solution of 4-octyloxyphenylglyoxylic acid (0.935 g) in a mixture of water (9 ml) and tetrahydrofuran (18 ml) was adjusted to pH 3.5–4 with 1N hydrochloric acid, and methoxyamine hydrochloride (0.337 g) was added thereto at room temperature. The mixture was stirred for 2 hours at room temperature maintaining pH 3.5–4 with 1N hydrochloric acid. The reaction mixture was added to ethyl acetate. The organic layer was separated and dried over magnesium sulfate. The magnesium sulfate was filtered off, and the filtrate was evaporated under reduced pressure to give 2-(4-octyloxyphenyl)-2-methoxyiminoacetic acid (0.57 g).

IR (Nujol): 1700, 1600, 1250, 1030 $cm^{-1}$

NMR (DMSO-$d_6$, δ): 0.86 (3H, t, J=6.3 Hz), 1.2–1.5 (10H, m), 1.6–1.8 (2H, m), 3.89 (3H, s), 3.99 (2H, t, J=6.4 Hz), 7.00 (2H, d, J=8.9 Hz), 7.45 (2H, d, J=8.9 Hz), 14.05 (1H, s)

Preparation 78

To a mixture of 2,3,4,5,6-pentafluorobenzoic acid (1 g) and 2,2,3,3,4,4,5,5-octafluoropentanol (1.18 g) in N,N-dimethylformamide (5 ml) was added 62% sodium hydride (0.39 g) at room temperature. The mixture was stirred at the same temperature for 1 hour, and thereto was added a mixture of water and ethyl acetate. The separated organic layer was washed with water and brine, dried over magnesium sulfate, filtered, and evaporated in vacuo. The residue was purified by chromatography on silica gel to give 4-(2,2,3,3,4,4,5,5-octafluoropentyloxy)-2,3,5,6-tetrafluorobenzoic acid (923.0 mg).

IR (Nujol): 1700, 1580 $cm^{-1}$

NMR (DMSO-$d_6$, δ): 4.96 (2H, t, J=14.2 Hz), 7.10 (1H, tt,

J=5.6 and 50.2 Hz)

Preparation 79

4-(2,2,3,3,4,4,5,5,6,6,7,7,8,8,8-Pentadecafluorooctyloxy)-2,3,5,6-tetrafluorobenzoic acid was prepared by a procedure similar to that of Preparation 78.

IR (Nujol): 3400, 1640, 1560 $cm^{-1}$

NMR (DMSO-$d_6$, δ): 4.95 (2H, t, J=14.0 Hz)

The following compounds (Preparations 80 to 90) were obtained according to procedures similar to that of Preparation 5.

Preparation 80

Succinimido 2-(4-hydroxyphenyl)-2-(4-octyloxybenzyloxyimino)acetate

IR (Nujol): 1800, 1770, 1700, 1600 $cm^{-1}$

Preparation 81

Succinimido 2-phenyl-2-(4 -octyloxybenzyloxyimino)-acetate

IR (Nujol): 1780, 1730, 1605 $cm^{-1}$

NMR (DMSO-$d_6$, δ): 0.86 (3H, m), 1.26 (10H, m), 1.69 (2H, m), 2.90 (4H, m), 3.94 (2H, t, J=6.4 Hz), 5.30 (2H, s), 6.91 (2H, d, J=8.6 Hz), 7.25–7.56 (7H, m)

Preparation 82

Succinimido 2-(4-Octyloxybenzyloxyimino)acetate

IR (Nujol): 1760, 1725, 1600, 1580 $cm^{-1}$

NMR (DMSO-$d_6$, δ): 0.86 (3H, t, J=6.7 Hz), 1.26 (10H, m), 1.70 (2H, m), 2.85 (4H, s), 3.96 (2H, m), 5.28 (2H, s), 6.91 (2H, d, J=8.6 Hz), 7.33 (2H, d, J=8.6 Hz), 8.12 (1H, s)

Preparation 83

Succinimido 4-(2,2,3,3,4,4,5,5-octafluoropentyloxy)-2,3,5,6-tetraflurobenzoate

IR (Nujol): 3500, 1770, 1740, 1640 $cm^{-1}$

NMR (DMSO-$d_6$, δ): 2.90 (4H, s), 5.23 (2H, t, J=13.8 Hz), 7.11 (1H, tt, J=50.2 and 5.6 Hz)

Preparation 84

Succinimido 4-(2,2,3,3,4p4,5,5,6,6,7,7,8,8,8-pentadecafluorooctyloxy)-2,3,5,6-tetrafluorobenzoate IR (Nujol): 1735, 1620, 1600 $cm^{-1}$ NMR (DMSO-$d_6$, δ): 2.90 (4H, s), 5.12 (2H, t, J=13.8 Hz)

Preparation 85

Succinimido 3-methoxy-4-octyloxybenzoate

IR (Nujol): 1760, 1730, 1600, 1280, 1200, 880 $cm^{-1}$

NMR (DMSO-$d_6$, δ): 0.86 (3H, t, J=6.7 Hz), 1.2–1.5 (10H, m), 1.6–1.9 (2H, m), 2.88 (4H, s), 3.84 (3H, s), 4.09 (2H, t, J=6.5 Hz), 7.19 (1H, d, J=8.6 Hz), 7.49 (1H, d, J=2.0 Hz), 7.73 (1H, dd, J=8.6 and 2.0 Hz)

Preparation 86

Succinimido 4-(2-butoxyethoxy)benzoate

IR (Nujol): 1730, 1600, 1250, 1060 $cm^{-1}$

NMR (DMSO-$d_6$, δ): 0.87 (3H, t, J=7.2 Hz), 1.2–1.6 (4H, m), 2.89 (4H, s), 3.46 (2H, t, J=6.3 Hz), 3.73 (2H, t, J=4.4 Hz), 4.25 (2H, t, J=4.4 Hz), 7.18 (2H, d, J=9.0 Hz), 8.04 (2H, d, J=9.0 Hz)

Preparation 87

Succinimido 2-(4-octyloxyphenyl) -2-methoxyacetate

IR (Nujol): 1810, 1740, 1610, 1250, 1210, 1100 $cm^{-1}$

NMR (DMSO-$d_6$, δ): 0.86 (3H, t, J=6.7 Hz), 1.2–1.5 (10H, m), 1.6–1.8 (2H, m), 2.80 (4H, s), 3.35 (3H, s), 3.97 (2H, t, J=6.4 Hz), 5.35 (1H, s), 6.96 (2H, d, J=8.7 Hz), 7.38 (2H, d, J=8.7 Hz)

Preparation 88

$O^4$-Octyl-N-(t-butoxycarbonyl)-D-tyrosine succinimido ester

IR (Nujol): 3370, 1780, 1730, 1700, 1250, 1200 $cm^{-1}$

Preparation 89

Succinimido 2-(4-octyloxyphenyl)-2-methoxyiminoacetate

IR (Nujol): 1800, 1780, 1730, 1600, 1250, 1180, 1130 $cm^{-1}$

NMR (DMSO-$d_6$, δ): 0.86 (3H, t, J=6.6 Hz), 1.2–1.5 (10H, m), 1.6–1.8 (2H, m), 2.89 (4H, s), 4.01 (3H, s), 4.03 (2H, t, J=6.4 Hz), 7.08 (2H, d, J=8.9 Hz), 7.68 (2H, d, J=8.9 Hz)

Preparation 90

$N^{\tau}$-Octyl-N-(t-butoxycarbonyl)-L-histidine succinimido ester

IR (Neat): 1810, 1780, 1730, 1500, 1360, 1200, 1160 $cm^{-1}$

Preparation 91

4-Octyloxyphthalic anhydride was obtained from 4-octyloxyphthalic acid according to a procedure similar to that of Preparation 5.

IR (Neat): 2910, 2850, 1840, 1760, 1640, 1610, 1290, 1260 $cm^{-1}$

NMR (DMSO-$d_6$, δ): 0.86 (3H, t, J=6.8 Hz), 1.2–1.5 (10H, m), 1.6–1.9 (2H, m), 4.19 (2H, t, J=6.5 Hz), 7.47 (1H, dd, J=8.4 and 2.2 Hz), 7.57 (1H, d, J=2.2 Hz), 7.98 (1H, d, J=8.4 Hz)

Preparation 92

N-Octyloxycarbonyloxysuccinimide was obtained according to a procedure similar to that of Preparation 5.

IR (Neat): 2960, 2850, 1780, 1740, 1260, 1230 $cm^{-1}$

NMR ($CDCl_3$, δ): 0.89 (3H, t, J=6.7 Hz), 1.2–1.4 (10H, m), 1.6–1.8 (2H, m), 2.84 (4H, s), 4.32 (2H, t, J=6.7 Hz)

Preparation 93

To a solution of octyl phenyl ether (1.53 g) in chloroform (6 ml) was added chlorosulfonic acid at 0° C. The mixture was stirred at room temperature for 30 minutes, then the mixture was poured into a mixture of water and tetrahydrofuran.

The separated organic layer was washed with aqueous sodium chloride, dried over magnesium sulfate and then the solvent was evaporated in vacuo. The residue was subjected to a column chromatography on silica gel to give 4-octyloxyphenylsulfonyl chloride (1.25 g).

IR (Nujol): 1600, 1580, 1500, 1380, 1180 $cm^{-1}$

NMR ($CDCl_3$, δ): 0.89 (3H, t, J=6.6 Hz), 1.20–1.50 (10H, m), 1.80 (2H, m), 4.06 (2H, t, J=6.4 Hz), 7.03 (2H, d, J=9.0 Hz), 7.96 (2H, d, J=9.0 Hz)

In the following Table, the structures of the R groups of the compounds of Examples 13 to 53 are shown, wherein the compounds have the following general formula:

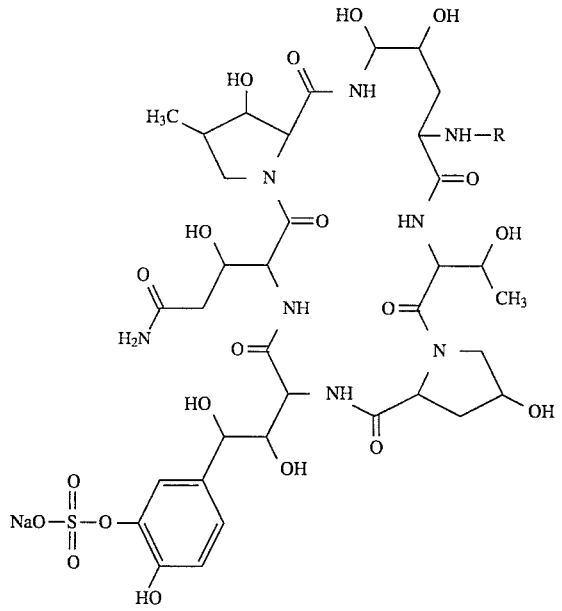

In the following formulae, $^t$Bu means t-butyl, and p-TsOH means p-toluenesulfonic acid.

| Example No. | Compound No. | R |
|---|---|---|
| 13 | FR139835 | $-COO(CH_2)_7CH_3$ |
| 14 | FR139537 | 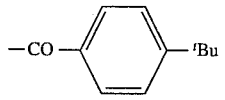 |
| 15 | FR141145 | 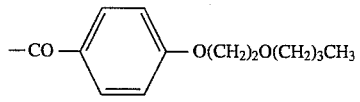 |
| 16 | FR139538 | 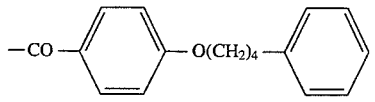 |
| 17 | FR140215 | 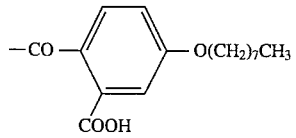 |

-continued
| Example No. | Compound No. | R |
|---|---|---|
| 18 | FR140216 | 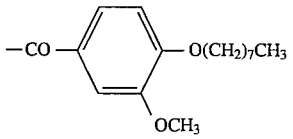 |
| 19 | FR140727 | 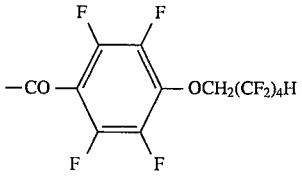 |
| 20 | FR143301 | 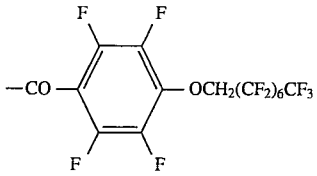 |
| 21 | FR140495 | 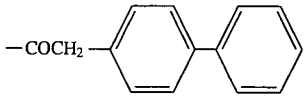 |
| 22 | FR139503 | 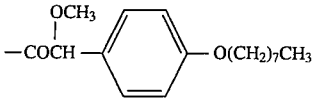 |
| 23 | FR139500 | 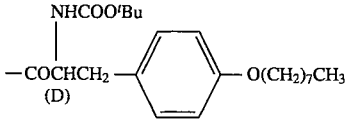 |
| 24 | FR139501 | 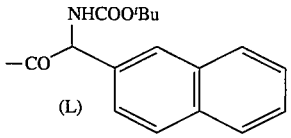 |
| 25 | FR139502 | 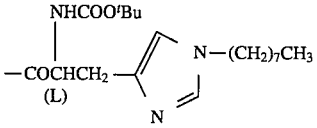 |
| 26 | FR138959 | 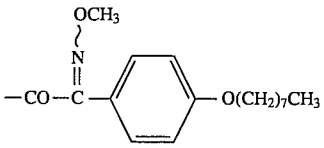 |
| 27 | FR140291 | 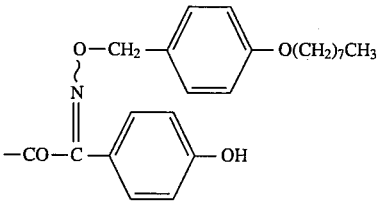 |
-continued
| Example No. | Compound No. | R |
|---|---|---|
| 28 | FR141580 | 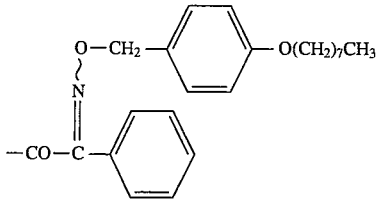 |
| 29 | FR141579 | 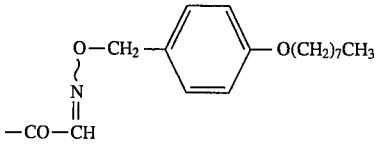 |
| 30 | FR141146 | 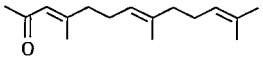 |
| 31 | FR140731 | 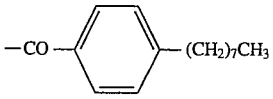 |
| 32 | FR140217 | 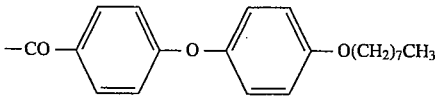 |
| 33 | FR142472 | 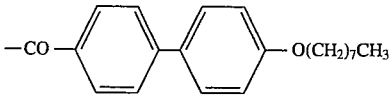 |
| 34 | FR140496 | 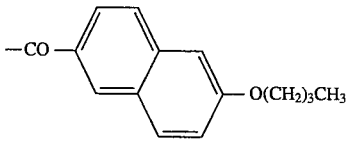 |
| 35 | FR140497 | 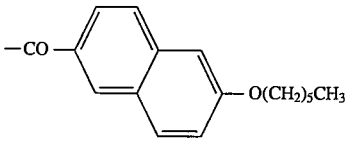 |
| 36 | FR143483 | 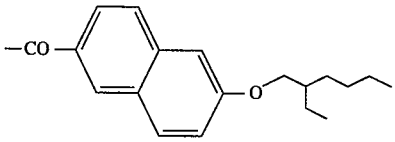 |
| 37 | FR140728 | 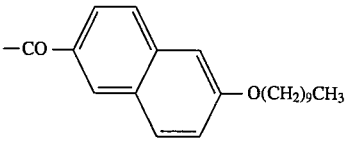 |
| 38 | FR142172 | 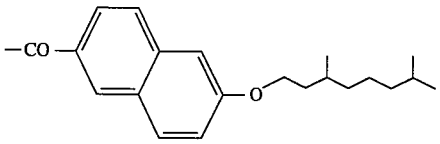 |

-continued

| Example No. | Compound No. | R |
|---|---|---|
| 39 | FR143326 | 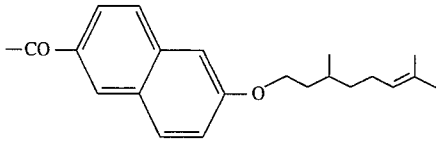 |
| 40 | FR142390 | 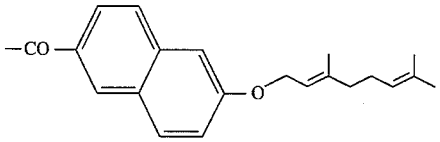 |
| 41 | FR140729 | 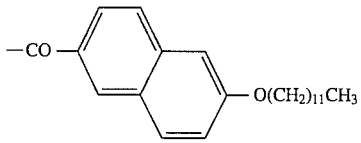 |
| 42 | FR140730 | 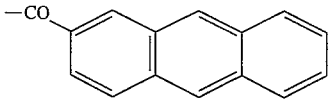 |
| 43 | FR143020 | 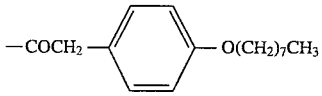 |
| 44 | FR143021 | 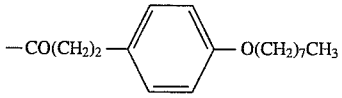 |
| 45 | FR141315 | 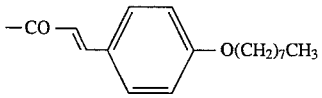 |
| 46 | FR140105 | 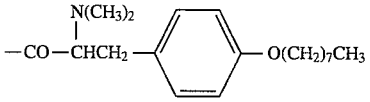 |
| 47 | FR141564 | 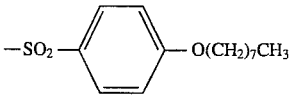 |
| 48 | FR143170 | 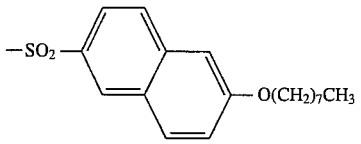 |
| 49 | FR138912 | 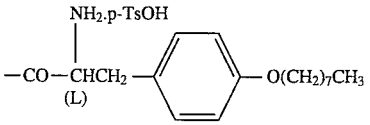 |
| 50 | FR138960 | 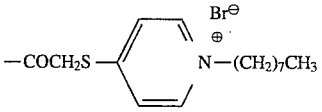 |

-continued

| Example No. | Compound No. | R |
|---|---|---|
| 51 | FR138727 | 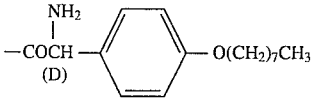 |
| 52 | FR138912 | 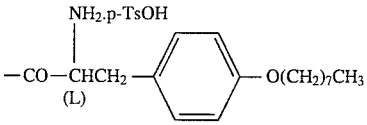 |
| 53 | FR138960 | 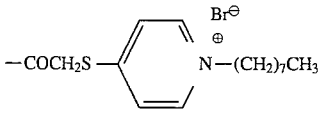 |

EXAMPLE 13

FR139835 substance was obtained by reacting FR133303 substance with N-octyloxycarbonyloxysuccinimide according to a method similar to that of Example 3.

IR (Nujol): 3300, 1620 $cm^{-1}$

FAB-MS e/z=1137 (M+Na)

EXAMPLE 14

FR139537 substance was obtained by reacting FR133303 substance with succinimido 4-t-butylbenzoate according to a method similar to that of ExamDle 3.

IR (Nujol): 3300, 1620 $cm^{-1}$

NMR ($D_2O$, δ): 1.05 (3H, d, J=6.9 Hz), 1.15 (3H, d, J=5.9 Hz) , 1.33 (9H, s), 2.0–2.3 (3H, m), 2.4–2.6 (3H, m), 2.7–2.9 (1H, m), 3.4–3.6 (1H, m), 3.8–4.9 (12H, m), 5.07 (2H, m), 5.40 (1H, d, J=3 Hz), 7.06 (1H, d, J=8.2 Hz), 7.08 (1H, dd, J=8.2 and 2 Hz), 7.27 (1H, d, J=2 Hz), 7.60 (1H, d, J=8.6 Hz), 7.75 (1H, d, J=8.6 Hz )

EXAMPLE 15

FR141145 substance was obtained by reacting FR133303 substance with succinimido 4-(2-butoxyethoxy)benzoate according to a method similar to that of Example 3.

IR (Nujol): 3300, 1620 $cm^{-1}$

NMR (DMSO-$d_6$+$D_2O$, δ): 0.88 (3H, t, J=7.3 Hz), 0.96 (3H, d, J=6.7 Hz), 1.04 (3H, d, J=5.7 Hz), 1.2–1.6 (4H, m), 1.7–2.0 (3H, m), 2.1–2.65 (4H, m), 3.16 (1H, m), 3.7–4.5 (20H, m), 4.78 (1H, d, J=3 Hz), 4.86 (1H, d, J=3.8 Hz), 5.02 (1H, d, J=3 Hz), 6.74 (1H, d, J=8.2 Hz), 6.79 (1H, d, J=8.2 Hz), 7.00 (2H, d, J=8.9 Hz), 7.06 (1H, s), 7.87 (2H, d, J=8.9 Hz) FAB-MS e/z=1201 (M+Na)

EXAMPLE 16

FR139538 substance was obtained by reacting FR133303 substance with succinimido 4-(4-phenylbutoxy)benzoate according to a method similar to that of Example 3.

IR (Nujol): 3300, 1620 $cm^{-1}$

FAB-MS e/z=1233 (M+Na)

EXAMPLE 17

FR140215 substance was obtained by reacting FR133303 substance with 4-octyloxyphthalic anhydride according to a method similar to that of Example 3.

IR (Nujol): 3300, 1620 $cm^{-1}$

FAB-MS e/z=1257 (M+Na)

EXAMPLE 18

FR140216 substance was obtained by reacting FR133303 substance with succinimido 3-methoxy-4-octyloxybenzoate according to a method similar to that of Example 3.

IR (Nujol): 3300, 1620 $cm^{-1}$

FAB-MS e/z=1243 (M+Na)

EXAMPLE 19

FR140727 substance was obtained by reacting FR133303 substance with succinimido 4-(2,2,3,3,4,4,5,5-octafluoropentyloxy)-2,3,5,6-tetrafluorobenzoate according to a method similar to that of EXample 3.

IR (Nujol): 3300, 1630 $cm^{-1}$

FAB-MS e/z=1387 (M+Na)

EXAMPLE 20

FR143301 substance was obtained by reacting FR133303 substance with succinimido 4-(2,2,3,3,4,4,5,5,6,6,7,7,8,8,8-pentadecafluorooctyloxy)-2,3,5,6-tetrafluorobenzoate according to a method similar to that of Example 3.

IR (Nujol): 3300, 1630 $cm^{-1}$

FAB-MS e/z=1534 ($M^+$)

EXAMPLE 21

FR140495 substance was obtained by reacting FR133303 substance with succinimido 2-(4-biphenylyl)acetate according to a method similar to that of Example 3.

IR (Nujol): 3300, 1620 $cm^{-1}$

NMR ($CD_3OD$, δ): 1.0–1.1 (6H, m), 1.9–2.2 (3H, m), 2.3–2.6 (3H, m), 2.7–2.85 (1H, m), 3.35 (1H, M), 3.58 (2H, s), 3.65–4.7 (13H, m), 4.93 (1H, d, J=3 Hz), 5.04 (1H, d, J=3.8 Hz), 5.25 (1H, d, J=3 Hz), 6.85 (1H, d, J=8.3 Hz), 7.01 (1H, dd, J=8.3 and 2 Hz ) , 7.3–7.6 (10H, m)

EXAMPLE 22

FR139503 substance was obtained by reacting FR133303 substance with succinimido 2-(4-octyloxyphenyl)-2-methoxyacetate according to a method similar to that of Example 3.

IR (Nujol): 3330, 1620 $cm^{-1}$

FAB-MS e/z=1257 (M+Na)

EXAMPLE 23

FR139500 substance was obtained by reacting FR133303 substance with $O^4$-octyl-N-(t-butoxycarbonyl)-D-tyrosine succinimido ester according to a method similar to that of Example 3.

IR (Nujol): 3300, 1620 $cm^{-1}$

NMR ($CD_3OD$, δ): 0.90 (3H, t, J=6.8 Hz), 1.06 (3H, d, J=6.8 Hz), 1.17 (3H, d, J=6.7 Hz), 1.20–1.30 (10H, m), 1.35 (9H, s), 1.74 (2H, m), 1.9–2.1 (3H, m), 2.45 (3H, m), 2.76 (1H, m), 3.0–3.1 (1H, m), 3.37 (1H, m), 3.7–4.6 (18H, m), 4.94 (1H, d, J=3 Hz), 5.01 (1H, d, J=3.8 Hz), 5.25 (1H, d, J=3 Hz), 6.79 (2H, d, J=8.5 Hz), 6.83 (1H, d, J=8.3 Hz), 7.03 (1H, dd, J=8.3 and 2 Hz), 7.12 (2H, d, J=8.5 Hz), 7.31 (1H, d, J=2 Hz)

EXAMPLE 24

FR139501 substance was obtained by reacting FR133303 substance with N-(t-butoxycarbonyl)-L-2-(2-naphthyl)glycine succinimido ester according to a method similar to that of Example 3.

IR (Nujol): 3300, 1620 $cm^{-1}$

EXAMPLE 25

FR139502 substance was obtained by reacting FR133303 substance with $N^{\tau}$-octyl-N-(t-butoxycarbonyl)-L-histidine succinimido ester according to a method similar to that of Example 3.

IR (Nujol): 3300, 1620 $cm^{-1}$

FAB-MS e/z=1330 (M+Na)

EXAMPLE 26

FR138959 substance was obtained by reacting FR133303 substance with succinimido 2-(4-octyloxyphenyl)-2-methoxyiminoacetate according to a method similar to that of Example 3.

IR (Nujol): 3300, 1620 $cm^{-1}$

NMR ($CD_3OD$, δ): 0.91 (3H, t, J=6.6 Hz), 1.06 (3H, d, J=6.8 Hz), 1.25 (3H, d, J=6.3 Hz), 1.25–1.6 (10H, m), 1.65–1.9 (2H, m), 1.9–2.2 (3H, m), 2.3–2.65 (3H, m), 1.75–1.9 (1H, m), 3.3–3.5 (1H, m), 3.95 (3H, s), 3.7–4.75 (16H, m), 5.03 (1H, d, J=3.0 Hz), 5.11 (1H, d, J=3.7 Hz), 5.46 (1H, d, J=2.7 Hz), 6.86 (1H, d, J=8.2 Hz), 6.89 (2H, d, J=8.9 Hz), 7.01 (1H, dd, J=8.2 and 2 Hz), 7.31 (1H, d, J=2 Hz), 7.54 (2H, d, J=8.9 Hz)

FAB-MS e/z=1270 (M+Na)

EXAMPLE 27

FR140291 substance was obtained by reacting FR133303 substance with succinimido 2-(4-hydroxyphenyl)-2-(4-octyloxybenzyloxyimino)acetate according to a method similar to that of Example 3.

IR (Nujol): 3250, 1650, 1620 $cm^{-1}$

FAB-MS e/z=1363 (M+Na)

EXAMPLE 28

FR141580 substance was obtained by reacting FR133303 substance with succinimido 2-phenyl-2-(4-octyloxybenzyloxyimino)acetate according to a method similar to that of Example 3.

IR (Nujol): 3300, 1646 $cm^{-1}$

FAB-MS e/z=1346 (M+Na)

EXAMPLE 29

FR141579 substance was obtained by reacting FR133303 substance with succinimido 2-(4-octyloxybenzyloxyimino)acetate according to a method similar to that of Example 3.

IR (Nujol): 3250, 1650 $cm^{-1}$

FAB-MS e/z=1270 (M+Na)

EXAMPLE 30

FR141146 substance was obtained by reacting FR133303 substance with 1-[(2E,6E)-3,7,11-trimethyl-2,6,10-dodecatrienoyl]-1H-benzotriazole-3-oxide according to a method similar to that of Example 12.

IR (Nujol): 3300, 1620, 1040 $cm^{-1}$

NMR ($CD_3OD$, δ): 1.06 (3H, d, J.=6.8 Hz), 1.19 (3H, d, J=5.9 Hz), 1.60 (3H, s), 1.62 (3H, s), 1.66 (3H, s), 1.9–2.2 (11H, m), 2.05 (3H, s), 2.3–2.6 (3H, m), 2.7–2.9 ( 1H, m), 3.35 ( 1H, m), 3.7–5.0 ( 14H, m), 5.08 (4H, m), 5.27 (1H, d, J=2.8 Hz), 5.77 (1H, s), 6.86 (1H, d, J=8.3 Hz), 7.04 (1H, dd, J=8.3 and 1.9 Hz), 7.32 (1H, d, J=1.9 Hz)

EXAMPLE 31

FR140731 substance was obtained by reacting FR133303 substance with 1-(4-octylbenzoyl)-1H-benzotriazole-3-oxide according to a method similar to that of Example 12.

IR (Nujol): 3300, 1620, 1040 $cm^{-1}$

NMR ($CD_3OD$, δ): 0.86 (3H, t, J=6.8 Hz), 1.06 (3H, d, J=6.8 Hz), 1.21 (3H, d, J=5.8 Hz), 1.25–1.45 (10H, m), 1.55–1.75 (2H, m), 1.9–2.25 (3H, m), 2.35–2.6 (3H, m), 2.65 (2H, t, J=7.5 Hz), 2.81 (1H, m), 3.32 (1H, m), 3.7–4.8 (14H, m), 4.98 (1H, d, J=3 Hz), 5.09 (1H, d, J=3.9 Hz), 5.31 (1H, d, J=3 Hz), 6.86 (1H, d, J=8.3 Hz), 7.03 (1H, dd, J=8.3 and 2 Hz), 7.24 (2H, d, J=8.2 Hz), 7.33 (1H, d, J=2 Hz), 7.74 (2H, d, J=8.2 Hz)

FAB-MS e/z=1197 (M+Na)

EXAMPLE 32

FR140217 substance was obtained by reacting FR133303 substance with 1-[4-(4-octyloxy)phenoxy]benzoyl-1H-benzotriazole-3-oxide according to a method similar to that of Example 12.

IR (Nujol): 3300, 1620 $cm^{-1}$

FAB-MS e/z=1305 (M+Na)

EXAMPLE 33

FR142472 substance was obtained by reacting FR133303 substance with 1-[4-(4-octyloxyphenyl)benzoyl]-1H-benzotriazole-3-oxide according to a method similar to that of Example 12.

IR (Nujol): 3300, 1620 $cm^{-1}$

NMR ($CD_3OD$, δ): 0.88 (3H, t, J=6.7 Hz), 1.06 (3H, d, J=6.8 Hz), 1.23 (3H, d, J=6.1 Hz), 1.3–1.6 (10H, m), 1.8–1.9 (2H, m), 1.9–2.3 (3H, m), 2.3–2.7 (3H, m), 2.9–3.0 (1H, m), 3.39 (1H, m), 3.7–4.7 (16H, m), 4.99 (1H, d, J=3.0 Hz), 5.10 (1H, d, J=3.7 Hz), 5.35 (1H, d, J=2.7 Hz), 6.87 (1H, d, J=8.3 Hz), 6.99 (2H, d, J=8.8 Hz), 7.04 (1H, dd, J=8.3 and 1.9 Hz), 7.33 (1H, d, J=1.9 Hz), 7.58 (2H, d, J=8.8 Hz), 7.62 (2H, d, J=8.4 Hz), 7.87 (2H, d, J=8.4 Hz)

FAB-MS e/z=1289 (M+Na)

EXAMPLE 34

FR140496 substance was obtained by reacting FR133303 substance with 1-(6-butoxy-2-naphthoyl)-1H-benzotriazole-3-oxide according to a method similar to that of Example 12.

IR (Nujol): 3300, 1620 $cm^{-1}$

FAB-MS e/z=1207 (M+Na)

EXAMPLE 35

FR140497 substance was obtained by reacting FR133303 substance with 1-(6-hexyloxy-2-naphthoyl)-1H-benzotriazole-3-oxide according to a method similar to that of Example 12.

IR (Nujol): 3300, 1620 $cm^{-1}$

NMR (DMSO-$d_6$+$D_2O$, δ): 0.89 (3H, t, J=6.6 Hz), 0.97 (3H, d, J=6.9 Hz), 1.08 (3H, d, J=5.9 Hz), 1.2–1.6 (6H, m), 1.7–2.1 (5H, m), 2.1–2.5 (3H, m), 2.5–2.7 (1H, m), 3.19 (1H, m), 3.73 (2H, m), 3.8–4.5 (12H, m), 4.80 (1H, d, J=3 Hz), 4.88 (1H, d, J=3.8 Hz), 5.08 (1H, d, J=3 Hz), 6.74 (1H, d, J=8.2 Hz), 6.80 (1H, dd, J=8.2 and 2 Hz), 7.08 (1H, d, J=2 Hz), 7.26 (1H, dd, J=8.9 and 2.4 Hz), 7.39 (1H, d, J=2.4 Hz), 7.85 (1H, d, J=8.7 Hz), 7.89 (1H, d, J=8.7 Hz), 7.93 (1H, d, J=8.9 Hz), 8.44 (1H, s)

FAB-MS e/z=1236 (M+Na)

EXAMPLE 36

FR143483 substance was obtained by reacting FR133303 substance with 1-[6-(2-ethylhexyloxy)-2-naphthoyl]-1H-benzotriazole-3-oxide according to a method similar to that of Example 12.

IR (Nujol): 3250, 1620 $cm^{-1}$

NMR ($CD_3OD$, δ): 0.93 (3H, t, J=7.4 Hz), 0.98 (3H, t, J=7.4 Hz), 1.06 (3H, d, J=6.8 Hz), 1.24 (3H, d, J=6.0 Hz), 1.3–1.7 (8H, m), 1.7–1.9 (1H, m), 1.9–2.3 (3H, m), 2.3–2.7 (3H, m), 2.8–3.0 (1H, m), 3.39 (1H, m), 3.7–4.7 (16H, m), 5.00 (1H, d, J=4.4 Hz), 5.11 (1H, d, J=3.7 Hz), 5.37 (1H, d, J=2.6 Hz), 6.87 (1H, d, J=8.3 Hz), 7.04 (1H, dd, J=8.3 and 2 Hz ), 7.17 (1H, dd, J=8.9 and 1.9 Hz), 7.22 (1H, d, J=2 Hz), 7.33 (1H, d, J=1.9 Hz), 7.7–7.9 (3H, m), 8.29 (1H, s)

FAB-MS e/z=1263 (M+Na)

EXAMPLE 37

FR140728 substance was obtained by reacting FR133303 substance with 1-(6-decyloxy-2-naphthoyl) -1H-benzotriazole-3-oxide according to a method similar to that of Example 12.

IR (Nujol): 3300, 1620 $cm^{-1}$

NMR (DMSO-$d_6$+$D_2O$, δ): 0.86 (3H, t, J=6.6 Hz), 0.97 (3H, d, J=6.7 Hz), 1.07 (3H, d, J=5.9 Hz), 1.2–1.6 (14H, m), 1.7–2.1 (5H, m), 2.1–2.5 (3H, m), 2.5–2.7 (1H, m), 3.19 (1H, m), 3.45 (1H, m), 3.73 (2H, m), 3.9–4.5 (12H, m), 4.79 (1H, d, J=3 Hz), 4.87 (1H, d, J=3.8 Hz), 5.07 (1H, d, J=3 Hz), 6.74 (1H, d, J=8.2 Hz), 6.79 (1H, dd, J=8.1 and 2 Hz), 7.06 (1H, d, J=2 Hz ), 7.23 ( 1H, dd, J=8.9 and 2.4 Hz), 7.38 (1H, d, J=2.4 Hz), 7.85 (1H, d, J=8.7 Hz), 7.89 (1H, d, J=8.7 Hz), 7.93 (1H, d, J=8.9 Hz), 8.45 (1H, s)

FAB-MS e/z=1291 (M+Na)

EXAMPLE 38

FR142172 substance was obtained by reacting FR133303 substance with 1-[6-(3,7-dimethyloctyloxy)-2-naphthoyl]-1H-benzotriazole-3-oxide according to a method similar to that of Example 12.

IR (Nujol): 3300, 1610 $cm^{-1}$

NMR (DMSO-$d_6$+$D_2O$, δ): 0.85 (6H, d, J=6.6 Hz), 0.95 (3H, d, J=5.9 Hz), 0.97 (3H, d, J=6.7 Hz), 1.08 (3H, d, J=5.9 Hz), 1.1–1.4 (6H, m), 1.4–2.1 (7H, m), 2.1–2.5 (3H, m), 2.5–2.7 (1H, m), 3.19 (1H, m), 3.74 (2H, m), 3.9–4.6 (12H, m), 4.81 (1H, d, J=3 Hz), 4.87 (1H, d, J=3.8 Hz), 5.07 (1H, d, J=3 Hz), 6.74 (1H, d, J=8.2 Hz), 6.83 (1H, dd, J=8.1 and 2 Hz), 7.06 (1H, d, J=2 Hz), 7.23 (1H, dd, J=8.9 and 2.4 Hz), 7.40 (1H, d, J=2.4 Hz), 7.85 (1H, d, J=8.7 Hz), 7.89 (1H, d, J=8.7 Hz), 7.93 (1H, d, J=8.9 Hz), 8.45 (1H, s)

FAB-MS e/z=1291 (M+Na)

EXAMPLE 39

FR143326 substance was obtained by reacting FR133303 substance with 1-[6-(3,7-dimethyl-6-octenyloxy) -2-naphthoyl]-1H-benzotriazole-3-oxide according to a method similar to that of Example 12.

IR (Nujol): 3300, 1620, 1260, 1040 $cm^{-1}$

NMR ($CD_3OD$, δ): 1.00 (3H, d, J=6.2 Hz), 1.06 (3H, d, J=6.8 Hz), 1.25 (3H, d, J=5.9 Hz), 1.2–1.6 (2H, m), 1.61 (3H, s), 1.67 (3H, s), 1.63–2.3 (8H, m), 2.3–2.7 (3H, m), 2.8–3.0 (1H, m), 3.39 (1H, m), 3.7–4.8 (16H, m), 5.00 (1H, d, J=5.1 Hz), 5.08–5.2 (2H, m), 5.37 (1H, d, J=2.5 Hz), 6.87 (1H, d, J=8.3 Hz), 7.04 (1H, d, J=8.3 Hz), 7.15 (1H, d, J=8.9 Hz), 7.21 (1H, s), 7.33 (1H, s), 7.71 (1H, d, J=8.7 Hz), 7.77–7.85 (2H, m), 8.28 (1H, s)

EXAMPLE 40

FR142390 substance was obtained by reacting FR133303 substance with 1-[6-{(E)-3,7-dimethyl-2,6-octadienyloxy}-2-naphthoyl]-1H-benzotriazole-3-oxide according to a method similar to that of Example 12.

IR (Nujol): 3300, 1620 $cm^{-1}$

NMR (DMSO-$d_6$+$D_2O$, δ): 0.97 (3H, d, J=6.7 Hz), 1.07 (3H, d, J=6.0 Hz), 1.57 (3H, s), 1.61 (3H, s), 1.76 (3H, s), 1.8–2.5 (9H, m), 2.5–2.7 (1H, m), 3.19 (1H, m), 3.45 (1H, m), 3.73 (2H, m), 3.9–4.6 (11H, m), 4.70 (2H, d, J=6.5 Hz), 4.80 (1H, d, J=3 Hz), 4.87 (1H, d, J=3.8 Hz), 5.07 (2H, m), 5.51 (1H, t, J=6.5 Hz), 6.74 ( 1H, d, J=8.3 Hz ), 6.83 ( 1H, dd, J=8.3 and 2 Hz), 7.07 (1H, d, J=2 Hz ), 7.24 ( 1H, dd, J=8.9 and 2.4 Hz) , 7.40 (1H, d, J=2.4 Hz), 7.8–8.0 (3H, m), 8.45 (1H, s)

FAB-MS e/z=1287 ( M+Na )

EXAMPLE 41

FR140729 substance was obtained by reacting FR133303 substance with 1-(6-dodecyloxy-2-naphthoyl)-1H-benzotriazole-3-oxide according to a method similar to that of Example 12.

IR (Nujol): 3300, 1610 $cm^{-1}$

NMR (DMSO-$d_6$+$D_2O$, δ): 0.85 (3H, t, J=6.6 Hz), 0.97 (3H, d, J=6.7 Hz), 1.07 (3H, d, J=5.9 Hz), 1.2–1.6 (18H, m), 1.7–2.1 (5H, m), 2.1–2.5 (3H, m), 2.5–2.7 (1H, m), 3.19 (1H, m), 3.45 (1H, m), 3.73 (2H, m), 3.9–4.5 (12H, m), 4.79 (1H, d, J=3 Hz), 4.87 (1H, d, J=3.8 Hz), 5.07 (1H, d, J=3 Hz), 6.74 (1H, d, J=8.1 Hz), 6.78 (1H, dd, J=8.1 and 2 Hz), 7.06 (1H, d, J=2 Hz ), 7.23 ( 1H, dd, J=8.9 and 2.4 Hz), 7.38 (1H, d, J=2.4 Hz), 7.85 (1H, d, J=8.7 Hz), 7.89 (1H, d, J=8.7 Hz), 7.93 (1H, d, J=8.9 Hz), 8.44 (1H, s)

FAB-MS e/z=1320 (M+Na)

EXAMPLE 42

FR140730 substance was obtained by reacting FR133303 substance with 1-(2-anthrylcarbonyl)-1H-benzotriazole-3-oxide according to a method similar to that of Example 12

IR (Nujol): 3300, 1620 $cm^{-1}$

FAB-MS e/z=1185 (M+Na)

EXAMPLE 43

FR143020 substance was obtained by reacting FR133303 substance with 1-[2-(4-octyloxyphenyl)acetyl]-1H-benzotriazole-3-oxide according to a method similar to that of Example 12.

IR (Nujol): 3300, 1620 $cm^{-1}$

NMR ($CD_3OD$, δ): 0.87 (3H, t, J=6.8 Hz), 1.0–1.2 (6H, m), 1.2–1.6 (10H, m), 1.6–1.85 (2H, m), 1.85–2.1 (3H, m), 2.3–2.6 (3H, m), 2.7–2.85 (1H, m), 3.32 (1H, m), 3.46 (2H, s), 3.7–4.7 (16H, m), 5.04 (1H, d, J=3.7 Hz), 5.23 (1H, d, J=2.7 Hz), 6.75–6.9 (3H, m), 7.01 (1H, d, J=8.3 Hz), 7.15 (2H, d, J=8.5 Hz), 7.30 (1H, s)

FAB-MS e/z=1227 (M+Na)

EXAMPLE 44

FR143021 substance was obtained by reacting FR133303 substance with 1-[3-(4-octyloxyphenyl)propionyl]-1H-benzotriazole- 3-oxide according to a method similar to that of Example 12.

IR (Nujol): 3300, 1620 $cm^{-1}$

FAB-MS e/z=1241 (M+Na)

EXAMPLE 45

FR141315 substance was obtained by reacting FR133303 substance with 1-[(E)-3-(4-octyloxyphenyl)acryloyl]-1H-benzotriazole-3-oxide according to a method similar to that of Example 12.

IR (Nujol): 3300, 1620 $cm^{-1}$

NMR (DMSO-$d_6$+$D_2O$, δ): 0.86 (3H, t, J=6.7 Hz), 0.97 (3H, d, J=6.7 Hz), 1.04 (3H, d, J=5.4 Hz), 1.2–1.5 (10H, m), 1.6–2.0 (5H, m), 2.1–2.5 (3H, m), 2.5–2.6 (1H, m), 3.17 (1H, m), 3.3–4.5 (15H, m), 4.79 (1H, d, J=3 Hz), 4.86 (1H, d, J=3.8 Hz), 5.01 (1H, d, J=3 Hz), 6.57 (1H, d, J=15.8 Hz), 6.74 (1H, d, J=8.2 Hz), 6.82 (1H, d, J=8.2 Hz), 6.97 (2H, d, J=8.8 Hz), 7.09 (1H, s), 7.34 (1H, d, J=15.8 Hz), 7.52 (2H, d, J=8.8 Hz)

FAB-MS e/z=1239 (M+Na)

EXAMPLE 46

FR140105 substance was obtained by reacting FR133303 substance with 1-($O^4$-octyl-N,N-dimethyl-L-tyrosyl)-1-H-benzotriazole-3-oxide according to a method similar to that of Example 12.

IR (Nujol): 3300, 1620 $cm^{-1}$

NMR ($CD_3OD$, δ): 0.91 (3H, t, J=6.8 Hz), 1.06 (3H, d, J=6.8 Hz), 1.12 (3H, d, J=6.1 Hz), 1.33 (10H, m), 1.74 (2H, m), 1.98 (3H, m), 2.40 (6H, s), 2.3–2.6 (3H, m), 2.8 (2H, m), 2.9–3.1 (1H, m), 3.3–3.5 (2H, m), 3.6–4.7 (16H, m), 5.06 (1H, d, J=3.8 Hz), 5.33 (1H, d, J=3 Hz), 6.77 (2H, d, J=8.6 Hz), 6.86 (1H, d, J=8.3 Hz), 7.03 (1H, dd, J=8.3 and 2 Hz), 7.07 (2H, d, J=8.6 Hz), 7.31 (1H, d, J=2 Hz)

EXAMPLE 47

FR141564 substance was obtained by reacting FR133303 substance with 4-octyloxyphenylsulfonyl chloride according to a method similar to that of Example 6.

IR (Nujol): 3300, 1620 $cm^{-1}$

NMR (DMSO-$d_6$+$D_2O$, δ): 0.87 (3H, t, J=6.7 Hz), 0.97 (3H, d, J=6.8 Hz), 1.04 (3H, d, J=5.7 Hz), 1.1–1.5 (10H, m), 1.6–2.1 (5H, m), 2.45 (3H, m), 2.5–2.7 (1H, m), 3.19 (1H, m), 3.7–4.5 ( 16H, m), 4.80 (1H, d, J=3 Hz), 4.88 (1H, d, J=4 Hz), 5.08 (1H, d, J=3 Hz), 6.74 (1H, d, J=8.2 Hz), 6.82 (1H, d, J=8.2 Hz), 6.84 (2H, d, J=8.7 Hz), 7.07 (1H, s), 7.51 (2H, d, J=8.7 Hz)

FAB-MS e/z=1249 (M+Na)

EXAMPLE 48

FR143170 substance was obtained by reacting FR133303 substance with 6-octyloxy-2-naphthylsulfonyl chloride according to a method similar to that of Example 6.

IR (Nujol): 3300, 1620 $cm^{-1}$

NMR ($CD_3OD$, δ): 0.29 (3H, d, J=6.0 Hz), 0.91 (3H, t, J=6.7 Hz), 1.07 (3H, d, J=6.9 Hz), 1.25–1.6 (10H, m), 1.7–2.2 (5H, m), 2.2–2.6 (4H, m), 3.37 (1H, m), 3.55–4.65 (17H, m), 4.97 (1H, m), 5.54 (1H, m), 6.84 (1H, d, J=8.3 Hz), 7.01 (1H, dd, J=8.4 and 2 Hz), 7.15–7.3 (3H, m), 7.75–8.0 (3H, m), 8.35 (1H, s)

FAB-MS e/z=1299 (M+Na)

EXAMPLE 49

To a solution of FR138364 substance obtained in Example 5 (0.24 g) in acetonitrile (5 ml), p-toluenesulfonic acid (0.132 g) was added, and the mixture was stirred for 8 hours at room temperature. The reaction mixture was added to water and the aqueous layer was adjusted to pH 4.5 with saturated aqueous sodium bicarbonate. The aqueous solution was subjected to column chromatography on DIAION HP-20, eluting with 80% aqueous methanol. The fractions containing the object compound were combined and evaporated under reduced pressure to remove methanol. The residue was lyophilized to give FR138912 substance (0.15 g).

IR (Nujol): 3300, 1620 $cm^{-1}$

FAB-MS e/z=1272 (M+K)

EXAMPLE 50

A mixture of FR138728 substance obtained in Example 8 (0.15 g) and 1-octyl-1,4-dihydropyridine-4-thione (0.031 g) in N,N-dimethylformamide was stirred for 1.5 hours under ice-cooling. The reaction mixture was pulverized in diethyl ether (50 ml). The precipitate was filtered and dried under reduced pressure in the presence of phosphorus pentoxide. The powder was added to water (300 ml) and adjusted to pH 4.5. The aqueous solution was subjected to column chromatography on DIAION HP-20 (50 ml) and eluted with 80% aqueous methanol. The fractions containing the object compound were combined and evaporated under reduced pressure to remove methanol. The residue was lyophilized to give FR138960 substance (0.15 g).

IR (Nujol): 3300, 1620 $cm^{-1}$

FAB-MS e/z=1222 (Free M+Na)

The following compounds (Examples 51 to 53) were obtained according to methods similar to that of Example 3.

EXAMPLE 51

FR138727 substance

NMR ($CD_3OD$, δ): 0.90 (3H, t, J=6.8 Hz), 1.05 (3H, d, J=6.8 Hz), 1.17–1.33 (13H, m), 1.6–1.8 (2H, m), 1.9–2.1 (3H, m), 2.50 (1H, m), 2.75 (1H, dd, J=16 and 4 Hz), 3.40 (1H, m), 3.7–3.8 (1H, M), 3.98 (2H, t, J=6.2 Hz), 3.9–4.2 (5H, m), 4.3–4.5 (5H, m), 4.5–4.7 (3H, m), 4.97 (1H, d, J=3 Hz), 5.06 (1H, s), 5.20 (1H, d, J=3 Hz), 5.40 (1H, d, J=3 Hz), 6.85 (1H, d, J=8.3 Hz), 6.95 (2H, d, J=8.5 Hz), 7.02 (1H, d, J=8.3 Hz), 7.30 (1H, d, J=8.5 Hz), 7.44 (1H, s)

EXAMPLE 52

FR138912 substance

IR (Nujol): 3300, 1620 $cm^{-1}$

EXAMPLE 53

FR138960 substance

IR (Nujol): 3300, 1620 $cm^{-1}$

The following compounds (Preparations 94 and 95) were obtained according to methods similar to that of Preparation 5.

Preparation 94

Succinimido 4-(4-heptyloxyphenyl)benzoate

IR (Nujol): 1760, 1740, 1600 $cm^{-1}$

NMR ($CDCl_3$, δ): 0.87 (3H, t, J=6.8 Hz), 1.2–1.7 (8H, m), 1.7–1.9 (2H, m), 2.92 (4H, s), 4.01 (2H, t, J=6.5 Hz), 7.00 (2H, d, J=8.8 Hz), 7.58 (2H, d, J=8.8 Hz), 7.69 (2H, d, J=8.5 Hz), 8.17 (2H, d, J=8.5 Hz)

Preparation 95

Succinimido 4-(4-hexyloxyphenoxy)benzoate

IR (Nujol): 1760, 1720, 1600 $cm^{-1}$

NMR ($CDCl_3$, δ): 0.92 (3H, t, J=6.8 Hz), 1.2–1.5 (6H, m), 1.7–1.9 (2H, m), 2.90 (4H, s), 3.96 (2H, t, J=6.5 Hz), 6.9–7.1 (6H, m), 8.07 (2H, d, J=9 Hz)

The structures of the compounds of Examples 54 and 55 are shown hereinbelow:

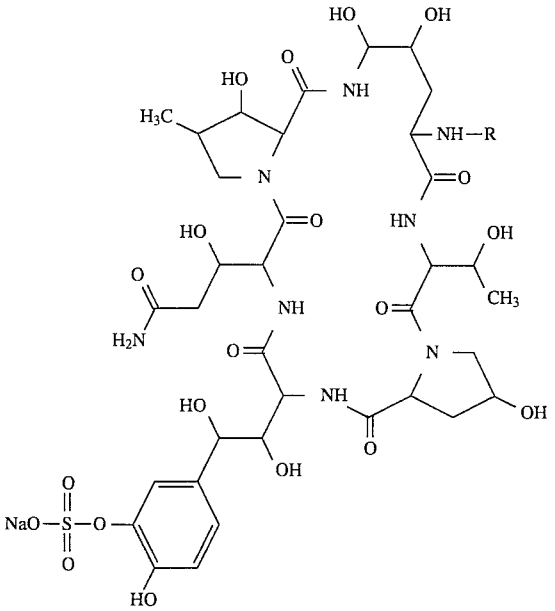

| Example No | Compound No. | R |
|---|---|---|
| 54 | FR144274 | —CO—⟨benzene⟩—⟨benzene⟩—O(CH₂)₆CH₃ |
| 55 | FR144271 | —CO—⟨benzene⟩—O—⟨benzene⟩—O(CH₂)₅CH₃ |

The following compounds (Examples 54 and 55) were obtained according to methods similar to that of Example 3.

EXAMPLE 54

FR144274

IR (Nujol): 3300, 1620 $cm^{-1}$

Anal. Calcd. for $C_{55}H_{73}N_8SO_{22}Na.6H_2O$: C: 48.53, H: 6.29, N: 8.23, S: 2.35

Found C: 48.36, H: 6.34, N: 8.15, S: 2.30

FAB-MS e/z=1275 (M+Na)

EXAMPLE 55

FR144271

Anal. Calcd. for $C_{54}H_{71}N_8SO_{23}Na.6H_2O$ C: 47.57, H: 6.14, N: 8.22, S: 2.35

Found C: 47.58, H: 6.05, N: 8.18, S: 2.27

FAB-MS e/z=1277 (M+Na)

Numerous modifications and variations of the present invention are possible in light of the above teachings. It is therefore to be understood that within the scope of the appended claims, the invention may be practiced otherwise than as specifically described herein.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: circular ( i i ) MOLECULE TYPE: peptide ( x i ) SEQUENCE DESCRIPTION: SEQ ID NO:1:

Xaa Thr Xaa Xaa Xaa Xaa
1 5

What is claimed as new and desired to be secured by Letters Patent of the United States is:

1. A method for the prevention or the treatment of *Pneumocystis carinii* pneumonia, which comprises administering an effective amount of a polypeptide compound of the formula (SEQ ID NO: 1):

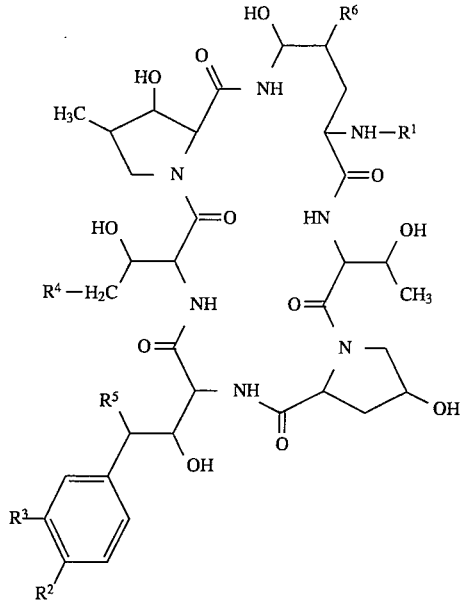

wherein $R^1$ is hydrogen or an acyl group, $R^2$ is hydroxy or acyloxy group, $R^3$ is hydroxy or hydroxysulfonyloxy, $R^4$ is hydrogen or carbamoyl, and $R^5$ and $R^6$ are each hydrogen or hydroxy, with the proviso that $R^5$ is hydrogen when $R^6$ is hydrogen, or a pharmaceutically acceptable salt thereof to a human being or an animal in need thereof.

* * * * *